US012258335B1

(12) United States Patent
Yang et al.

(10) Patent No.: US 12,258,335 B1
(45) Date of Patent: *Mar. 25, 2025

(54) MATRIX METALLOPROTEINASE (MMP) INHIBITORS AND METHODS OF USE THEREOF

(71) Applicant: Foresee Pharmaceuticals USA, Inc., Newark, DE (US)

(72) Inventors: Wenjin Yang, Newark, DE (US); Kai-Wei Chang, Newark, DE (US); Suying Liu, Newark, DE (US); Cheng-Han Tsai, Newark, DE (US)

(73) Assignee: Foresee Pharmaceuticals USA, Inc., Newark, DE (US)

( * ) Notice: Subject to any disclaimer, the term of this patent is extended or adjusted under 35 U.S.C. 154(b) by 279 days.

This patent is subject to a terminal disclaimer.

(21) Appl. No.: 17/055,483

(22) PCT Filed: May 14, 2019

(86) PCT No.: PCT/US2019/032131
§ 371 (c)(1),
(2) Date: Nov. 13, 2020

(87) PCT Pub. No.: WO2019/222157
PCT Pub. Date: Nov. 21, 2019

Related U.S. Application Data

(60) Provisional application No. 62/671,753, filed on May 15, 2018.

(51) Int. Cl.
*C07D 405/14* (2006.01)
*A61P 11/00* (2006.01)
*A61P 13/12* (2006.01)
*C07D 405/04* (2006.01)

(52) U.S. Cl.
CPC ............ *C07D 405/14* (2013.01); *A61P 11/00* (2018.01); *A61P 13/12* (2018.01); *C07D 405/04* (2013.01)

(58) Field of Classification Search
CPC ..... C07D 405/14; C07D 405/04; A61P 11/00; A61P 13/12
See application file for complete search history.

(56) References Cited

U.S. PATENT DOCUMENTS

| | | | |
|---|---|---|---|
| 6,352,976 B1 | 3/2002 | Warshawsky | |
| 7,179,831 B2 | 2/2007 | Yang | |
| 10,851,089 B2* | 12/2020 | Yang | C07D 401/14 |
| 2004/0067996 A1* | 4/2004 | Sheppeck | A61P 29/00 |
| | | | 548/319.1 |
| 2004/0072871 A1 | 4/2004 | Dublanchet | |
| 2006/0041000 A1* | 2/2006 | Yang | A61P 19/02 |
| | | | 548/315.4 |

FOREIGN PATENT DOCUMENTS

| | | |
|---|---|---|
| EP | 1288199 A1 | 3/2003 |
| EP | 1394159 A1 | 3/2004 |
| WO | 0040577 A1 | 7/2000 |
| WO | 02074752 A1 | 9/2002 |
| WO | 02096426 A1 | 12/2002 |
| WO | 2004020415 A1 | 3/2004 |
| WO | 2004108086 A2 | 12/2004 |

OTHER PUBLICATIONS

Patani et al. Bioisosterism: A rational Approach in Drug Design, Chem. Rev., 96, 3147-3176. (Year: 1996).*
Sheridan, The Most Common Chemical Replacements in Drug-Like Compounds, J. Chem. Inf. Comput. Sci, 42, 103-108. (Year: 2002).*
Registry STN Online, 2008, RN 1061319-03-06.
Hautamaki, et al., "Requirement for macrophage elastase for cigarette smoke-induced emphysema in mice.", Science, vol. 277, 5334, pp. 2002-2004 (Sep. 1997).
Matute-Bello, et al. "Essential Role of MMP-12 in Fas-Induced Lung Fibrosis.", Am. Journal of Respir. Cell. Mol. Bio., vol. 37 (2); pp. 210-221, (Apr. 2007).
Madala, et al., "Matrix Metalloproteinases 12-Deficiency Augments Extracellular Matrix Degrading Metalloproteinase and Attenuates IL-13 Dependent Fibrosis", The Journal of Immunology, 184, pp. 3955-3963, (Feb. 2010).
Sand, et al., "MMP Mediated Degradation of Type IV Collagen Alpha 1 and Alpha 3 Chains Reflects Basement Membrane Remodeling in Experimental and Clinical Fibrosis—Validation of Two Novel Biomarker Assays", PLOS ONE, 8:e84934, (2013), 12 pages.
Owen, et al., "The cell biology of leukocyte-mediated proteolysis.", J. Leukoc. Biology, vol. 65, pp. 137-150, (Feb. 1999).
Shapiro, et al., "Cloning and characterization of a unique elastolytic metalloproteinase produced by human alveolar macrophages.", J. Biol. Chem., vol. 268; 32, pp. 23824-9, (Nov. 1993).
Warner, et al., "Role of Metalloelastase in a Model of Allergic Lung Responses Induced by Cockroach Allergen", Am. J. Pathol., vol. 165; 6, pp. 1921-1930, (Dec. 2004).
Kaneko, et al., "Nephritis Anti-Glomerular Basement Membrane Factor for Glomerular Injury in Anti-Glomerular Basement Membrane Nephritis", The Journal of Immunology, 170:3377-3385, (2003).
Matsumoto, et al., "Expression and localization of matrix metalloproteinase-12 in the aorta of cholesterol-fed rabbits: relationship to lesion development.", vol. 153;1, pp. 109-119, (Jul. 1998).

(Continued)

*Primary Examiner* — Matthew P Coughlin
*Assistant Examiner* — Meghan C Heasley
(74) *Attorney, Agent, or Firm* — Ice Miller LLP

(57) ABSTRACT

Hydantoin based compounds useful as inhibitors of matrix metalloproteinases (MMPs), particularly macrophage elastase (MMP-12) are described. Also described are related compositions and methods of using the compounds to inhibit MMP-12 and treat diseases mediated by MMP-12, such as asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

21 Claims, 7 Drawing Sheets

(56) References Cited

OTHER PUBLICATIONS

Jormsjo, et al., "Allele-Specific Regulation of Matrix Metalloproteinase-12 Gene Activity is Associated With Coronary Artery Luminal Dimensions in Diabetic Patients With Manifest Coronary Artery Disease.", Circulation Research, 86:998-1003, (2000).

Pender, et al., "Role of macrophage metalloelastase in gut inflammation.", Ann. N.Y. Acad. Sci., vol. 1072:386-388, (Aug. 2006).

Makitalo, et al., "Matrix metalloproteinases in the restorative proctocolectomy pouch of pediatric ulcerative colitis", vol. 18, 30:4028-4036, (Aug. 2012).

International Search Report & Written Opinion issued in PCT/2019/032131 on Jul. 5, 2019, 12 pages.

International Search Report & Written Opinion issued in PCT/US2019/032127 on Jul. 19, 2019, 8 pages.

King, Med. Chem., Principle and Practice (1994), pp. 206-208.

Morrison, K. "Physical Science Level 3" Pearson Education: Capetown, 2008, pp. 16-18, at p. 18.

* cited by examiner (I) Collagen I (II) Collagen IV (III) MMP-12

(IV) TGF-β1

(V) Elastin (I) Collagen I (II) Collagen IV (III) MMP-12

(IV) TGF-β1

(V) Elastin

FIG. 2E
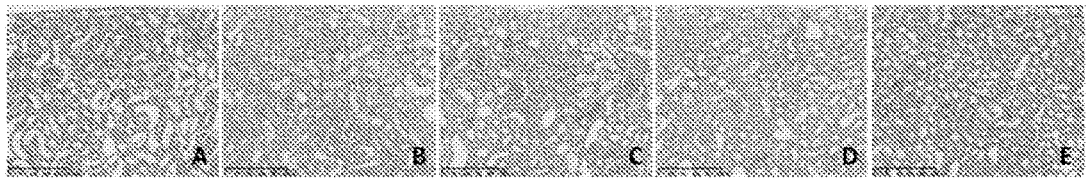
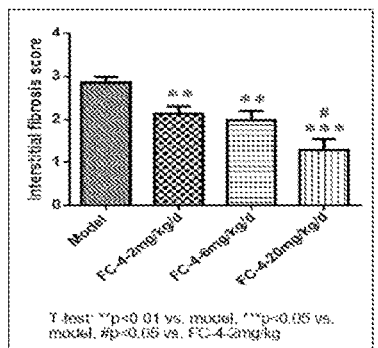
FIG. 2F
FIG. 2G
(I) Collagen I
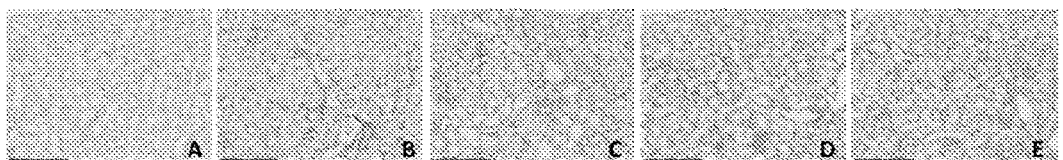
(II) Collagen IV
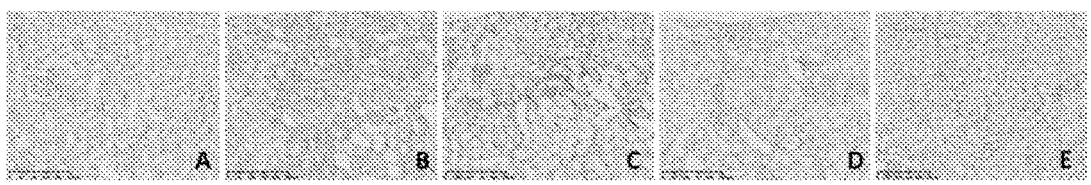
FIG. 2H
(I) Collagen I
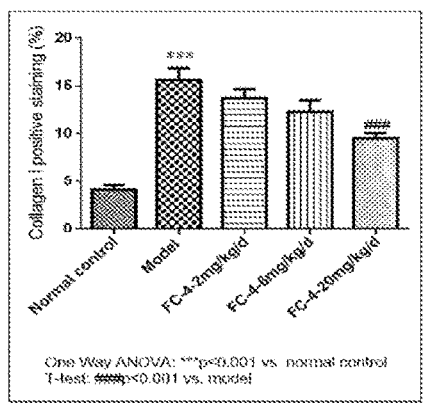
(II) Collagen IV
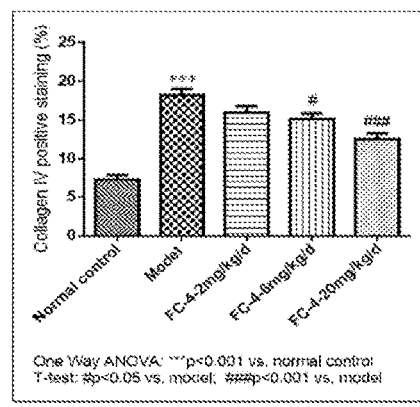

MATRIX METALLOPROTEINASE (MMP) INHIBITORS AND METHODS OF USE THEREOF

CROSS REFERENCE TO RELATED APPLICATION

This application is entitled to priority under 35 U.S.C. § 119(e) to U.S. Provisional Patent Application No. 62/671,753, filed May 15, 2018, the disclosure of which is incorporated herein by reference.

BACKGROUND OF THE INVENTION

Matrix metalloproteinases (MMPs) are a superfamily of proteinase enzymes that are important for the degradation of most extracellular matrix proteins during organogenesis, growth, and normal tissue turnover. MMPs are also believed to be important in the uncontrolled breakdown of connective tissue, which relates to a few disease processes such as rheumatoid arthritis, osteoarthritis, gastric ulceration, asthma, emphysema, and tumor metastasis. Therefore, inhibition of one or more MMPs may be of benefit in these diseases.

Human macrophage elastase (MMP-12) is a particular MMP. MMP-12 exhibits all the characteristics of other MMPs, but is preferentially produced from macrophages infiltrating into tissues where injury or remodeling is occurring, and degrades extracellular matrix. For example, increased levels of MMP-12 have been observed during the onset of emphysema. Additionally, an MMP-12 knock-out mouse model showed no development of emphysema after being exposed for a lengthy period of time to cigarette smoke (Hautamkai et al. *Science*, 1997, 277: 2002-2004). These data suggest that MMP-12 plays a role in disease progression of emphysema. The involvement of MMP-12 in the development of chronic asthma has also been suggested based on studies in an MMP-12 deficient model of asthma (Warner et al. *Am J Pathol.* 2004; 165(6): 1921-1930). In the Fas-induced model of acute lung injury, MMP12-deficient mice are protected from developing pulmonary fibrosis (Matute-Bello et al., *Am J Respir Cell Mol Biol.* 2007; 37(2): 210-221). In a model of pulmonary and hepatic fibrosis induced by *Schistosoma mansoni* infection, MMP-12 has profibrotic activities in the lung and liver (Madala et al. *J Immunol* 2010; 184:3955-3963). MMP-12 may also contribute to Idiopathic pulmonary fibrosis (IPF) pathogenesis by cleaving extracellular matrix (ECM) proteins, as BALF levels of a type IV collagen fragment generated by MMP-12 are increased in patients with IPF (Sand et al. *PLoS One* 2013; 8:e84934), and human MMP-12 can cleave a number of human ECM proteins in vitro (Owen et al. *J Leukoc Biol* 1999; 65:137-150). Together, these results suggest that inhibitors of MMP-12 may be useful in the treatment of pulmonary diseases, such as chronic obstructive pulmonary disease (COPD), emphysema, asthma, acute lung injury, idiopathic pulmonary fibrosis (IPF), sarcoidosis, systemic sclerosis, liver fibrosis and nonalcoholic steatohepatitis (NASH).

MMP-12 has been shown to be secreted from alveolar macrophages of smokers (Shapiro et al., *Journal of Biological Chemistry*, 1993, 268: 23824), in foam cells in atherosclerotic lesions (Matsumoto et al., *Am. J. Pathol.*, 1998, 153: 109), and in a nephritis rat model (Kaneko et al., *J. immunol.*, 2003, 170:3377). MMP-12 also plays a role in coronary artery disease (Jormsjo et al., *Circulation Research*, 2000, 86: 998). MMP-12 was also shown to be upregulated in inflammatory bowel disease (IBD) patients as well as in a T-cell mediated model of colitis and contribute to epithelial degradation and MMP-12–/– mice were protected against TNBS induced colitis (Pender et al., *Ann N Y Acad Sci.* 2006, 1072:386-8.). Epithelial and stromal MMP-12 along with MMP-3 and -7 have been also upregulated in pouch mucosa of pediatric onset UC, suggesting that the expression of MMPs pediatric UC pouch in the long-term shares characteristics with IBD (Mäkitalo et al., *World J Gastroenterol.* 2012, 18(30):4028-36). Taken together, these observations suggest that MMP-12 could be a target for treatment of these diseases.

In view of the involvement of MMP-12 in a number of diseases, attempts have been made to prepare inhibitors of MMP-12. A number of MMP-12 inhibitors are known (see e.g., International Patent Application Publication WO 00/40577; European Patent Application Publication EP 1 288 199 A1; U.S. Patent No. 63/529,761, and U.S. Patent Application Publication No. 2004/0072871; and European Patent Application Publication EP1394159).

A particular class of MMP inhibitors that have been described are the hydantoin derivatives. For example, International Patent Application Publication WO 02/096426 describes hydantoin derivatives of the general formula:

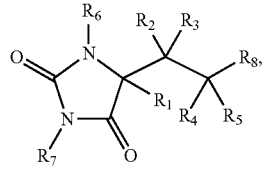

which are disclosed as being active as MMP inhibitors, particularly against tumor necrosis factor-alpha converting enzyme (TACE) and aggrecanase. A feature of the disclosed structures of these derivatives is a spiro-linkage between the hydantoin ring and its side chain. U.S. Patent Application Publication No. 2004/0067996 and International Patent Application Publication WO 2004/108086 describe similar hydantoin derivatives of the general formula:

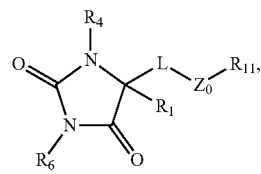

which are also described as MMP inhibitors, particularly for TACE and aggrecanase.

International Patent Application Publication WO 02/074752 describes the synthesis of MMP inhibitors and International Patent Application Publication WO 2004/020415 discloses MMP-12 inhibitors, which are hydantoin derivatives of the general formula:

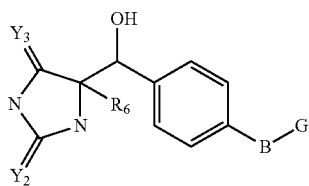

and

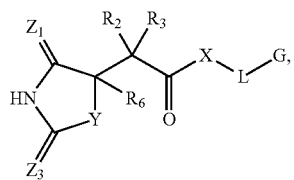

respectively. Some of the disclosed compounds showed MMP inhibitory activities, including MMP-12 inhibitory activity.

More recently, inhibitors of MMP-12 have been described in U.S. Pat. No. 7,179,831, which are hydantoin derivatives of the general formula:

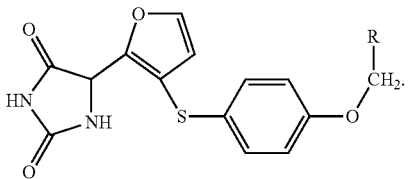

Hydantoin derivatives are a useful class of MMP inhibitors. However, there is a need in the art to identify hydantoin derivatives having improved specificity, potency, and pharmacological properties.

BRIEF SUMMARY OF THE INVENTION

The application satisfies this need by providing hydantoin derivatives having high activity and specificity for MMPs, particularly macrophage elastase (MMP-12).

In a general aspect, the application relates to a compound of formula (I):

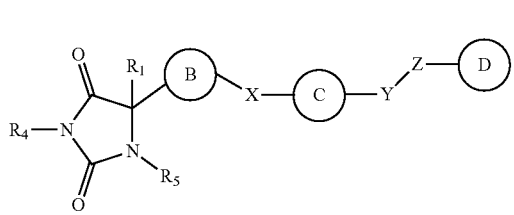

or a tautomer, stereoisomer, pharmaceutically acceptable salt, or solvate thereof,
wherein:
ring B is optionally substituted furanyl;
ring C is an optionally substituted aryl or optionally substituted heteroaryl;
ring D is an optionally substituted aryl or optionally substituted heteroaryl;
each of X, Y and Z is independently selected from the group consisting of $CH_2$, O, $NR_x$ and $S(O)_q$, wherein $R_x$ is hydrogen or alkyl;
$R_1$ is hydrogen or alkyl;
$R_4$ is hydrogen or alkyl;
$R_5$ is hydrogen; and
q is 0, 1, or 2,
provided that when ring D is phenyl, at least one of the following is true:
(i) $R_1$ is alkyl;
(ii) $R_2$ is not methoxy, chloro, or trifluoromethyl; and
(iii) Ring C is not unsubstituted phenyl.

In an embodiment, the application relates to a compound of formula (II):

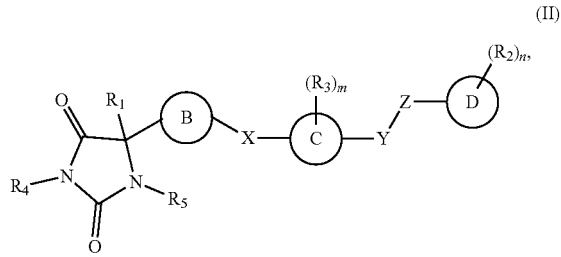

or a tautomer, stereoisomer, pharmaceutically acceptable salt, or solvate thereof,
wherein:
ring B is an optionally substituted furanyl;
ring C is aryl or heteoraryl;
ring D is aryl or heteroaryl;
each of X, Y and Z is independently selected from the group consisting of $CH_2$, O, $NR_x$ and $S(O)_q$, wherein $R_x$ is hydrogen or alkyl;
$R_1$ is hydrogen or alkyl;
each $R_2$ is independently selected from the group consisting of hydrogen, alkyl, halo, hydroxyl, haloalkyl, alkoxy, alkylthio, amino, amide, alkylamino, aminoalkyl, cyano, hydroxyalkyl, $-(CH_2)_pC(O)OR_6$, and $-(CH_2)_pOC(O)R_6$;
each $R_3$ is independently selected from the group consisting of hydrogen, alkyl and halo;
$R_4$ is hydrogen or alkyl;
$R_5$ is hydrogen;
each $R_6$ is independently selected from the group consisting of hydrogen and alkyl, wherein the alkyl is unsubstituted or substituted with one or more groups independently selected from the group consisting of amino, hydroxyl, halo, and alkoxy;
m is 1, 2, 3, or 4;
n is 1, 2, 3, 4, or 5;
p is 0, 1, 2, 3, 4, or 5; and
q is 0, 1, or 2,
provided that when ring D is phenyl, at least one of the following is true:
(i) $R_1$ is alkyl;
(ii) $R_2$ is not methoxy, chloro, or trifluoromethyl; and
(iii) Ring C is not unsubstituted phenyl.

In an embodiment, the application relates to a compound of formula (II), or a tautomer, stereoisomer, pharmaceutically acceptable salt, or solvate thereof, wherein ring C is phenyl In an embodiment, the application relates to a compound of formula (II), or a tautomer, stereoisomer, pharmaceutically acceptable salt, or solvate thereof, wherein ring D is pyridinyl or pyridinyl N-oxide.

In an embodiment, the application relates to a compound of formula (II), or a tautomer, stereoisomer, pharmaceutically acceptable salt, or solvate thereof, wherein $R_4$ is hydrogen.

In an embodiment, the application relates to a compound of formula (II), or a tautomer, stereoisomer, pharmaceutically acceptable salt, or solvate thereof, wherein $R_1$ is alkyl.

In an embodiment, the application relates to a compound of formula (II), or a tautomer, stereoisomer, pharmaceutically acceptable salt, or solvate thereof, wherein X is S and Z is $CH_2$.

In an embodiment, the application relates to a compound of formula (II), or a tautomer, stereoisomer, pharmaceutically acceptable salt, or solvate thereof, wherein X is S, Y is O, and Z is $CH_2$.

In an embodiment, the application relates to a compound of formula (II), or a tautomer, stereoisomer, pharmaceutically acceptable salt, or solvate thereof, wherein n is 1; and and $R_2$ is alkyl, alkoxy, hydroxy, hydroxyalkyl or amide.

In an embodiment, the application relates to a compound of formula (II), or a tautomer, stereoisomer, pharmaceutically acceptable salt, or solvate thereof, wherein n is 1; and $R_2$ is —$CH_3$, $C_{1-4}$ alkoxy, —OH, —$CH_2OH$, or —$C(O)NH_2$.

In an embodiment, the application relates to a compound of formula (III):

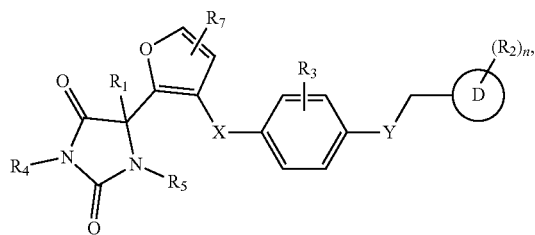

(III)

or a tautomer, stereoisomer, pharmaceutically acceptable salt, or solvate thereof,
wherein:
  $R_1$ is hydrogen or $C_{1-4}$ alkyl;
  X is S;
  Y is O, $CH_2$, NH, or $N(CH_3)$;
  each $R_2$ is independently selected from the group consisting of hydrogen, alkyl, hydroxyl, alkoxy, amide, and hydroxyalkyl;
  each $R_3$ is hydrogen, alkyl or halo;
  ring D is phenyl, pyridinyl, or pyridinyl N-oxide;
  each of $R_4$ and $R_5$ is hydrogen;
  $R_7$ is hydrogen or methyl; and
  n is 1 or 2.

In an embodiment, the application relates to a compound of formula (IV):

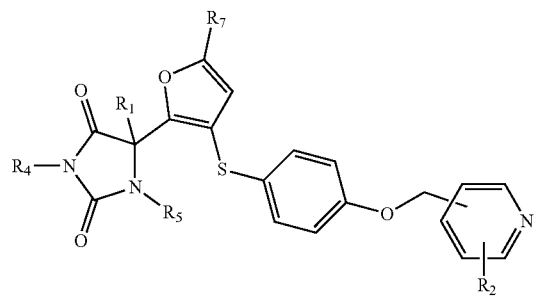

(IV)

or a tautomer, stereoisomer, pharmaceutically acceptable salt, or solvate thereof,
wherein:
  $R_1$ is hydrogen or alkyl;
  $R_2$ is selected from the group consisting of alkyl, amide, hydroxyl, alkoxy, and hydroxylalkyl;
  each of $R_4$ and $R_5$ is hydrogen; and
  $R_7$ is methyl or hydrogen.

In an embodiment, the application relates to a compound of formula (IV), or a tautomer, stereoisomer, pharmaceutically acceptable salt, or solvate thereof, wherein $R_2$ is —$CH_3$, $C_{1-4}$ alkoxy, —OH, —$CH_2OH$, or —$C(O)NH_2$.

In an embodiment, the application relates to a compound of formula (IV), or a tautomer, stereoisomer, pharmaceutically acceptable salt, or solvate thereof, wherein $R_1$ is $C_{1-4}$ alkyl.

In an embodiment, the application relates to a compound of formula (V), or a pharmaceutically acceptable salt thereof:

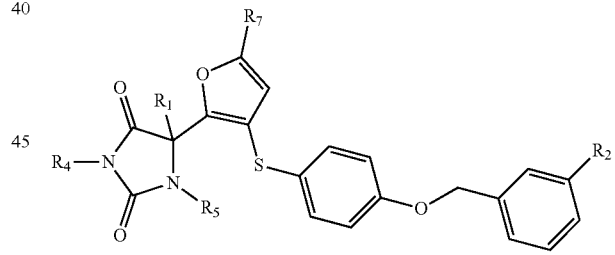

(V)

wherein:
  $R_1$ is alkyl;
  $R_2$ is selected from the group consisting of alkyl, amide, alkoxy, hydroxyl, and hydroxyalkyl;
  each of $R_4$ and $R_5$ is hydrogen; and
  $R_7$ is methyl or hydrogen.

In an embodiment, the application relates to a compound of formula (V), or a tautomer, stereoisomer, pharmaceutically acceptable salt, or solvate thereof, wherein $R_2$ is —$CH_3$, $C_{1-4}$ alkoxy, —OH, —$CH_2OH$, or —$C(O)NH_2$.

In an embodiment, the application relates to a compound of formula (V), or a tautomer, stereoisomer, pharmaceutically acceptable salt, or solvate thereof, wherein $R_1$ is $C_{1-4}$ alkyl.

In an embodiment, the application relates to a compound selected from the group consisting of the compounds listed in Table 1, or a tautomer, stereoisomer, pharmaceutically acceptable salt, or solvate thereof.

In an embodiment, the application relates to a compound selected from the group consisting of the compounds listed in Table 1, or a pharmaceutically acceptable salt thereof.

In another general aspect, the application relates to a pharmaceutical composition comprising a compound of the application as described herein, or a tautomer, stereoisomer, pharmaceutically acceptable salt, or solvate thereof, and at least one pharmaceutically acceptable carrier.

Other general aspects of the application relate to methods of inhibiting macrophage elastase (MMP-12) in a subject in need thereof, and methods of treating a disease mediated by macrophage elastase (MMP-12) in a subject in need thereof.

In an embodiment, the application relates to a method of inhibiting macrophage elastase (MMP-12) in a subject in need thereof, comprising administering to the subject a compound or pharmaceutical composition of the application.

In an embodiment, the application relates to a method of treating a disease mediated by macrophage elastase (MMP-12) in a subject in need thereof, comprising administering to the subject a compound or pharmaceutical composition of the application.

In some embodiments, the disease is selected from the group consisting of asthma, chronic obstructive pulmonary disease (COPD), emphysema, acute lung injury, and idiopathic pulmonary fibrosis (IPF), sarcoidosis, systemic sclerosis, liver fibrosis, nonalcoholic steatohepatitis (NASH), arthritis, cancer, heart disease, Inflammatory bowel disease (IBD), acute kidney injury (AKI), chronic kidney disease (CKD), Alport syndrome, and nephritis.

Also provided herein is a compound of the application or a tautomer, stereoisomer, pharmaceutically acceptable salt, or solvate thereof, or a composition of the application for use in a method of inhibiting macrophage elastase (MMP-12), or treating a disease mediated by macrophage elastase (MMP-12). In some embodiments, the disease is selected from the group consisting of asthma, chronic obstructive pulmonary disease (COPD), emphysema, acute lung injury, and idiopathic pulmonary fibrosis (IPF), sarcoidosis, systemic sclerosis, liver fibrosis, nonalcoholic steatohepatitis (NASH), arthritis, cancer, heart disease, Inflammatory bowel disease (IBD), acute kidney injury (AKI), chronic kidney disease (CKD), Alport syndrome, and nephritis.

Also provided herein is use of a compound of the application or a tautomer, stereoisomer, pharmaceutically acceptable salt, or solvate thereof, or a composition of the application in the manufacture of a medicament for inhibiting macrophage elastase (MMP-12) or treating a disease mediated by macrophage elastase (MMP-12). Preferably, the disease is selected from the group consisting of asthma, chronic obstructive pulmonary disease (COPD), emphysema, acute lung injury, and idiopathic pulmonary fibrosis (IPF), sarcoidosis, systemic sclerosis, liver fibrosis, nonalcoholic steatohepatitis (NASH), arthritis, cancer, heart disease, Inflammatory bowel disease (IBD), acute kidney injury (AKI), chronic kidney disease (CKD), Alport syndrome, and nephritis.

In yet another general aspect, the application relates to a method of preparing a pharmaceutical composition of the application, comprising combining a compound of the application, or a tautomer, stereoisomer, pharmaceutically acceptable salt, or solvate thereof, and at least one pharmaceutically acceptable carrier.

BRIEF DESCRIPTION OF THE FIGURES

The foregoing summary, as well as the following detailed description of the invention, will be better understood when read in conjunction with the appended figures. It should be understood that the invention is not limited to the precise embodiments shown in the drawings.

In the figures:

FIG. 1A shows hematoxylin and eosin (H&E) stained slides that were used to score bronchiole and pulmonary arteriole damage and inflammatory cell infiltration in fibrosis core and fibrosis board area according to the criteria set forth in Tables 3.2 and 3.3; FIG. 1B shows Masson Trichrome stained slides that were used for lung fibrosis scoring according to the criteria set forth in Table 3.4; criteria of histological features for lung fibrosis scoring: panel A: normal, panel B: score 1, panel C: score 2, panel D: score 3, panel E: score 4, panel F: score 5, panel G: score 6, panel H: score 7, panel I: score 8; FIG. 1C shows bronchial and arteriole damages in the fibrotic core of experimental SD rats by H&E staining at a magnification of ×200; panel A: Sham (Group 1), panel B: Model (Group 2), panel C: FC-4 (Group 4, 10 mg/kg/day), panel D: FC-4 (Group 5, 30 mg/kg/day), panel E: FC-4 (Group 6, 100 mg/kg/day); "a" refers to pulmonary arteriole and "b" refers to bronchia; FIG. 1D shows bronchial and arteriole damage in the border of fibrosis of experimental SD rats by H&E staining at a magnification of ×200; panel A: Sham (Group 1), panel B: Model (Group 2), panel C: FC-4 (Group 4, 10 mg/kg/day), panel D: FC-4 (Group 5, 30 mg/kg/day), panel E: FC-4 (Group 6, 100 mg/kg/day); "a" refers to pulmonary arteriole and "b" refers to bronchia; FIG. 1E graphically shows the bronchial and arteriole injury score in the fibrosis core of experimental SD rats; one-way ANOVA: *p<0.001 vs. model group; FIG. 1F shows the bronchial and arteriole injury score in the fibrosis border; one-way ANOVA: *p<0.001 vs. model, p<0.01 vs. model; FIG. 1G shows the histological changes in lung fibrosis of experimental SD rats by Masson Trichrome staining; panel A: Sham (Group 1), panel B: Model (Group 2), panel C: FC-4 (Group 4, 10 mg/kg/day), panel D: FC-4 (Group 5, 30 mg/kg/day), panel E: FC-4 (Group 6, 100 mg/kg/day); FIG. 1H graphically shows the left lung fibrosis score according to Ashcraft scoring for the experimental SD rats; one-way ANOVA: p<0.01 vs. model, *p<0.001 vs. model; FIG. 1I graphically shows the ratio of left lung fibrosis score according to Ashcraft scorings for the experimental SD rats; two-way ANOVA: *p<0.001 vs. model; FIG. 1J shows histological changes of collagen deposition, MMP-12 expression, TGF-β1 expression, and elastin expression of experimental SD rats by H&E staining at magnification ×200; (I) shows collagen I deposited on the alveolar wall in the fibrosis core as indicated by the arrow, (II) shows collagen IV deposited in the fibrosis core as indicated by the arrow, (III) shows MMP-12 expression in the fibrosis core with the arrows indicating MMP-12 expression on the alveolar wall and inflammatory cells in the fibrosis core, (IV) shows TGF-β1 expression in the fibrosis core with the arrows indicating TGF-β1 expression on the inflammatory cells in the fibrosis core, (V) shows elastin expression in fibrosis core with the arrows indicating elastin expression on the alveolar wall in the fibrosis core; for each of (I)-(V) panel A: Sham (Group 1), panel B: Model (Group 2), panel C: FC-4 (Group 4, 10 mg/kg/day), panel D: FC-4 (Group 5, 30 mg/kg/day), panel E: FC-4 (Group 6, 100 mg/kg/day); FIG. 1K shows positive staining score for collagen I deposition, collagen IV deposition, MMP-12 expression, TGF-β1 expression, and elastin expression of experimental SD rats; (I)-(V) correspond to (I)-(V) as described in FIG. 1J; for each of (I)-(V) panels A-F correspond to panels A-F as described in FIG. 1J; #p<0.05 vs. model; ##p<0.01 vs. model; ###p<0.001 vs model; p<0.01 vs. sham; *p<0.001 vs. sham; and FIGS. 2A-2H depict the results of the efficacy study of MMP-12 inhibitors on SD rat kidney fibrosis model by unilateral ureteral occlusion (UUO) described in Example 4; FIG. 2A shows changes in serum BUN at 2 weeks as compared to pre-operation (pre-OP) for each of the experimental SD rat groups; FIG. 2B shows changes in serum creatine at 2 weeks as compared to pre-operation (pre-OP) for each of the experimental SD rat groups; FIG. 2C shows histology images of kidneys from H&E staining at ×200 magnification; panel A: right kidney as normal control, panel B: vehicle treated animals, panel C: FC-4 treated animals (2 mg/kg/day), panel D: FC-4 treated animals (6 mg/kg/day), panel E: FC-4 treated animals (20 mg/kg/day); FIG. 2D shows the renal tubular damage score (I) and the renal interstitial inflammatory score (II) for each of the experimental SD rat groups; T-test in (I): *p<0.05 vs. model, ##p<0.01 vs. FC-4 (2 mg/kg/day); T-test in (II): p<0.05 vs. model, *p<0.001 vs. model, ##p<0.01 vs. FC-4 (6 mg/kg/day), $$$p<0.001 vs. FC-4(2 mg/kg/day); FIG. 2E shows histology images in the kidneys from Masson Trichrome staining at a magnification of ×200; panels A-H correspond to panels A-H as described in FIG. 2C; FIG. 2F shows the interstitial fibrosis score for kidney interstitial fibrosis in the cortex; T-test: p<0.01 vs. model, *p<0.05 vs. model, #p<0.05 vs. FC-4 (2 mg/kg/day); FIG. 2G shows collagen I deposition (I) and collagen IV deposition (II) in the cortex area of the left kidney by IHC staining at ×200 magnification; panels A-H correspond to panels A-H as described in FIG. 2C; FIG. 2H shows collagen I deposition positive staining (%) (I) and collagen IV deposition positive staining (%) (II) in the cortex area of the left kidney as determined from the IHC staining in FIG. 2G; One-way ANOVA: *p<0.001 vs. normal control; T-test: #p<0.05 vs. model, ##p<0.01 vs. model, ###p<0.001 vs. model.

DETAILED DESCRIPTION OF THE INVENTION

Figure 1A:
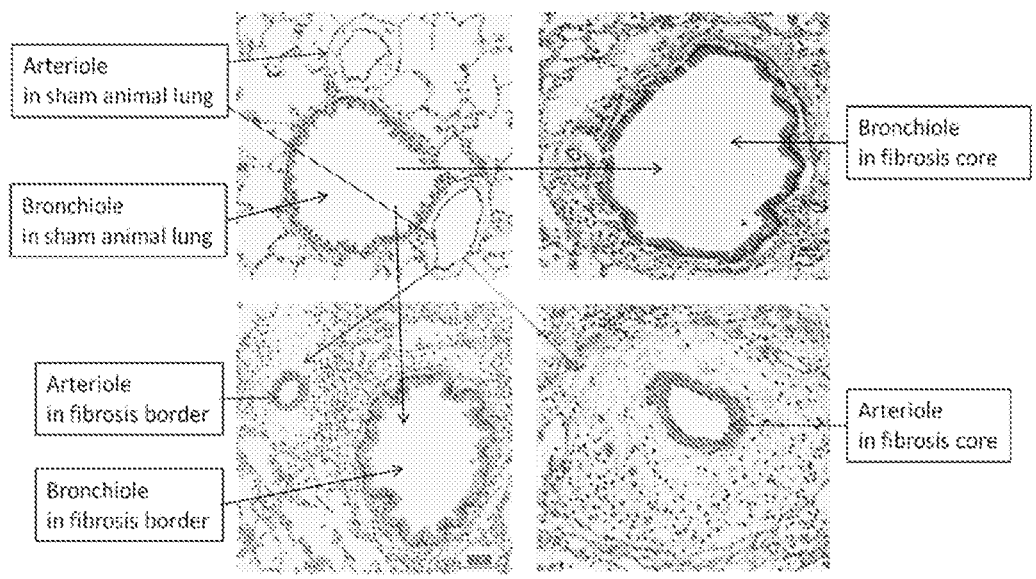
FIGS. 1A-1K depict the results of the therapeutic efficacy study of an MMP-12 inhibitor according to an embodiment of the application in a bleomycin-induced Sprague Dawley (SD) rat unilateral lung fibrosis model for idiopathic pulmonary fibrosis (IPF) as described in Example 3.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the application can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

Unless otherwise stated, any numerical value, such as a concentration or a concentration range described herein, are to be understood as being modified in all instances by the term "about." Thus, a numerical value typically includes ±10% of the recited value. For example, the recitation of "10-fold" includes 9-fold and 11-fold. As used herein, the use of a numerical range expressly includes all possible subranges, all individual numerical values within that range, including integers within such ranges and fractions of the values unless the context clearly indicates otherwise.

As used herein, "subject" means any animal, preferably a mammal, most preferably a human, to whom will be or has been treated by a method according to an embodiment of the application. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

The phrase "pharmaceutically acceptable salt(s)", as used herein, means those salts of a compound of interest that are safe and effective for topical use in mammals and that possess the desired biological activity. Pharmaceutically acceptable salts include salts of acidic or basic groups present in the specified compounds. Pharmaceutically acceptable acid addition salts include, but are not limited to, hydrochloride, hydrobromide, hydroiodide, nitrate, sulfate, bisulfate, phosphate, acid phosphate, isonicotinate, carbonate, bicarbonate, acetate, lactate, salicylate, citrate, tartrate, propionate, butyrate, pyruvate, oxalate, malonate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds used in the application can form pharmaceutically acceptable salts with various amino acids. Suitable base salts include, but are not limited to, aluminum, calcium, lithium, magnesium, potassium, sodium, zinc, bismuth, and diethanolamine salts. For a review on pharmaceutically acceptable salts see Berge et al., 66 *J. Pharm. Sci.* 1-19 (1977), incorporated herein by reference.

As used herein, the term "alkyl" means a saturated, monovalent, unbranched or branched hydrocarbon chain. An alkyl group can be unsubstituted or substituted with one or more suitable substituents. Examples of alkyl groups include, but are not limited to, methyl (Me), ethyl (Et), propyl (e.g., n-propyl, isopropyl), butyl (e.g., n-butyl, isobutyl, tert-butyl), and pentyl (e.g., n-pentyl, isopentyl, neopentyl), etc. An alkyl group can have a specified number of carbon atoms. When numbers appear in a subscript after the symbol "C", the subscript defines with more specificity the number of carbon atoms that a particular alkyl can contain. For example, "$C_1$ to $C_{10}$ alkyl" or "$C_{1-10}$ alkyl" is intended to include Cl, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having one to six carbon atoms.

The term "alkoxy" as used herein refers to an —O-alkyl group, wherein alkyl is as defined above. An alkoxy group is attached to the parent molecule through an oxygen atom. An alkoxy group can have a specified number of carbon atoms. For example, "$C_1$ to $C_{10}$ alkoxy" or "$C_{1-10}$ alkoxy" is intended to include Cl, $C_2$, $C_3$, $C_4$, $C_5$, $C_6$, $C_7$, $C_8$, $C_9$, and $C_{10}$ alkoxy groups. Additionally, for example, "$C_1$ to $C_6$ alkoxy" or "$C_{1-6}$ alkoxy" denotes alkoxy having 1 to 6 carbon atoms. Examples of alkoxy include, but are not limited to, methoxy, ethoxy, propoxy (e.g., n-propoxy, isopropoxy), butoxy (e.g., n-butoxy, isobutoxy, tert-butoxy), pentyloxy (e.g., n-pentyloxy, isopentyloxy, neopentyloxy), etc. An alkoxy group can be unsubstituted or substituted with one or more suitable substituents. Similarly, "alkylthio" or "thioalkoxy" represents an alkyl group as defined above attached through a sulfur bridge, for example, —S—methyl, —S-ethyl, etc. Representative examples of alkylthio include, but are not limited to, —$SCH_3$, —$SCH_2CH_3$, etc.

As used herein, the term "halogen" means fluorine, chlorine, bromine, or iodine. Correspondingly, the term "halo" means fluoro, chloro, bromo, and iodo.

"Haloalkyl" is intended to include both branched and straight-chain saturated aliphatic hydrocarbon groups substituted with one or more halogen atoms. Examples of haloalkyl include, but are not limited to, fluoromethyl, difluoromethyl, trifluoromethyl, chloromethyl, dichloromethyl, trichloromethyl, pentafluoroethyl, pentachloroethyl, 2,2,2-trifluoroethyl, heptafluoropropyl, and heptachloropropyl.

The terms "hydroxy" and "hydroxyl" can be used interchangeably, and refer to —OH.

The term "carboxy" refers to —COOH.

The term "cyano" refers to —CN.

The term "amino" refers to —$NH_2$. The term "alkylamino" refers to an amino group in which one or both of the hydrogen atoms attached to nitrogen is substituted with an alkyl group. For example, alkylamino includes methylamino (—$NHCH_3$), dimethylamino (—$N(CH_3)_2$), —$NHCH_2CH_3$, etc.

The term "aminoalkyl" as used herein is intended to include both branched and straight-chain saturated aliphatic hydrocarbon groups substituted with one or more amino groups. For example, "$C_{1-4}$ aminoalkyl" is intended to include Cl, $C_2$, $C_3$, and $C_4$ alkyl groups substituted with one or more amino groups. Representative examples of aminoalkyl groups include, but are not limited to, —$CH_2NH_2$, —$CH_2CH_2NH_2$, and —$CH_2CH(NH_2)CH_3$.

As used herein, "amide" refers to —$C(O)N(R)_2$, wherein each R is independently an alkyl group or a hydrogen. Examples of amides include, but are not limited to, —$C(O)NH_2$, —$C(O)NHCH_3$, and —$C(O)N(CH_3)_2$.

The terms "hydroxylalkyl" and "hydroxyalkyl" are used interchangeably, and refer to an alkyl group substituted with one or more hydroxyl groups. The alkyl can be a branched or straight-chain aliphatic hydrocarbon. Examples of hydroxylalkyl include, but are not limited to, hydroxylmethyl (—$CH_2OH$), hydroxylethyl (—$CH_2CH_2OH$), etc.

The term "aryl" as used herein is a group that contains any carbon-based aromatic group including, but not limited to, phenyl, naphthyl, anthracenyl, phenanthranyl, and the like. Aryl moieties are well known and described, for example, in Lewis, R. J., ed., *Hawley's Condensed Chemical Dictionary*, $13^{th}$ Edition, John Wiley & Sons, Inc., New York (1997). An aryl group can be substituted or unsubstituted with one or more suitable substituents. An aryl group can be a single ring structure (i.e., monocyclic) or comprise multiple ring structures (i.e., polycyclic) that are fused ring structures. Preferably, an aryl group is a monocyclic aryl group for instance phenyl.

As used herein, the term "heteroaryl" includes stable monocyclic and polycyclic aromatic hydrocarbons that contain at least one heteroatom ring member such as sulfur, oxygen, or nitrogen. Heteroaryl can be monocyclic or polycyclic, e.g., bicyclic or tricyclic. Each ring of a heteroaryl group containing a heteroatom can contain one or two oxygen or sulfur atoms and/or from one to four nitrogen atoms provided that the total number of heteroatoms in each ring is four or less and each ring has at least one carbon atom. For bicyclic heteroaryl groups, the fused rings completing the bicyclic group can contain only carbon atoms and can be saturated, partially saturated, or unsaturated. Heteroaryl groups which are polycyclic, e.g., bicyclic or tricyclic must include at least one fully aromatic ring but the other fused ring or rings can be aromatic or non-aromatic. The heteroaryl group can be attached at any available nitrogen or carbon atom of any ring of the heteroaryl group. Preferably, the term "heteroaryl" refers to 5- or 6-membered monocyclic groups and 9- or 10-membered bicyclic groups which have at least one heteroatom (O, S, or N) in at least one of the rings, wherein the heteroatom-containing ring preferably has 1, 2, or 3 heteroatoms, more preferably 1 or 2 heteroatoms, selected from O, S, and/or N. A heteroaryl group can be unsubstituted, or substituted with one or more suitable substituents. The nitrogen heteroatom(s) of a heteroaryl can be substituted or unsubstituted. The nitrogen and sulfur heteroatom(s) of a heteroaryl can optionally be oxidized (i.e., N—O and $S(O)_r$, wherein r is 0, 1 or 2).

Exemplary monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl. Exemplary bicyclic heteroaryl groups include, but are not limited to, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridinyl, furopyridinyl, dihydroisoindolyl, and tetrahydroquinolinyl.

In accordance with convention used in the art:

is used in structural formulas herein to depict the bond that is the point of attachment of the moiety or substituent to the core or backbone structure.

When a bond to a substituent is shown to cross a bond connecting two atoms in a ring, then such substituent can be bonded to any atom on the ring.

As referred to herein, the term "substituted" means that at least one hydrogen atom is replaced with a non-hydrogen group, provided that all normal valencies are maintained and that the substitution results in a stable compound. When a particular group is "substituted," that group can have one or more substituents, preferably from one to five substituents, more preferably from one to three substituents, most preferably from one to two substituents, independently selected from the list of substituents. The term "independently" when used in reference to substituents, means that when more than one of such substituents is possible, such substituents can be the same or different from each other. Examples of suitable substituents include, but are not limited to, alkyl, halogen, alkoxy, amide, alkythio, amine, alkylamine, aminoalkyl, hydroxyalkyl, hydroxyl, carboxyl, etc., such as $C_{1-4}$ alkyl, $C_{1-3}$ alkoxy, —OH, —COOH, —F, —Cl, —C(O)NHCH$_3$, —C(O)N(CH$_3$)$_2$.

When any variable occurs more than one time in any constituent or formula for a compound, its definition at each occurrence is independent of its definition at every other occurrence. Thus, for example, if a group is shown to be substituted with 0-3 R groups, then said group can be optionally substituted with up to three R groups, and at each occurrence, R is selected independently from the definition of R.

The terms "optional" or "optionally" mean that the event or circumstance described subsequently can, but need not, occur, and such a description includes the situation in which the event or circumstance does or does not occur. For example, "optionally substituted aryl" means that a substituent group can be, but need not be, present, and such a description includes the situation of the aryl group being substituted by a suitable substituent and the aryl group being not substituted by any substituent.

One skilled in the art will recognize that in certain embodiments compounds of the application can have one or more asymmetric carbon atoms in their structure. As used herein, any chemical formulas with bonds shown only as solid lines and not as solid wedged or hashed wedged bonds, or otherwise indicated as having a particular configuration (e.g., R or S) around one or more atoms, contemplates each possible stereoisomer, or mixture of two or more stereoisomers. In other words, if the stereochemistry of a structure is not specified, the structure is intended to encompass all individual stereoisomers and mixtures thereof. Stereoisomers includes enantiomers and diastereomers. Enantiomers are stereoisomers that are non-super-imposable mirror images of each other. A 1:1 mixture of a pair of enantiomers is a racemate or racemic mixture. Diastereomers (or diastereoisomers) are stereoisomers that are not enantiomers, i.e., they are not related as mirror images, and occur when two or more stereoisomers of a compound have different configurations at one or more of the equivalent stereocenters and are not mirror images of each other. Substituent groups (e.g., alkyl, heterocyclyl, etc.) can contain stereocenters in either the R or S configuration.

Thus, included within the scope of the invention are the stereochemically pure isomeric forms of the compounds of the invention (i.e., a single enantiomer or a single diastereomer) as well as mixtures thereof including their racemates. When a specific stereoisomer is identified, this means that the stereoisomer is substantially free, i.e., associated with less than 50%, preferably less than 20%, more preferably less than 5%, in particular less than 2% and most preferably less than 1% of the other stereoisomers. For example, when a compound is for instance specified as (R), this means that the compound is substantially free of the (S) isomer. Compounds of the application described herein can be used as racemic mixtures, enantiomerically or diastereomerically enriched mixtures, or as enantiomerically or diastereomerically pure individual stereoisomers.

Stereochemically pure isomeric forms can be obtained by techniques known in the art in view of the present disclosure. For example, diastereoisomers can be separated by physical separation methods such as fractional crystallization and chromatographic techniques, and enantiomers can be separated from each other by the selective crystallization of the diastereomeric salts with optically active acids or bases or by chiral chromatography. Pure stereoisomers can also be prepared synthetically from appropriate stereochemically pure starting materials, or by using stereoselective reactions.

Compounds of the application can also form tautomers. The term "tautomer" refers to compounds that are interchangeable forms of a particular compound structure and that vary in the displacement of hydrogen atoms and electrons. Tautomers are constitutional isomers of chemical compounds that readily interconvert, usually resulting in relocation of a proton (hydrogen). Thus, two structures can be in equilibrium through the movement of pi electrons and an atom (usually hydrogen). All tautomeric forms and mixtures of tautomers of the compounds of the application are including with the scope of the application.

Compounds of the application can exist in solvated and unsolvated forms. The term "solvate" means a physical association, e.g., by hydrogen bonding, of a compound of the application with one or more solvent molecules. The solvent molecules in the solvate can be present in a regular arrangement and/or a non-ordered arrangement. The solvate can comprise either a stoichiometric or nonstoichiometric amount of the solvent molecules. "Solvate" encompasses both solution-phase and isolable solvates. Compounds of the application can form solvates with water (i.e., hydrates) or common organic solvents. Exemplary solvates include, but are not limited to, hydrates, ethanolates, methanolates, and isopropanolates. Methods of solvation are generally known in the art.

Also included within the scope of the application are all isotopes of atoms occurring in the compounds of the application. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

As used herein, the name of a compound is intended to encompass all possible existing isomeric forms (e.g., optical isomer, enantiomer, diastereomer, racemate or racemic mixture), tautomers, and pharmaceutically acceptable salts, of the compound.

Compounds

In a general aspect, the application relates to a compound of formula (I):

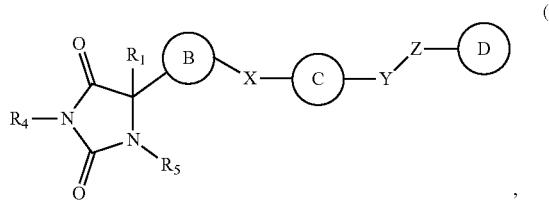

or a tautomer, stereoisomer, pharmaceutically acceptable salt, or solvate thereof,
wherein:
  ring B is an optionally substituted furanyl;
  ring C is an optionally substituted aryl or optionally substituted heteoraryl;
  ring D is an optionally substituted aryl or optionally substituted heteroaryl;
  each of X, Y and Z is independently selected from the group consisting of $CH_2$, O, $NR_x$ and $S(O)_q$, wherein $R_x$ is hydrogen or alkyl;
  $R_1$ is hydrogen or alkyl;
  $R_4$ is hydrogen or alkyl;
  $R_5$ is hydrogen; and
  q is 0, 1, or 2,
provided that when ring D is phenyl at least one of the following is true:
  (i) $R_1$ is alkyl;
  (ii) $R_2$ is not methoxy, chloro, or trifluoromethyl; and
  (iii) ring C is not unsubstituted phenyl.

In an embodiment, provided is a compound of formula (II):

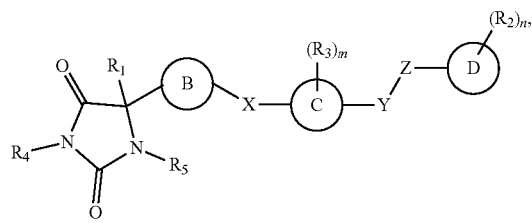

or a tautomer, stereoisomer, pharmaceutically acceptable salt, or solvate thereof,
wherein:
  ring B is an optionally substituted furanyl;
  ring C is aryl or heteroaryl;
  ring D is aryl or heteroaryl;
  each of X, Y and Z is independently selected from the group consisting of O, $CH_2$, $NR_x$ and $S(O)_q$, wherein $R_x$ is hydrogen or alkyl;
  $R_1$ is hydrogen or alkyl;
  each $R_2$ is independently selected from the group consisting of hydrogen, alkyl, halo, hydroxyl, haloalkyl, alkoxy, alkylthio, amino, amide, alkylamino, aminoalkyl, cyano, hydroxyalkyl, $-(CH_2)_pC(O)OR_6$, and $-(CH_2)_pOC(O)R_6$;
  each $R_3$ is independently selected from the group consisting of hydrogen, alkyl and halo;
  $R_4$ is hydrogen or alkyl; $R_5$ is hydrogen;
  each $R_6$ is independently selected from the group consisting of hydrogen and alkyl, wherein the alkyl is unsubstituted or substituted with one or more groups independently selected from the group consisting of amino, hydroxyl, halo, and alkoxy;
  m is 1, 2, 3, or 4;
  n is 1, 2, 3, 4, or 5;
  p is 0, 1, 2, 3, 4, or 5; and
  q is 0, 1, or 2,
provided that when ring D is phenyl at least one of the following is true:
  (i) $R_1$ is alkyl;
  (ii) $R_2$ is not methoxy, chloro, or trifluoromethyl; and
  (iii) ring C is not unsubstituted phenyl.

In an embodiment, provided is a compound of formula (II), or a tautomer, stereoisomer, pharmaceutically acceptable salt, or solvate thereof, wherein ring C is optionally substituted aryl, preferably optionally substituted phenyl.

In an embodiment, provided is a compound of formula (II), or a tautomer, stereoisomer, pharmaceutically acceptable salt, or solvate thereof, wherein ring C is optionally substituted heteroaryl, preferably optionally substituted pyridinyl.

In an embodiment, provided is a compound of formula (II), or a tautomer, stereoisomer, pharmaceutically acceptable salt, or solvate thereof, wherein m is 1, and $R_3$ is independently hydrogen, alkyl, or halo, preferably hydrogen, $-CH_3$, $-F$, or $-Cl$, more preferably hydrogen.

In an embodiment, provided is a compound of formula (II), or a tautomer, stereoisomer, pharmaceutically acceptable salt, or solvate thereof, wherein ring C is phenyl, m is 1, and $R_3$ is hydrogen.

In an embodiment, provided is a compound of formula (II), or a tautomer, stereoisomer, pharmaceutically acceptable salt, or solvate thereof, wherein ring D is an optionally substituted aryl, preferably an optionally substituted phenyl. In such embodiments in which ring D is phenyl, at least one of the following conditions is satisfied: (i) $R_1$ is alkyl; (ii) $R_2$ is not methoxy, chloro, or trifluoromethyl; and/or (iii) ring C is not unsubstituted phenyl.

In an embodiment, provided is a compound of formula (II), or a tautomer, stereoisomer, pharmaceutically acceptable salt, or solvate thereof, wherein ring D is an optionally substituted heteroaryl.

In an embodiment, provided is a compound of formula (II), or a tautomer, stereoisomer, pharmaceutically acceptable salt, or solvate thereof, wherein ring D is optionally substituted with 1, 2, 3, 4, or 5 substitutent groups, preferably 1 or 2 substituent groups, independently selected from the group consisting of alkyl, halo, haloalkyl, alkoxy, alkylthio, amino, amide, alkylamino, aminoalkyl, cyano, hydroxyalkyl, $-(CH_2)_pC(O)OR_6$, and $-(CH_2)_pOC(O)R_6$, wherein p is 0, 1, 2, 3, 4, or 5. The substituent group, if present, can be attached at any position of ring D. Preferably, ring D is substituted with one substituent group.

In an embodiment, provided is a compound of formula (II), or a tautomer, stereoisomer, pharmaceutically acceptable salt, or solvate thereof, wherein ring D is a monocyclic aryl or monocyclic heteroaryl group substituted with one substituent at the meta position, preferably phenyl or pyridinyl substituted at the meta position, relative to the bond to variable Z. Particularly preferred substituent groups for ring D include methyl (—CH$_3$), amide (—C(O)NH$_2$), methoxy (—OCH$_3$), hydroxyl (—OH), and hydroxylmethyl (—CH$_2$OH).

In a particular embodiment, ring D is phenyl.

In another particular embodiment, ring D is pyridinyl.

In another particular embodiment ring D is pyridinyl N-oxide.

In an embodiment, provided is a compound of formula (II), or a tautomer, stereoisomer, pharmaceutically acceptable salt, or solvate thereof, wherein n is 1 and R$_2$ is C$_{1-4}$ alkoxy (e.g., —OCH$_3$, —OCH$_2$CH$_2$CH$_3$, —OCH$_2$CH$_3$, —OCH(CH$_3$)$_2$, —OCH$_2$CH(CH$_3$)$_2$), C$_{1-4}$ alkyl (e.g., —CH$_3$, —OH, —CH$_2$CH$_3$, —CH$_2$CH(CH$_3$)$_2$), —CH$_2$OH, —OH, —COOH, —C(O)NH$_2$, —C(O)NHCH$_3$, or —CH$_2$OC(O)CH(NH$_2$)CH(CH$_3$)$_2$, —C(O)NH$_2$, —C(O)NHCH$_3$. Preferably R$_2$ is —CH$_3$, —C(O)NH$_2$, —CH$_2$OH, —OCH$_3$, or OH.

In an embodiment, provided is a compound of formula (II), or a tautomer, stereoisomer, pharmaceutically acceptable salt, or solvate thereof, wherein ring D is:

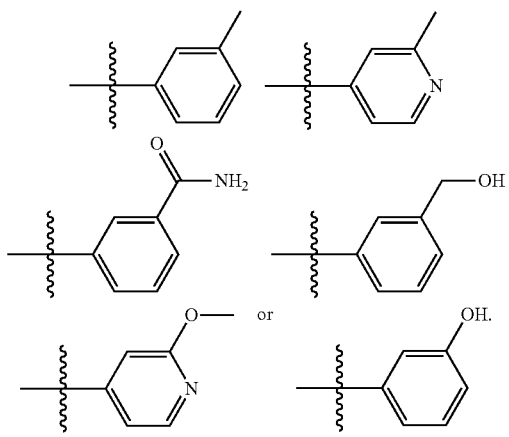

According to embodiments of the application, the chiral carbon atom of the hydantoin moiety can be unsubstituted (i.e., R$_1$ is hydrogen) or substituted. When substituted, the R$_1$ substituent is preferably alkyl. Preferred alkyl groups for substitution of the chiral carbon atom of the hydantoin moiety include C$_{1-4}$ alkyl groups, such as methyl, ethyl, propyl, isopropyl, butyl, isobutyl, etc.

In an embodiment, provided is a compound of formula (II), or a tautomer, stereoisomer, pharmaceutically acceptable salt, or solvate thereof, wherein R$_1$ is hydrogen, —CH$_3$, —CH$_2$CH$_3$, —CH$_2$CH$_2$CH$_3$, —CH(CH$_3$)$_2$, or —CH$_2$CH(CH$_3$)$_2$.

In an embodiment, provided is a compound of formula (II), or a tautomer, stereoisomer, pharmaceutically acceptable salt, or solvate thereof, wherein R$_1$ is hydrogen.

Substitution of the nitrogen atoms of the hydantoin moiety is also possible. According to embodiments of the application, R$_4$ and R$_5$ are each independently hydrogen or alkyl. Preferred alkyl groups include methyl.

In an embodiment, provided is a compound of formula (II), or a tautomer, stereoisomer, pharmaceutically acceptable salt, or solvate thereof, wherein R$_4$ is hydrogen or —CH$_3$ and R$_5$ is —CH$_3$.

In an embodiment, provided is a compound of formula (II), or a tautomer, stereoisomer, pharmaceutically acceptable salt, or solvate thereof, wherein each of R$_4$ and R$_5$ is hydrogen.

According to embodiments of the application, each of X, Y, and Z is independently selected from the group consisting of O, NR$_x$, CH$_2$, and S(O)$_q$, wherein q is 0, 1, or 2 and R$_x$ is hydrogen or alkyl. As such, each of the linker units X, Y and Z is independently selected from O, S, S(O), SO$_2$, NH, N-alkyl, and CH$_2$. Preferably, each of X, Y, and Z is independently selected from S, S(O), S(O)$_2$, CH$_2$, and O, more preferably S, CH$_2$, and O.

In an embodiment, provided is a compound of formula (II), or a tautomer, stereoisomer, pharmaceutically acceptable salt, or solvate thereof, wherein Z is CH$_2$.

In an embodiment, provided is a compound of formula (II), or a tautomer, stereoisomer, pharmaceutically acceptable salt, or solvate thereof, wherein X is S.

In an embodiment, provided is a compound of formula (II), or a tautomer, stereoisomer, pharmaceutically acceptable salt, or solvate thereof, wherein X is S; Y is O, CH$_2$, NH, or NH(CH$_3$); and Z is CH$_2$.

In an embodiment, provided is a compound of formula (II), or a tautomer, stereoisomer, pharmaceutically acceptable salt, or solvate thereof, wherein X is O, Y is O, and Z is CH$_2$.

In an embodiment, provided is a compound of formula (II), or a tautomer, stereoisomer, pharmaceutically acceptable salt, or solvate thereof, wherein X is S, Y is S, and Z is CH$_2$.

In an embodiment, provided is a compound of formula (II), or a tautomer, stereoisomer, pharmaceutically acceptable salt, or solvate thereof, wherein X is O, Y is S, and Z is CH$_2$.

In an embodiment, provided is a compound of formula (II), or a tautomer, stereoisomer, pharmaceutically acceptable salt, or solvate thereof, wherein X is S, Y is O, and Z is CH$_2$.

In an embodiment, provided is a compound of formula (II), or a tautomer, stereoisomer, pharmaceutically acceptable salt, or solvate thereof, wherein Z is O, Y is CH$_2$, and X is S.

In an embodiment, provided is a compound of formula (II), or a tautomer, stereoisomer, pharmaceutically acceptable salt, or solvate thereof, wherein Z is S, Y is CH$_2$, and X is O.

In an embodiment, provided is a compound of formula (II), or a tautomer, stereoisomer, pharmaceutically acceptable salt, or solvate thereof, wherein X is S(O), Y is O, and Z is CH$_2$.

In an embodiment, provided is a compound of formula (II), or a tautomer, stereoisomer, pharmaceutically acceptable salt, or solvate thereof, wherein X is S(O)$_2$, Y is O, and Z is CH$_2$.

In an embodiment, provided is a compound of formula (II), or a tautomer, stereoisomer, pharmaceutically acceptable salt, or solvate thereof, wherein X is S, Y is NH, and Z is CH$_2$.

In an embodiment, provided is a compound of formula (II), or a tautomer, stereoisomer, pharmaceutically acceptable salt, or solvate thereof, wherein X is S, Y is N(CH$_3$), and Z is CH$_2$.

In a preferred embodiment, provided is a compound of formula (II), or a tautomer, stereoisomer, pharmaceutically acceptable salt, or solvate thereof, wherein one of X and Y is S and the other is O.

In a more preferred embodiment, provided is a compound of formula (II) or a tautomer, stereoisomer, pharmaceutically acceptable salt, or solvate thereof, wherein X is S and Y is O.

According to embodiments of the application, ring B is an optionally substituted furanyl. Any positional or regioisomer of the furanyl ring can be used, meaning that the hydantoin moiety and X linker can be connected to the furanyl at any substitutable carbon atom on the furanyl ring. For example, the hydantoin moiety and X linker can be connected to the furanyl ring in a 2,3-substitution pattern, a 2,4-substitution pattern, a 2,5-substitution pattern, a 3,4-substitution pattern, etc., relative to the oxygen heteroatom of the furanyl ring.

In some embodiments, provided is a compound of formula (II), or a tautomer, stereoisomer, pharmaceutically acceptable salt, or solvate thereof, wherein ring B (i.e., the furanyl ring) is substituted. Ring B (i.e., the furanyl ring) can be substituted on any substitutable carbon atom of the furanyl ring. For example, ring B can be substituted with an alkyl group, e.g., methyl.

In some embodiments, provided is a compound of formula (II), or a tautomer, stereoisomer, pharmaceutically acceptable salt, or solvate thereof, wherein ring B is an unsubstituted furanyl ring.

In some embodiments, provided is a compound of formula (II), or a tautomer, stereoisomer, pharmaceutically acceptable salt, or solvate thereof, wherein ring B is furanyl substituted with —CH$_3$.

In an embodiment, provided is a compound of formula (III):

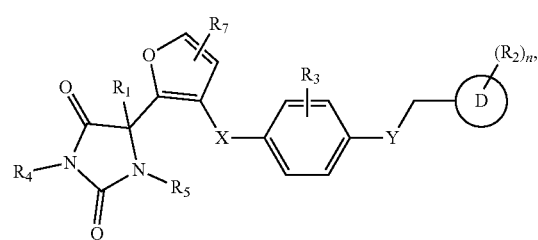

(III)

or a tautomer, stereoisomer, pharmaceutically acceptable salt, or solvate thereof, wherein R$_7$ is hydrogen or methyl; and the rest of the variable group are as defined above for the compound of formula (II).

In an embodiment, provided is a compound of formula (III), or a tautomer, stereoisomer, pharmaceutically acceptable salt, or solvate thereof, wherein R$_3$ is hydrogen, alkyl, or halo, preferably hydrogen, —CH$_3$, —F, or —Cl, more preferably hydrogen.

In an embodiment, provided is a compound of formula (III), or a tautomer, stereoisomer, pharmaceutically acceptable salt, or solvate thereof, wherein ring D is an optionally substituted phenyl, provided that (i) R$_1$ is alkyl; (ii) R$_2$ is not methoxy, chloro, or trifluoromethyl; and/or (iii) ring C is not unsubstituted phenyl.

In an embodiment, provided is a compound of formula (III), or a tautomer, stereoisomer, pharmaceutically acceptable salt, or solvate thereof, wherein ring D is an optionally substituted heteroaryl In an embodiment, provided is a compound of formula (III), or a tautomer, stereoisomer, pharmaceutically acceptable salt, or solvate thereof, wherein ring D is an optionally substituted pyridinyl or pyridinyl N-oxide.

In an embodiment, provided is a compound of formula (III), or a tautomer, stereoisomer, pharmaceutically acceptable salt, or solvate thereof, wherein ring D is optionally substituted with 1, 2, 3, 4, or 5 substitutent groups, preferably 1 or 2 substituent groups, independently selected from the group consisting of alkyl, halo, haloalkyl, alkoxy, alkylthio, amino, amide, alkylamino, aminoalkyl, cyano, hydroxyalkyl, —(CH$_2$)$_p$C(O)OR$_6$, and —(CH$_2$)$_p$OC(O)R$_6$, wherein p is 0, 1, 2, 3, 4, or 5. The substituent group, if present, can be attached at any position of ring D. Preferably, ring D is substituted with one substituent group (i.e., n is 1).

In an embodiment, provided is a compound of formula (III), or a tautomer, stereoisomer, pharmaceutically acceptable salt, or solvate thereof, wherein ring D is a monocyclic aryl or monocyclic heteroaryl group substituted with one substituent at the meta position, preferably phenyl or pyridinyl substituted at the meta position, relative to the bond to variable Z. Particularly preferred substituent groups for ring D include methyl (—CH$_3$), amide (—C(O)NH), methoxy (—OCH$_3$), hydroxyl (—OH), and hydroxylmethyl (—CH$_2$OH).

In a particular embodiment, ring D is phenyl.

In another particular embodiment, ring D is pyridinyl.

In another particular embodiment ring D is pyridinyl N-oxide.

In an embodiment, provided is a compound of formula (III), or a tautomer, stereoisomer, pharmaceutically acceptable salt, or solvate thereof, wherein n is 1 and R$_2$ is C$_{1-4}$ alkoxy (e.g., —OCH$_3$, —OCH$_2$CH$_2$CH$_3$, —OCH$_2$CH$_3$, —OCH(CH$_3$)$_2$, —OCH$_2$CH(CH$_3$)$_2$), C$_{1-4}$ alkyl (e.g., —CH$_3$, —CH$_2$CH$_3$, —CH$_2$CH(CH$_3$)$_2$), —CH$_2$OH, —OH, —COOH, —C(O)NH$_2$, —C(O)NHCH$_3$, or —CH$_2$OC(O)CH(NH$_2$)CH(CH$_3$)$_2$, —C(O)NH$_2$, —C(O)NHCH$_3$. Preferably R$_2$ is —CH$_3$, —C(O)NH$_2$, —CH$_2$OH, —OCH$_3$, or OH.

In an embodiment, provided is a compound of formula (III), or a tautomer, stereoisomer, pharmaceutically acceptable salt, or solvate thereof, wherein ring D is:

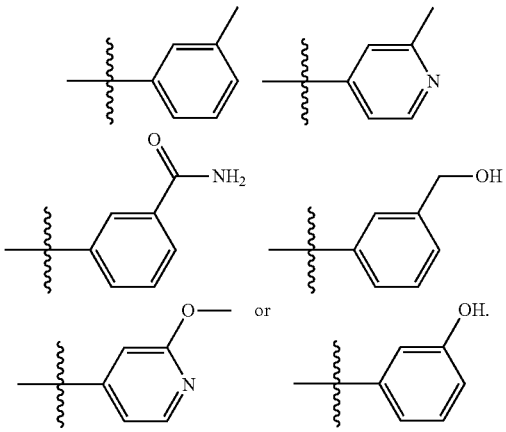

In an embodiment, provided is a compound of formula (III), or a tautomer, stereoisomer, pharmaceutically acceptable salt, or solvate thereof, wherein R$_1$ is hydrogen or C$_{1-4}$ alkyl.

In an embodiment, provided is a compound of formula (III), or a tautomer, stereoisomer, pharmaceutically acceptable salt, or solvate thereof, wherein R$_1$ is hydrogen, —CH$_3$, —CH$_2$CH$_3$, —CH$_2$CH$_2$CH$_3$, —CH(CH$_3$)$_2$, or —CH$_2$CH(CH$_3$)$_2$.

In an embodiment, provided is a compound of formula (III), or a tautomer, stereoisomer, pharmaceutically acceptable salt, or solvate thereof, wherein R$_1$ is hydrogen.

In an embodiment, provided is a compound of formula (III), or a tautomer, stereoisomer, pharmaceutically acceptable salt, or solvate thereof, wherein R$_4$ is hydrogen or —CH$_3$ and R$_5$ is —CH$_3$.

In an embodiment, provided is a compound of formula (III), or a tautomer, stereoisomer, pharmaceutically acceptable salt, or solvate thereof, wherein each of $R_4$ and $R_5$ is hydrogen.

In an embodiment, provided is a compound of formula (III), or a tautomer, stereoisomer, pharmaceutically acceptable salt, or solvate thereof, wherein each of X and Y is independently selected from the group consisting of O, $NR_x$, $CH_2$, and $S(O)_q$, wherein q is 0, 1, or 2 and $R_x$ is hydrogen or alkyl, e.g., methyl.

In an embodiment, provided is a compound of formula (III), or a tautomer, stereoisomer, pharmaceutically acceptable salt, or solvate thereof, wherein X is S.

In an embodiment, provided is a compound of formula (III), or a tautomer, stereoisomer, pharmaceutically acceptable salt, or solvate thereof, wherein X is S; and Y is O, $CH_2$, NH, or $NH(CH_3)$.

In an embodiment, provided is a compound of formula (III), or a tautomer, stereoisomer, pharmaceutically acceptable salt, or solvate thereof, wherein X is O and Y is O.

In an embodiment, provided is a compound of formula (III), or a tautomer, stereoisomer, pharmaceutically acceptable salt, or solvate thereof, wherein X is S and Y is S.

In an embodiment, provided is a compound of formula (III), or a tautomer, stereoisomer, pharmaceutically acceptable salt, or solvate thereof, wherein X is O and Y is S.

In an embodiment, provided is a compound of formula (III), or a tautomer, stereoisomer, pharmaceutically acceptable salt, or solvate thereof, wherein X is S and Y is O.

In an embodiment, provided is a compound of formula (III), or a tautomer, stereoisomer, pharmaceutically acceptable salt, or solvate thereof, wherein X is S(O) and Y is O.

In an embodiment, provided is a compound of formula (III), or a tautomer, stereoisomer, pharmaceutically acceptable salt, or solvate thereof, wherein X is $S(O)_2$ and Y is O.

In an embodiment, provided is a compound of formula (III), or a tautomer, stereoisomer, pharmaceutically acceptable salt, or solvate thereof, wherein X is S and Y is NH.

In an embodiment, provided is a compound of formula (III), or a tautomer, stereoisomer, pharmaceutically acceptable salt, or solvate thereof, wherein X is S and Y is $N(CH_3)$.

In a preferred embodiment, provided is a compound of formula (III), or a tautomer, stereoisomer, pharmaceutically acceptable salt, or solvate thereof, wherein one of X and Y is S and the other is O.

In a more preferred embodiment, provided is a compound of formula (III) or a tautomer, stereoisomer, pharmaceutically acceptable salt, or solvate thereof, wherein X is S and Y is O.

In an embodiment, provided is a compound of formula (III), or a tautomer, stereoisomer, pharmaceutically acceptable salt, or solvate thereof, wherein:

$R_1$ is hydrogen or $C_{1-4}$ alkyl;

X is S;

Y is O, $CH_2$, NH, or $N(CH_3)$;

each $R_2$ is independently selected from the group consisting of hydrogen, alkyl, hydroxyl, alkoxy, amide, and hydroxyalkyl;

each $R_3$ is hydrogen, alkyl or halo;

ring D is phenyl, pyridinyl, or pyridinyl N-oxide;

each of $R_4$ and $R_5$ is hydrogen;

$R_7$ is hydrogen or methyl; and n is 1 or 2.

In an embodiment, provided is a compound of formula (IV):

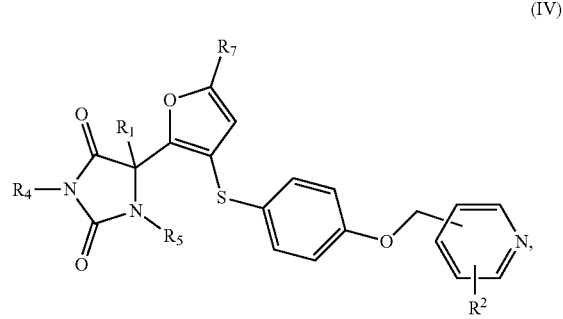

or a tautomer, stereoisomer, pharmaceutically acceptable salt, or solvate thereof, wherein $R_7$ is hydrogen or methyl; and the rest of the variable group are as defined above for the compound of formula (II) or formula (III).

In an embodiment, provided is a compound of formula (IV), or a tautomer, stereoisomer, pharmaceutically acceptable salt, or solvate thereof, wherein $R_2$ is $C_{1-4}$ alkoxy (e.g., —$OCH_3$, —$OCH_2CH_2CH_3$, —$OCH_2CH_3$, —$OCH(CH_3)_2$, —$OCH_2CH(CH_3)_2$), $C_{1-4}$ alkyl (e.g., —$CH_3$, —$CH_2CH_3$, —$CH_2CH(CH_3)_2$), —$CH_2OH$, —OH, —COOH, —C(O)$NH_2$, —C(O)$NHCH_3$, or —$CH_2OC(O)CH(NH_2)CH(CH_3)_2$, —C(O)$NH_2$, —C(O)$NHCH_3$.

In an embodiment, provided is a compound of formula (IV), or a tautomer, stereoisomer, pharmaceutically acceptable salt, or solvate thereof, wherein $R_2$ is —$CH_3$, $C_{1-4}$ alkoxy, —OH, —$CH_2OH$, or —C(O)$NH_2$. Preferably $R_2$ is —$CH_3$, —C(O)$NH_2$, —$CH_2OH$, —$OCH_3$, or OH.

In an embodiment, provided is a compound of formula (IV), or a tautomer, stereoisomer, pharmaceutically acceptable salt, or solvate thereof, wherein $R_1$ is $C_{1-4}$ alkyl.

In an embodiment, provided is a compound of formula (IV), or a tautomer, stereoisomer, pharmaceutically acceptable salt, or solvate thereof, wherein $R_1$ is hydrogen.

In an embodiment, provided is a compound of formula (IV), or a tautomer, stereoisomer, pharmaceutically acceptable salt, or solvate thereof, wherein $R_4$ is hydrogen or —$CH_3$ and $R_5$ is —$CH_3$.

In an embodiment, provided is a compound of formula (IV), or a tautomer, stereoisomer, pharmaceutically acceptable salt, or solvate thereof, wherein each of $R_4$ and $R_5$ is hydrogen.

In an embodiment, provided is a compound of formula (IV), or a tautomer, stereoisomer, pharmaceutically acceptable salt, or solvate thereof, wherein:

$R_1$ is hydrogen or alkyl;

$R_2$ is selected from the group consisting of alkyl, amide, hydroxyl, alkoxy, and hydroxylalkyl;

each of $R_4$ and $R_5$ is hydrogen; and $R_7$ is methyl or hydrogen.

In an embodiment, provided is a compound of formula (V):

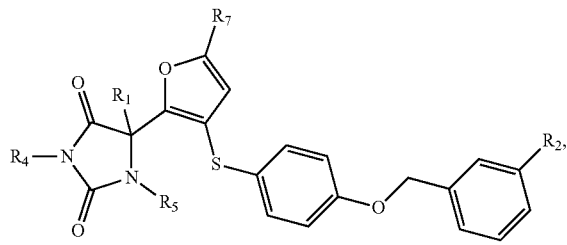

or a tautomer, stereoisomer, pharmaceutically acceptable salt, or solvate thereof,
wherein $R_7$ is hydrogen or methyl; and the rest of the variable group are as defined above for the compound of formula (II) or formula (III).

In an embodiment, provided is a compound of formula (V), or a tautomer, stereoisomer, pharmaceutically acceptable salt, or solvate thereof, wherein $R_2$ is $C_{1-4}$ alkoxy (e.g., —OCH$_3$, —OCH$_2$CH$_2$CH$_3$, —OCH$_2$CH$_3$, —OCH(CH$_3$)$_2$, —OCH$_2$CH(CH$_3$)$_2$), $C_{1-4}$ alkyl (e.g., —CH$_3$, —CH$_2$CH$_3$, —CH$_2$CH(CH$_3$)$_2$), —CH$_2$OH, —OH, —COOH, —C(O)NH$_2$, —C(O)NHCH$_3$, or —CH$_2$OC(O)CH(NH$_2$)CH(CH$_3$)$_2$, —C(O)NH$_2$, —C(O)NHCH$_3$.

In an embodiment, provided is a compound of formula (V), or a tautomer, stereoisomer, pharmaceutically acceptable salt, or solvate thereof, wherein $R_2$ is —CH$_3$, $C_{1-4}$ alkoxy, —OH, —CH$_2$OH, or —C(O)NH$_2$. Preferably $R_2$ is —CH$_3$, —C(O)NH$_2$, —CH$_2$OH, —OCH$_3$, or OH.

In an embodiment, provided is a compound of formula (V), or a tautomer, stereoisomer, pharmaceutically acceptable salt, or solvate thereof, wherein $R_1$ is $C_{1-4}$ alkyl.

In an embodiment, provided is a compound of formula (V), or a tautomer, stereoisomer, pharmaceutically acceptable salt, or solvate thereof, wherein $R_1$ is hydrogen.

In an embodiment, provided is a compound of formula (V), or a tautomer, stereoisomer, pharmaceutically acceptable salt, or solvate thereof, wherein $R_4$ is hydrogen or —CH$_3$ and $R_5$ is —CH$_3$.

In an embodiment, provided is a compound of formula (V), or a tautomer, stereoisomer, pharmaceutically acceptable salt, or solvate thereof, wherein each of $R_4$ and $R_5$ is hydrogen.

In an embodiment, provided is a compound of formula (V), or a tautomer, stereoisomer, pharmaceutically acceptable salt, or solvate thereof, wherein:
$R_1$ is alkyl;
$R_2$ is selected from the group consisting of alkyl, amide, alkoxy, hydroxyl, and hydroxyalkyl;
each of $R_4$ and $R_5$ is hydrogen; and
$R_7$ is methyl or hydrogen.

Exemplary compounds of the application include, but are not limited to, compounds listed in Table 1 below, and any tautomer, stereoisomer, pharmaceutically acceptable salt or solvate thereof. The MMP-12 IC$_{50}$ values were determined according to the assay described in Example 1 below. The IC$_{50}$ values are reported as follows: A=less than 10 nM, B=10 nM to 100 nM, C=100 nM to 1000 nM D=greater than 1000 nM.

TABLE 1

Exemplary Compounds of the Application

| Compound ID | Structure | Analytical Data (LCMS, NMR, etc.) | MMP-12 IC$_{50}$ (nM) |
|---|---|---|---|
| FC-1 | 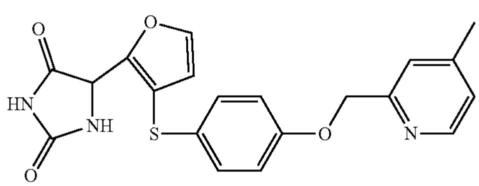 [SMILES: Cc1ccnc(COc2ccc(Sc3ccoc3C3NC(=O)NC3=O)cc2)c1] | 1H NMR (400 MHZ, CD3OD) δ 8.36 (d, J = 5.2 Hz, 1H), 7.57 (d, J = 1.9 Hz, 1H), 7.42 (s, 1H), 7.30 (d, J = 8.9 Hz, 2H), 7.21 (d, J = 5.5 Hz, 1H), 6.95 (d, J = 8.9 Hz, 2H), 6.39 (d, J = 1.9 Hz, 1H), 5.51 (s, 1H), 5.11 (s, 2H), 2.39 (s, 3H); m/z (ESI+) (M + H)+ = 396.35; HPLC tR = 5.366 min. | C |
| FC-2 | 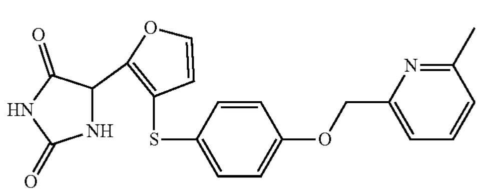 [SMILES: Cc1cccc(COc2ccc(Sc3ccoc3C3NC(=O)NC3=O)cc2)n1] | 1H NMR (400 MHZ, DMSO-d6) δ 11.01-10.93 (m, 1H), 8.37-8.32 (m, 1H), 7.80-7.74 (m, 1H), 7.73-7.64 (m, 1H), 7.30-7.22 (m, 2H), 7.21-7.14 (m, 1H), 7.00-6.92 (m, 2H), 6.51-6.44 (m, 1H), 5.45 (s, 1H), 5.09 (s, 2H), 2.45 (s, 3H); m/z (ESI+) (M + H)+ = 396.10; HPLC tR = 5.404 min. | B |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| FC-3 | 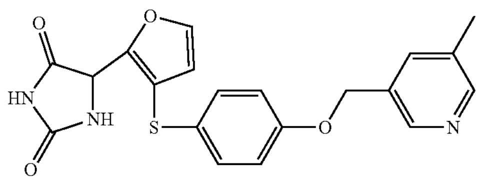 [SMILES: Cc1cncc(COc2ccc(Sc3ccoc3C3NC(=O)NC3=O)cc2)c1] | 1H NMR (400 MHZ, CD3OD) δ 8.40 (s, 1H), 8.33 (s, 1H), 7.75 (s, 1H), 7.57 (d, J = 1.9 Hz, 1H), 7.33(s, 1H), 7.31 (d, J = 8.9 Hz, 2H), 6.96 (d, J = 8.8 Hz, 2H), 6.39 (d, J = 1.9 Hz, 1H), 5.51 (s, 1H), 5.09 (s, 2H), 2.37 (s, 3H); m/z (ESI+) (M + H)+ = 396.20; HPLC tR = 5.509 min. | B |
| FC-4 | 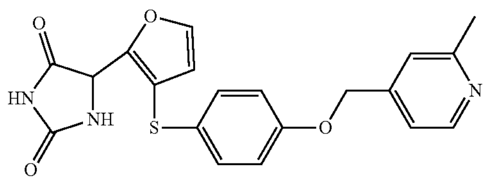 [SMILES: Cc1cc(COc2ccc(Sc3ccoc3C3NC(=O)NC3=O)cc2)ccn1] | 1H NMR (400 MHZ, CD3OD) δ 8.63 (d, J = 6.2 Hz, 1H), 7.93 (s, 1H), 7.87 (d, J = 6.7 Hz, 1H), 7.59 (d, J = 1.9 Hz, 1H), 7.33 (d, J = 8.9 Hz, 2H), 7.00 (d, J = 8.9 Hz, 2H), 6.41 (d, J = 1.9 Hz, 1H), 5.51 (s, 1H), 5.35 (d, J = 9.1 Hz, 2H), 2.77 (s, 3H); m/z (ESI+) (M + H)+ = 396.80; HPLC tR = 5.297 min. | A |
| FC-5 | 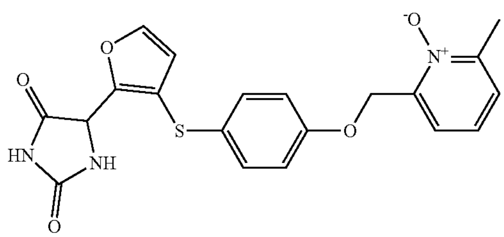 | 1H NMR (400 MHZ, DMSO-d6) δ 8.35 (s, 1H), 7.78 (d, J = 1.9 Hz, 1H), 7.44 (dd, J = 24.7, 7.6 Hz, 2H), 7.27 (d, J = 8.9 Hz, 3H), 7.00 (d, J = 8.9 Hz, 2H), 6.50 (d, J = 1.9 Hz, 1H), 5.45 (s, 1H), 5.22 (s, 2H), 2.39 (s, 3H); m/z (ESI+) (M + H)+ = 412.15; HPLC tR = 6.140 min. | D |
| FC-6 | 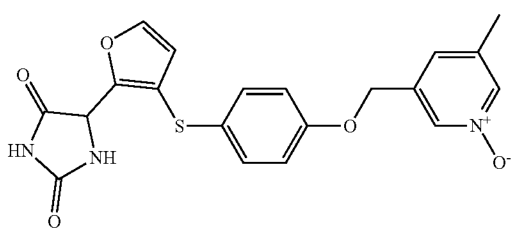 [SMILES: Cc1cc(COc2ccc(Sc3ccoc3C3NC(=O)NC3=O)cc2)c[n+]([O-])c1] | 1H NMR (400 MHZ, DMSO-d6) δ 8.35 (s, 1H), 8.11 (s, 1H), 8.07 (s, 1H), 7.77 (d, J = 1.9 Hz, 1H), 7.29-7.20 (m, 3H), 6.98 (d, J = 8.8 Hz, 2H), 6.48 (d, J = 1.9 Hz, 1H), 5.45 (s, 1H), 5.04 (s, 2H), 2.23 (s, 3H); m/z (ESI+) (M + H)+ = 412.10; HPLC tR = 5.822 min. | C |
| FC-7 | 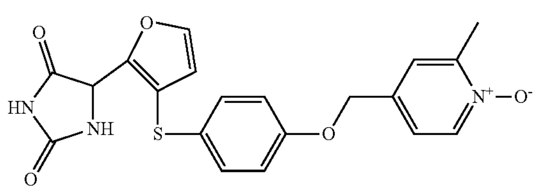 [SMILES: Cc1cc(COc2ccc(Sc3ccoc3C3NC(=O)NC3=O)cc2)cc[n+]1[O-]] | 1H NMR (400 MHZ, CD3OD) δ 8.33 (d, J = 6.6 Hz, 1H), 7.61 (s, 1H), 7.56 (s, 1H), 7.51-7.44 (m, 1H), 7.29 (d, J = 8.9 Hz, 2H), 6.94 (d, J = 8.9 Hz, 2H), 6.38 (d, J = 2.0 Hz, 1H), 5.50 (s, 1H), 5.12 (s, 2H), 2.53 (s, 3H); m/z (ESI+) (M + H)+ = 412.10; HPLC tR = 5.759 min. | B |
| FC-8 | 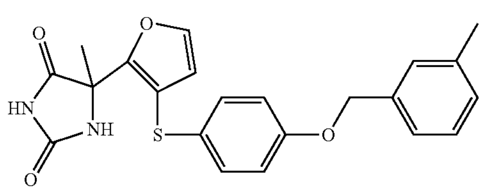 [SMILES: Cc1cccc(COc2ccc(Sc3ccoc3C3(C)NC(=O)NC3=O)cc2)c1] | 1H NMR (400 MHZ, CDCl3) δ 9.57 (s, 1H), 7.32 (d, J = 1.9 Hz, 1H), 7.23 (s, 1H), 7.20-7.13 (m, 4H), 7.13-7.07 (m, 1H), 6.95 (s, 1H), 6.85 (d, J = 8.9 Hz, 2H), 6.22 (d, J = 1.9 Hz, 1H), 2.33 (s, 3H), 1.85 (s, 3H); m/z (ESI+) (M + H)+ = 409.15; HPLC tR = 7.276 min. | A |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| FC-9 | 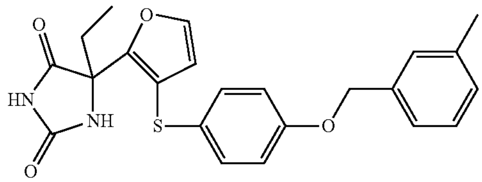 [SMILES: CCC1(c2occc2Sc2ccc(OCc3cccc(C)c3)cc2)NC(=O)NC1=O] | 1H NMR (400 MHZ, CDCl3) δ 9.00 (s, 1H), 7.37-7.30 (m, 1H), 7.27-7.15 (m, 5H), 7.12 (d, J = 7.4 Hz, 1H), 6.89-6.82 (m, 2H), 6.61 (s, 1H), 6.24-6.19 (m, 1H), 4.93 (d, J = 21.2 Hz, 2H), 4.76 (d, J = 22.5 Hz, 1H), 2.34 (s, 3H), 2.28 (dd, J = 15.2, 7.5 Hz, 2H), 1.00-0.91 (m, 3H); m/z (ESI+) (M + H)+ = 423.10; HPLC tR = 7.581 min. | B |
| FC-10 | 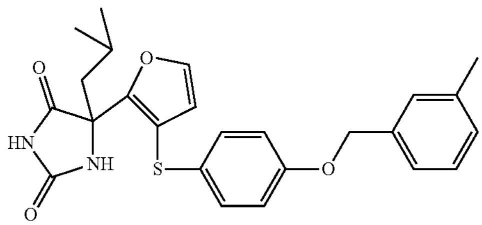 [SMILES: Cc1cccc(COc2ccc(Sc3ccoc3C3(CC(C)C)NC(=O)NC3=O)cc2)c1] | 1H NMR (400 MHZ, CDCl3) δ 8.66 (s, 1H), 7.44-7.30 (m, 1H), 7.25 (dd, J = 8.3, 6.7 Hz, 1H), 7.19 (dd, J = 10.3, 3.2 Hz, 4H), 7.13 (d, J = 7.3 Hz, 1H), 6.89-6.85 (m, 2H), 6.57 (s, 1H), 6.21 (t, J = 1.7 Hz, 1H), 4.97 (s, 2H), 2.39-2.32 (m, 3H), 2.05 (ddd, J = 14.8, 13.9, 5.8 Hz, 2H), 1.75-1.71 (m, 1H), 0.98-0.80 (m, 6H); m/z (ESI+) (M + H)+ = 451.30; HPLC tR = 7.759 min. | A |
| FC-11 | 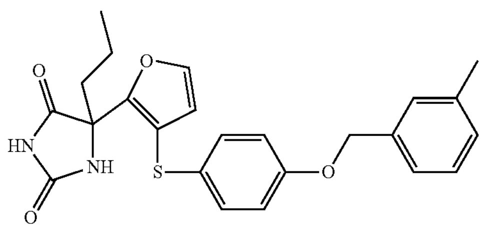 [SMILES: CCCC1(c2occc2Sc2ccc(OCc3cccc(C)c3)cc2)NC(=O)NC1=O] | 1H NMR (400 MHZ, CDCl3) δ 7.36 (dd, J = 1.9, 1.4 Hz, 1H), 7.25 (t, J = 4.2 Hz, 2H), 7.22-7.15 (m, 4H), 7.12 (d, J = 7.4 Hz, 1H), 6.87 (dd, J = 7.2, 1.7 Hz, 2H), 6.30 (s, 1H), 6.24 (dd, J = 1.9, 1.4 Hz, 1H), 4.96 (s, 2H), 2.35 (s, 3H), 2.28-2.18 (m, 2H), 1.50-1.39 (m, 1H), 0.96 (t, J = 7.3 Hz, 3H); m/z (ESI+) (M + H)+ = 437.10; HPLC tR = 7.702 min. | A |
| FC-12 | 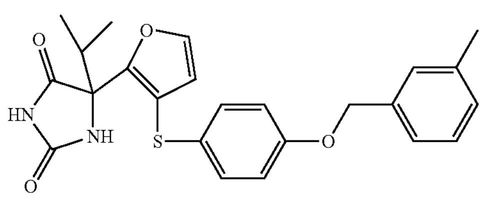 [SMILES: Cc1cccc(COc2ccc(Sc3ccoc3C3(C(C)C)NC(=O)NC3=O)cc2)c1] | 1H NMR (400 MHZ, CDCl3) δ 8.60 (s, 1H), 7.38 (t, J = 1.4 Hz, 1H), 7.26 (dd, J = 7.8, 7.1 Hz, 1H), 7.23-7.16 (m, 4H), 7.13 (d, J = 7.4 Hz, 1H), 6.92-6.84 (m, 2H), 6.67 (s, 1H), 6.21 (d, J = 1.9 Hz, 1H), 4.97 (s, 2H), 2.97-2.88 (m, 1H), 2.36 (s, 3H), 0.98 (d, J = 6.7 Hz, 3H), 0.90 (d, J = 6.8 Hz, 3H); m/z (ESI+) (M + H)+ = 437.30; HPLC tR = 7.759 min. | A |
| FC-13 | 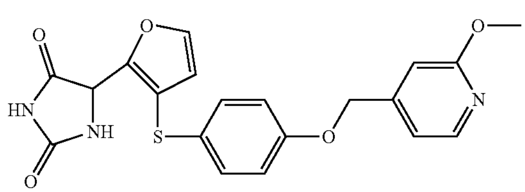 [SMILES: COc1cc(COc2ccc(Sc3ccoc3C3NC(=O)NC3=O)cc2)ccn1] | 1H NMR (400 MHZ, DMSO-d6) δ 8.36 (s, 1H), 8.13 (d, J = 5.2 Hz, 1H), 7.77 (d, J = 1.9 Hz, 1H), 7.25 (d, J = 8.5 Hz, 2H), 6.97 (dd, J = 10.3, 7.0 Hz, 4H), 6.81 (s, 1H), 6.48 (d, J = 1.8 Hz, 1H), 5.44 (s, 1H), 5.11 (s, 3H), 3.82 (s, 4H); m/z (ESI+) (M + H)+ = 412.2; HPLC tR = 6.299 min. | B |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| FC-14 | 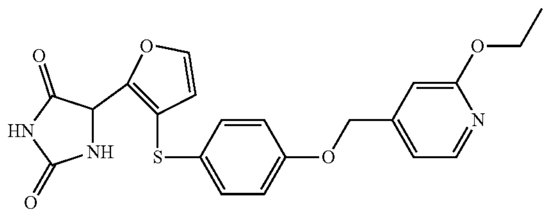 [SMILES: CCOc1cc(COc2ccc(Sc3ccoc3C3NC(=O)NC3=O)cc2)ccn1] | 1H NMR (400 MHZ, CDCl3) δ 8.26 (s, OH), 8.12 (d, J = 5.2 Hz, 1H), 7.43 (s, 1H), 7.23 (d, J = 8.7 Hz, 2H), 6.86 (d, J = 8.1 Hz, 3H), 6.76 (s, 1H), 6.37 (s, 1H), 5.76 (s, 1H), 5.48 (s, 1H), 4.99 (s, 2H), 4.35 (q, J = 7.0 Hz, 2H), 1.38 (t, J = 7.0 Hz, 3H); m/z (ESI+) (M + H)+ = 426.2; HPLC tR = 6.356 min. | B |
| FC-15 | 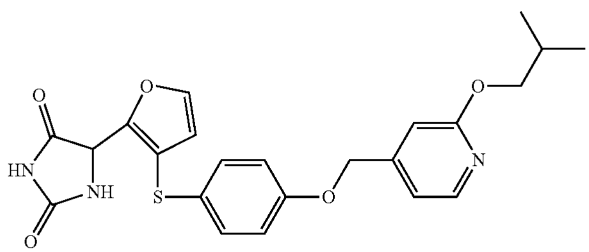 [SMILES: CC(C)COc1cc(COc2ccc(Sc3ccoc3C3NC(=O)NC3=O)cc2)ccn1] | 1H NMR (400 MHZ, DMSO-d6) δ 8.34 (s, 1H), 8.10 (d, J = 5.2 Hz, 1H), 7.77 (s, 1H), 7.26 (d, J = 8.6 Hz, 2H), 6.97 (d, J = 9.0 Hz, 4H), 6.80 (s, 1H), 6.48 (s, 1H), 5.45 (s, 1H), 5.10 (s, 2H), 4.00 (d, J = 6.6 Hz, 2H), 2.05-1.92 (m, 1H), 0.94 (d, J = 6.7 Hz, 7H); m/z (ESI+) (M + H)+ = 454.1; HPLC tR = 7.191 min. | C |
| FC-16 | 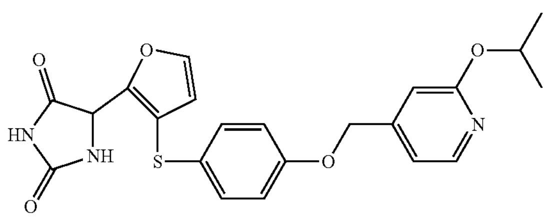 [SMILES: CC(C)Oc1cc(COc2ccc(Sc3ccoc3C3NC(=O)NC3=O)cc2)ccn1] | 1H NMR (400 MHZ, DMSO-d6) δ 8.36 (s, 1H), 8.10 (d, J = 5.2 Hz, 1H), 7.77 (d, J = 2.0 Hz, 1H), 7.32-7.21 (m, 2H), 6.98-6.94 (m, 2H), 6.93 (dd, J = 5.3, 1.3 Hz, 1H), 6.72 (s, 1H), 6.48 (d, J = 2.0 Hz, 1H), 5.45 (d, J = 1.0 Hz, 1H), 5.27-5.14 (m, 1H), 5.09 (s, 2H), 1.25 (d, J = 6.2 Hz, 6H); m/z (ESI+) (M + H)+ = 440.15; HPLC tR = 5.893 min. | C |
| FC-17 | 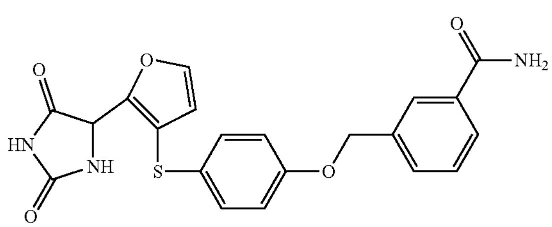 [SMILES: NC(=O)c1cccc(COc2ccc(Sc3ccoc3C3NC(=O)NC3=O)cc2)c1] | 1H NMR (400 MHZ, DMSO-d6) δ 10.98 (s, 1H), 8.36 (s, 1H), 8.00 (s, 1H), 7.93 (s, 1H), 7.80 (s, 1H), 7.77 (d, J = 1.8 Hz, 1H), 7.55 (s, 1H), 7.44 (s, 1H), 7.37 (s, 1H), 7.26 (d, J = 8.8 Hz, 2H), 6.98 (d, J = 8.8 Hz, 2H), 6.48 (d, J = 1.9 Hz, 1H), 5.45 (s, 1H), 5.11 (s, 2H); m/z (ESI+) (M + H)+ = 424.15; HPLC tR = 5.827 min. | A |
| FC-18 | 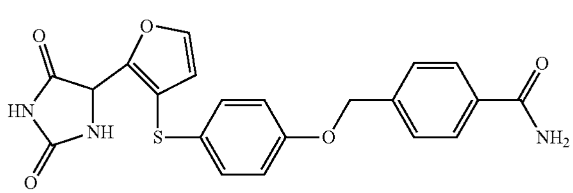 [SMILES: NC(=O)c1ccc(COc2ccc(Sc3ccoc3C3NC(=O)NC3=O)cc2)cc1] | 1H NMR (400 MHZ, DMSO-d6) δ 8.35 (s, 1H), 7.96 (s, 1H), 7.86 (d, J = 8.1 Hz, 2H), 7.77 (d, J = 1.9 Hz, 1H), 7.47 (d, J = 8.0 Hz, 2H), 7.34 (s, 1H), 7.26 (d, J = 8.5 Hz, 2H), 6.97 (d, J = 8.6 Hz, 2H), 6.48 (d, J = 1.9 Hz, 1H), 5.45 (s, 1H), 5.14 (s, 2H); m/z (ESI+) (M + H)+ = 424.15; HPLC tR = 6.237 min. | B |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| FC-19 | 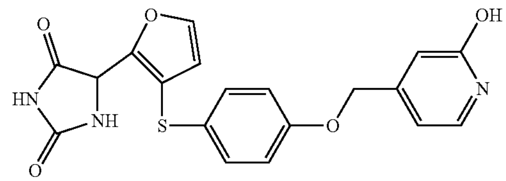 [SMILES: O=C1NC(=O)C(c2occc2Sc2ccc(OCc3ccnc(O)c3)cc2)N1] | 1H NMR (400 MHZ, DMSO-d6) δ 8.35 (s, 1H), 7.77 (d, J = 1.9 Hz, 1H), 7.34 (d, J = 6.8 Hz, 1H), 7.26 (d, J = 8.6 Hz, 2H), 6.95 (d, J = 8.7 Hz, 3H), 6.49 (d, J = 1.8 Hz, 1H), 6.30 (s, 1H), 6.14 (d, J = 6.7 Hz, 1H), 5.45 (s, 1H), 4.95 (s, 2H); m/z (ESI+) (M + H)+ = 398.05; HPLC tR = 5.640 min. | |
| FC-20 | 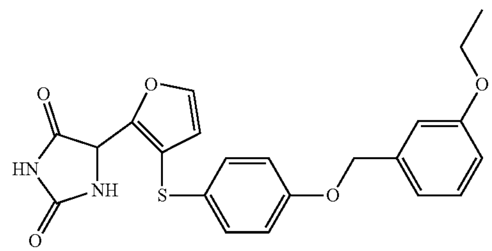 [SMILES: CCOc1cccc(COc2ccc(Sc3ccoc3C3NC(=O)NC3=O)cc2)c1] | 1H-NMR (300 MHZ CDCl3) δ: 8.052 (bs, 1H), 7.409 (s, 1H), 7.282-7.207 (m, 3H), 6.953-6.816 (m, 5H), 6.358 (s, 1H), 5.637 (bs, 1H), 5.466 (s, 1H), 4.981 (s, 2H), 4.016 (q, J = 6.9 Hz, 2H), 1.389 (t, J = 6.9 Hz, 3H); m/z (ESI+) 422.98 (M−); HPLC tR: 5.645 min. | C |
| FC-21 | 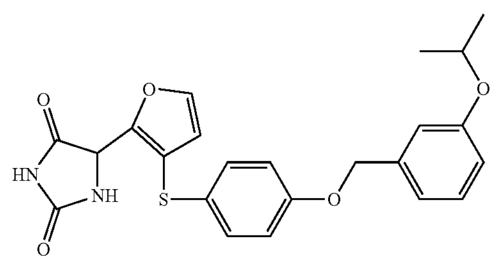 [SMILES: CC(C)Oc1cccc(COc2ccc(Sc3ccoc3C3NC(=O)NC3=O)cc2)c1] | 1H-NMR (300 MHz DMSO) δ: 8.379 (bs, 1H), 7.761 (d, J = 2.1 Hz, 1H), 7.283-7.231 (m, 3H), 6.976-6.923 (m, 5H), 6.827 (bs, 1H), 6.470 (d, J = 2.1 Hz, 1H), 5.454 (s, 1H), 5.032 (s, 2H), 4.581 (qq, J = 6.0 Hz, 1H), 1.230 (d, J = 6.0 Hz, 6H); m/z (ESI+) 437.03 (M−); HPLC tR: 6.491 min. | C |
| FC-22 | 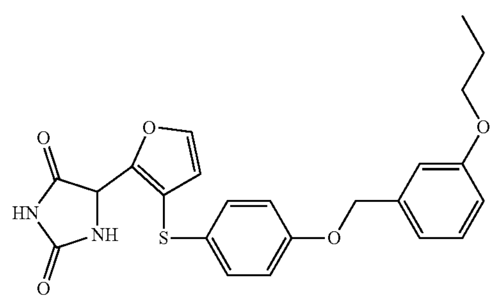 [SMILES: CCCOc1cccc(COc2ccc(Sc3ccoc3C3NC(=O)NC3=O)cc2)c1] | 1H-NMR (300 MHz CDCl3) δ: 7.706 (bs, 1H), 7.363 (d, J = 2.1 Hz, 1H), 7.233-7.158 (m, 3H), 6.901-6.771 (m, 5H), 6.311 (d, J = 2.1 Hz, 1H), 5.425 (s, 2H), 4.931 (s, 2H), 3.854 (t, J = 6.3 Hz, 2H), 1.735 (tq, J = 7.1 Hz, 2H), 0.858 (t, J = 7.1 Hz, 3H); m/z (ESI+) 437.02 (M−); HPLC tR: 7.914 min. | D |
| FC-23 | 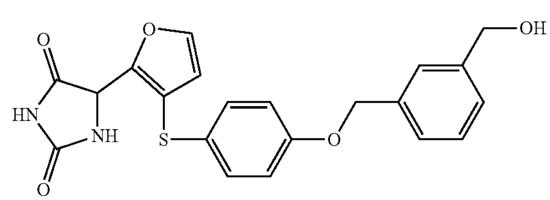 [SMILES: O=C1NC(=O)C(c2occc2Sc2ccc(OCc3cccc(CO)c3)cc2)N1] | 1H-NMR (300 MHz CDCl3) δ: 7.565 (d, J = 2.1 Hz, 1H), 7.419 (bs, 1H), 7.325-7.272 (m, 6H), 6.943-6.914 (m, 2H), 6.383 (d, J = 2.1 Hz, 1H), 5.514 (s, 1H), 5.061 (s, 1H), 4.603 (s, 2H); m/z (ESI+) 408.99 (M−); HPLC tR: 5.675 min. | A |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| FC-24 | 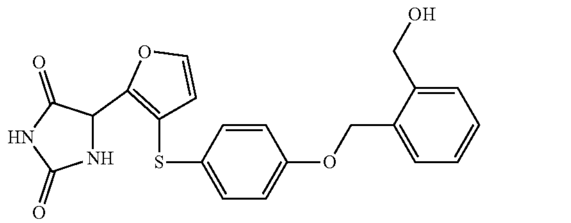 [SMILES: O=C1NC(=O)C(c2occc2Sc2ccc(OCc3ccccc3CO)cc2)N1] | 1H-NMR (300 MHz DMSO) δ: 8.335 (bs, 1H), 7.785 (d, J = 2.1 Hz, 1H), 7.471-7.390 (m, 2H), 7.348-7.265 (m, 4H), 7.007-6.978 (m, 2H), 6.503 (d, J = 2.1 Hz, 1H), 5.456 (s, 1H), 5.125 (s, 2H), 4.580 (s, 2H), 1.987 (s, 1H, OH); m/z (ESI+) 408.97 (M−); HPLC tR: 5.873 min. | A |
| FC-25 | 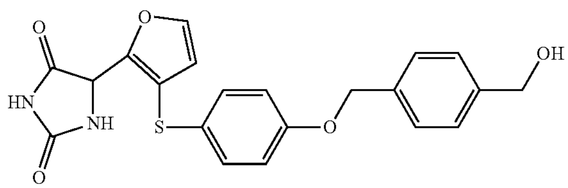 [SMILES: O=C1NC(=O)C(c2occc2Sc2ccc(OCc3ccc(CO)cc3)cc2)N1] | 1H-NMR (300 MHz DMSO) δ: 8.342 (bs, 1H), 7.780 (d, J = 2.1 Hz, 1H), 7.390-7.249 (m, 6H), 6.984-6.955 (m, 2H), 6.490 (d, J = 2.1 Hz, 1H), 5.455 (s, 1H), 5.064 (s, 2H), 4.486 (d, J = 6.3 Hz, 2H), 1.987 (s, 1H, OH); m/z (ESI+) 408.97 (M−); HPLC tR: 5.044 min. | A |
| FC-26 | 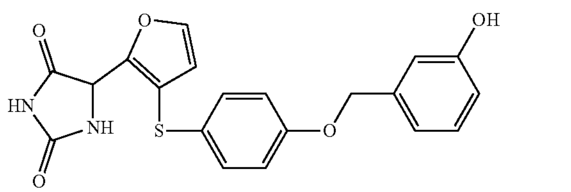 [SMILES: O=C1NC(=O)C(c2occc2Sc2ccc(OCc3cccc(O)c3)cc2)N1] | 1H-NMR (300 MHz DMSO) δ: 11.056 (bs, 1H), 9.463 (bs, 1H), 8.349 (bs, 1H), 7.780 (d, J = 2.1 Hz, 1H), 7.266 (d, J = 8.7 Hz, 2H), 7.185-7.132 (m, 1H), 6.958 (d, J = 8.7 Hz, 2H), 6.820 (d, J = 7.8 Hz, 2H), 6.696 (d, J = 8.7 Hz, 2H), 6.493 (d, J = 2.1 Hz, 2H), 5.456 (s, 1H), 5.004 (s, 2H); m/z (ESI+) 394.92 (M−); HPLC tR: 5.898 min. | A |
| FC-27 | 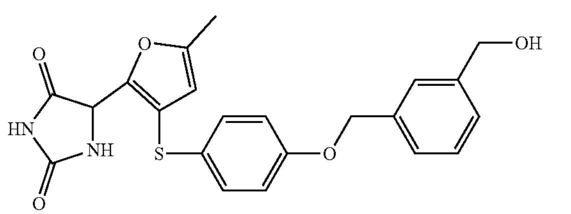 [SMILES: Cc1cc(Sc2ccc(OCc3cccc(CO)c3)cc2)c(C2NC(=O)NC2=O)o1] | 1H-NMR (300 MHZ CDCl3) δ: 7.422 (s, 1H), 7.325-7.257 (m, 5H), 6.920 (d, J = 8.4 Hz, 2H), 5.983 (s, 1H), 5.456 (s, 1H), 5.059 (s, 2H), 4.606 (s, 2H), 2.007 (s, 3H); m/z (ESI+) 423.20 (M_); HPLC tR: 3.468 min. | A |
| FC-28 | 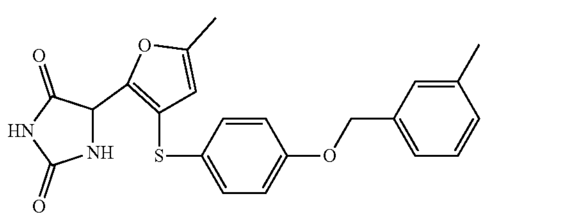 [SMILES: Cc1cccc(COc2ccc(Sc3cc(C)oc3C3NC(=O)NC3=O)cc2)c1] | 1H-NMR (300 MHz CDCl3) δ: 7.295-7.133 (m, 6H), 6.922 (d, J = 8.4 Hz, 2H), 5.993 (s, 1H), 5.464 (s, 1H), 5.018 (s, 2H), 2.344 (s, 3H), 2.249 (s, 3H); m/z (ESI+) 407.20 (M ); HPLC tR: 7.025 min. | B |
| FC-29 | 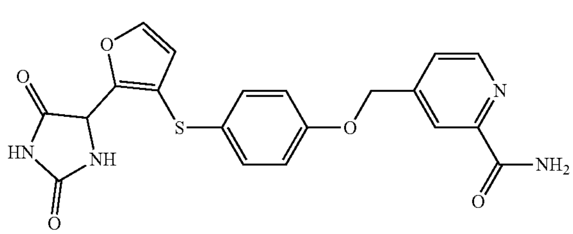 [SMILES: NC(=O)c1cc(COc2ccc(Sc3ccoc3C3NC(=O)NC3=O)cc2)ccn1] | 1H NMR (400 MHZ, CD3OD) δ: 8.599 (d, J = 5.2 Hz, 1H), 8.154 (s, 1H), 7.594 (d, J = 5.2 Hz, 1H), 7.559 (d, J = 2 Hz, 1H), 7.304 (d, J = 8.8 Hz, 2H), 6.964 (d, J = 8.4 Hz, 2H), 6.382 (d, J = 6.0 Hz, 1H), 5.497 (s, 1H), 5.197 (s, 1H); m/z (ESI+) (M + H)+ = 425.25, (M − H)− = 423.25; HPLC tR = 6.135 min. | B |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| FC-30 | 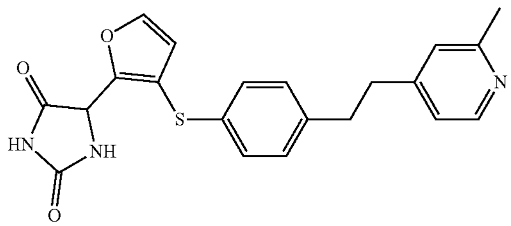 [SMILES: Cc1cc(CCc2ccc(Sc3ccoc3C3NC(=O)NC3=O)cc2)ccn1] | 1H NMR (400 MHZ, CD3OD) δ: 8.231 (d, J = 4.0 Hz, 1H), 7.602 (d, J = 2.0 Hz, 1H), 7.157-7.040 (m, 7H), 6.404 (d, J = 2.0 Hz, 1H), 5.471 (s, 1H), 2.884 (s, 4H), 2.451 (s, 3H); m/z (ESI+) (M + H)+ = 394.10, (M − H)− = 392.05; HPLC tR = 4.678 min. | B |
| FC-31 | 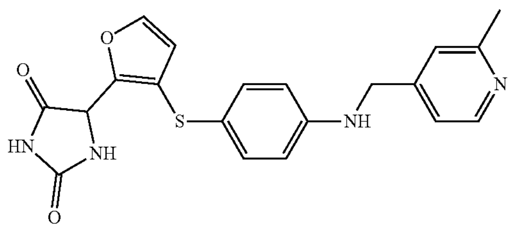 [SMILES: Cc1cc(CNc2ccc(Sc3ccoc3C3NC(=O)NC3=O)cc2)ccn1] | 1H NMR (400 MHZ, CD3OD) δ: 8.275 (d, J = 5.2 Hz, 1H), 7.466 (d, J = 2.0 Hz, 1H), 7.259 (s, 1H), 7.194-7.136 (m, 3H), 6.498 (d, J = 8.8 Hz, 2H), 6.291 (d, J = 1.6 Hz, 1H), 5.460 (s, 1H), 4.324 (s, 2H), 2.465 (s, 3H); m/z (ESI+) (M + H)+ = 395.20, (M − H)− = 391.15; HPLC tR = 4.642 min. | B |
| FC-32 | 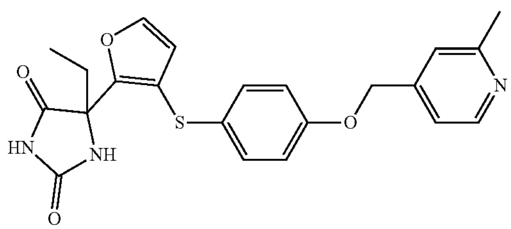 [SMILES: CCC1(c2occc2Sc2ccc(OCc3ccnc(C)c3)cc2)NC(=O)NC1=O] | 1H-NMR (400 MHZ DMSO) δ: 10.950 (s, 1H), 8.431 (s, 1H), 8.404 (d, J = 5.2 Hz, 1H), 7.711 (d, J = 2.0 Hz, 1H), 7.252-7.173 (m, 4H), 6.967 (d, J = 8.8 Hz, 2H), 6.348 (d, J = 2.0 Hz, 1H), 5.088 (s, 2H), 2.436 (s, 3H), 2.158-2.131 (m, 2H), 0.864-0.827 (m, 3H); m/z (ESI+) (M + H)+ = 424.15, (M − H)− = 422.10; HPLC tR = 5.556 min. | A |
| FC-33 | 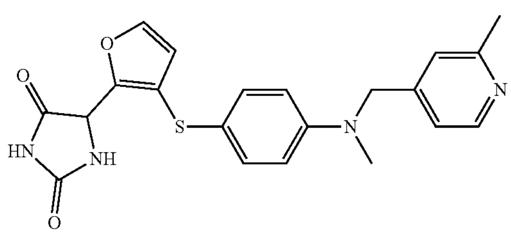 [SMILES: Cc1cc(CN(C)c2ccc(Sc3ccoc3C3NC(=O)NC3=O)cc2)ccn1] | 1H NMR (400 MHZ, CD3OD) δ: 8.275 (d, J = 5.6 Hz, 1H), 7.490 (d, J = 2.0 Hz, 1H), 7.245 (d, J = 9.2 Hz, 2H), 7.118 (s, 1H), 7.052 (d, J = 5.6 Hz, 1H), 6.640 (d, J = 8.8 Hz, 2H), 6.315 (d, J = 2.0 Hz, 1H), 5.481 (s, 1H), 4.552 (s, 3H), 3.052 (s, 3H), 2.456 (s, 3H); m/z (ESI+) (M + H)+ = 409.15, (M − H)− = 407.05; HPLC tR = 5.124 min. | D |
| FC-34 | 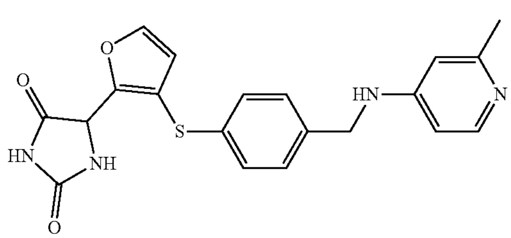 [SMILES: Cc1cc(NCc2ccc(Sc3ccoc3C3NC(=O)NC3=O)cc2)ccn1] | 1H NMR (400 MHZ, CDCl3) δ: 8.090 (d, J = 7.2 Hz, 1H), 7.669 (d, J = 2.0 Hz, 1H), 7.276 (d, J = 8.4 Hz, 2H), 6.763-6.711 (m, 2H), 6.469 (d, J = 2.0 Hz, 1H), 5.465 (s, 1H), 5.336 (s, 2H), 2.409 (s, 3H); m/z (ESI+) (M + H)+ = 395.25, (M − H)− = 393.15; HPLC tR = 4.990 min. | C |

TABLE 1-continued

Exemplary Compounds of the Application

| Compound ID | Structure | Analytical Data (LCMS, NMR, etc.) | MMP-12 IC$_{50}$ (nM) |
|---|---|---|---|
| FC-35 | 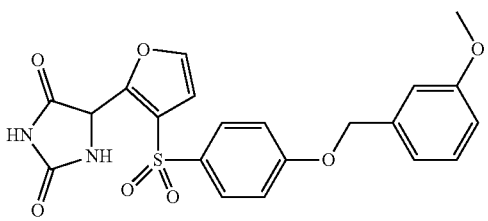 [SMILES: COc1cccc(COc2ccc(S(=O)(=O)c3ccoc3C3NC(=O)NC3=O)cc2)c1] | | |

Compounds of the application can be prepared by any number of processes as described generally below and more specifically illustrated by the exemplary examples which follow herein. For example, compounds of the application can be prepared according to any one of General Preparation Schemes 1 to 3. One of ordinary skill in the art will recognize that General Preparation Schemes 1 to 3 can be modified according to the exemplary examples and general knowledge in the art in order to obtain compounds of the application.

General Preparation Scheme[1]

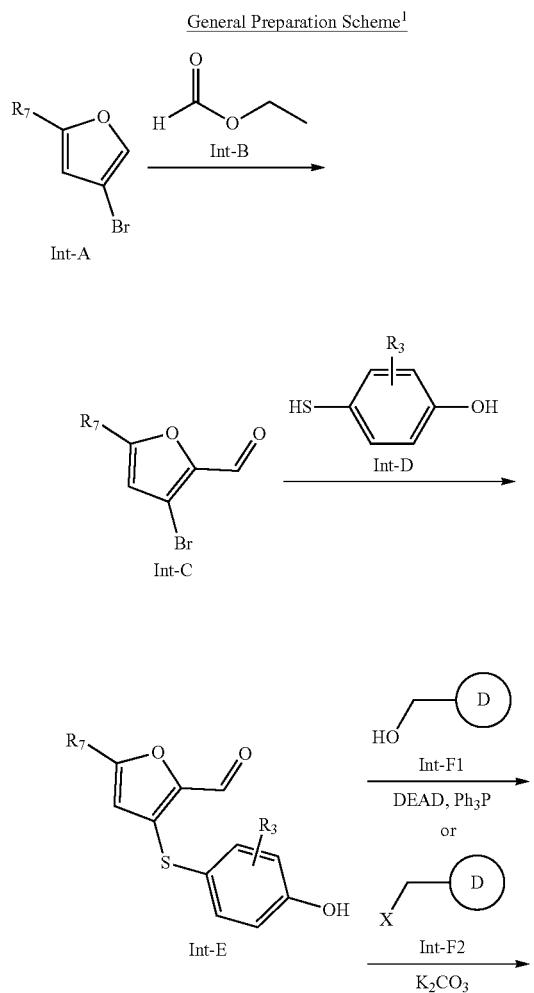

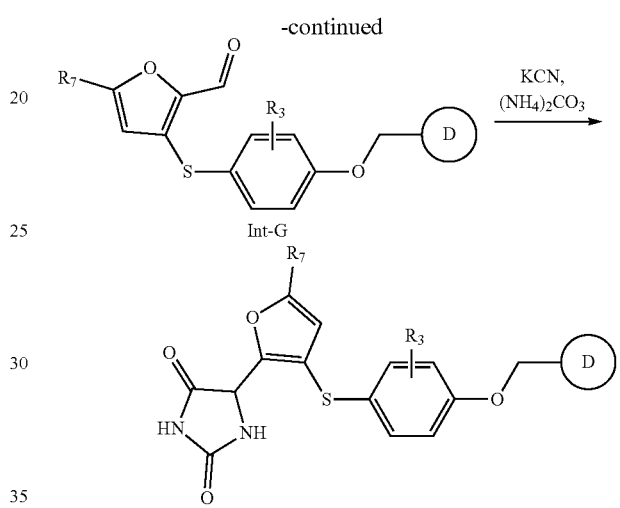

[1]$R_3$ is hydrogen, alkyl, or halo; $R_7$ is hydrogen or alkyl; ring D is optionally substituted aryl or heteroaryl; X is halo To a solution of LDA is added Int-A and the mixture is stirred at −78° C. for about 1 hour. Then Int-B is added and the mixture is stirred for an additional three hours. The reaction is quenched and extracted. The organic layer is washed, dried, concentrated under vacuum and the residue purified by column chromatograph to obtain Int-C. NaH is added to a mixture of Int-C and Int-D at 0° C. and the mixture is stirred at room temperature overnight. Then the mixture is concentrated, HCl is added to adjust the pH to 6 and the mixture is filtered to give Int-E. Int-E is reacted with Int-F1 in the presence of DEAD and triphenylphosphine to give Int-G. Alternatively, Int-E is reacted with Int-F2 in the presence of potassium carbonate to give Int-G. Then, Int-G is then reacted with (NH$_4$)$_2$CO$_3$ and potassium cyanide (KCN) in aqueous alcohol overnight. The reaction mixture is evaporated to remove the solvent and then extracted. The organic layer is dried and evaporated, and the residue purified by column chromatography to obtain compounds according to embodiments of the application.

General Preparation Scheme 2[1]

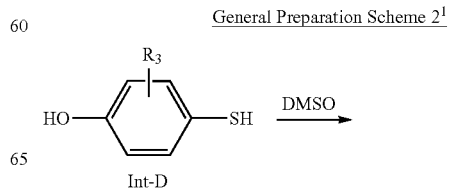

-continued

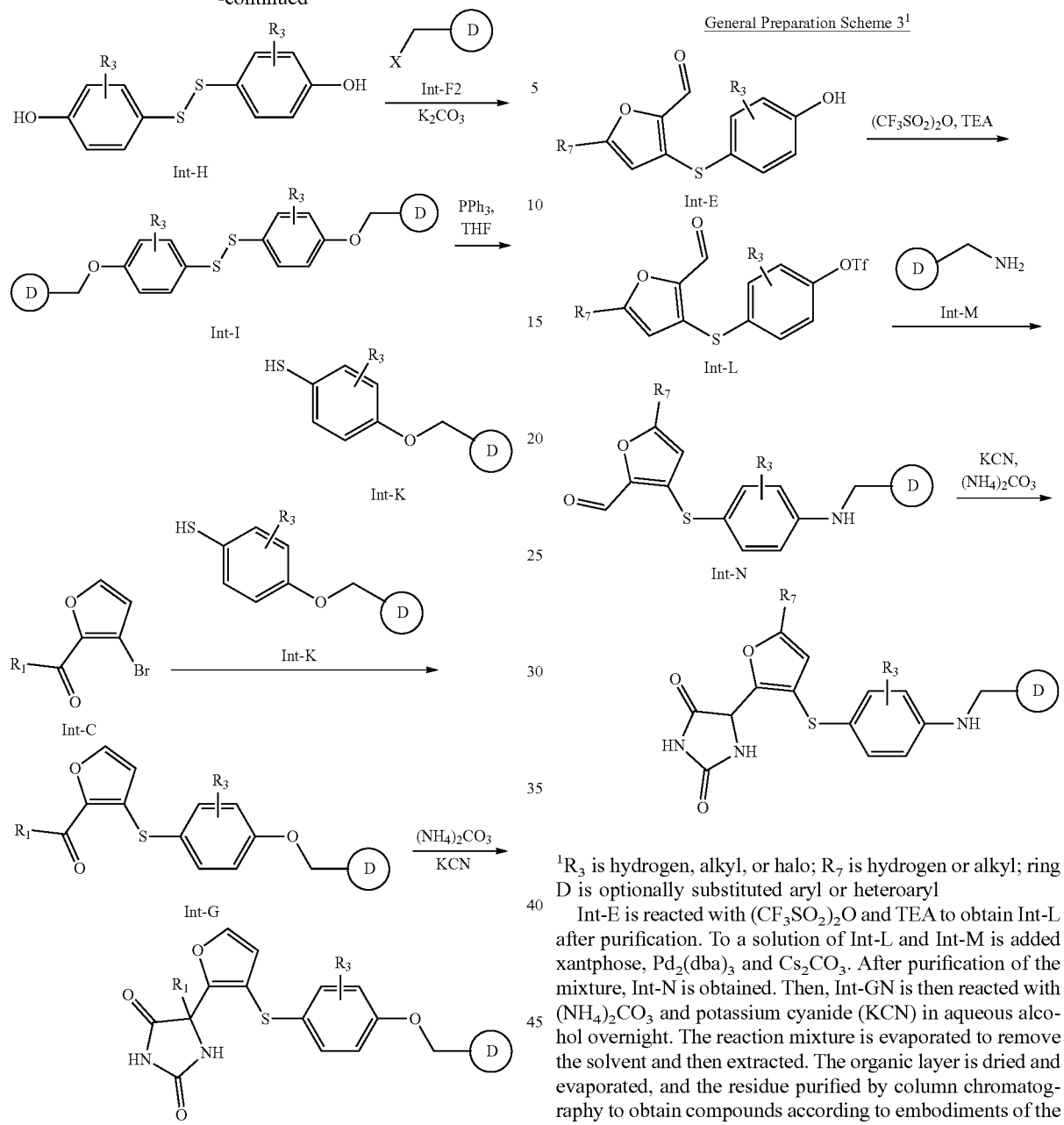

[1] $R_1$ is alkyl; $R_3$ is hydrogen, halo, or alkyl; X is halo; ring D is optionally substituted aryl or optionally substituted heteroaryl Int-D in DMSO is stirred at 80° C. overnight under nitrogen atmosphere. The mixture is purified to yield Int-H. A mixture of Int-H, Int-F2, and potassium carbonate is stirred under heating. The mixture is purified to yield Int-I which is reacted with triphenylphosphine, TBAB and dilute hydrochloric acid to yield Int-K after column purification. Int-C and Int-K are reacted in the presence of sodium hydride to obtain Int-G. Then, Int-G is then reacted with $(NH_4)_2CO_3$ and potassium cyanide (KCN) in aqueous alcohol overnight. The reaction mixture is evaporated to remove the solvent and then extracted. The organic layer is dried and evaporated, and the residue purified by column chromatography to obtain compounds according to embodiments of the application.

[1] $R_3$ is hydrogen, alkyl, or halo; $R_7$ is hydrogen or alkyl; ring D is optionally substituted aryl or heteroaryl Int-E is reacted with $(CF_3SO_2)_2O$ and TEA to obtain Int-L after purification. To a solution of Int-L and Int-M is added xantphose, $Pd_2(dba)_3$ and $Cs_2CO_3$. After purification of the mixture, Int-N is obtained. Then, Int-GN is then reacted with $(NH_4)_2CO_3$ and potassium cyanide (KCN) in aqueous alcohol overnight. The reaction mixture is evaporated to remove the solvent and then extracted. The organic layer is dried and evaporated, and the residue purified by column chromatography to obtain compounds according to embodiments of the application.

Pharmaceutically acceptable salts of compounds of the application can be synthesized from the parent compound containing an acidic or basic moiety by conventional chemical methods. Generally, such salts can be prepared by reacting the free acid or base forms of these compounds with a stoichiometric amount of the appropriate acid or base in water or in an organic solvent, or in a mixture of the two. Examples of suitable organic solvents include, but are not limited to, ether, ethyl acetate, ethanol, isopropanol, or acetonitrile.

Compositions

Another aspect of the application relates to a pharmaceutical composition comprising a compound of the application as described herein, or a or a tautomer, stereoisomer, pharmaceutically acceptable salt, or solvate thereof.

Compositions of the application can also comprise a pharmaceutically acceptable carrier. A pharmaceutically acceptable carrier is non-toxic and should not interfere with the efficacy of the active ingredient. Pharmaceutically acceptable carriers can include one or more excipients such as binders, disintegrants, swelling agents, suspending agents, emulsifying agents, wetting agents, lubricants, flavorants, sweeteners, preservatives, dyes, solubilizers and coatings. The precise nature of the carrier or other material can depend on the route of administration, e.g., intramuscular, intradermal, subcutaneous, oral, intravenous, cutaneous, intramucosal (e.g., gut), intranasal or intraperitoneal routes. For liquid injectable preparations, for example, suspensions and solutions, suitable carriers and additives include water, glycols, oils, alcohols, preservatives, coloring agents and the like. For solid oral preparations, for example, powders, capsules, caplets, gelcaps and tablets, suitable carriers and additives include starches, sugars, diluents, granulating agents, lubricants, binders, disintegrating agents and the like. For nasal sprays/inhalant mixtures, the aqueous solution/suspension can comprise water, glycols, oils, emollients, stabilizers, wetting agents, preservatives, aromatics, flavors, and the like as suitable carriers and additives.

Compositions of the application can be formulated in any matter suitable for administration to a subject to facilitate administration and improve efficacy, including, but not limited to, oral (enteral) administration and parenteral injections. The parenteral injections include intravenous injection or infusion, subcutaneous injection, intradermal injection, and intramuscular injection. Compositions of the application can also be formulated for other routes of administration including transmucosal, ocular, rectal, long acting implantation, sublingual administration, under the tongue, from oral mucosa bypassing the portal circulation, inhalation, or intranasal.

In particular embodiments, compositions are formulated for oral administration.

Yet another aspect of the application relates to a method of preparing a pharmaceutical composition comprising combining a compound of the application or a and any tautomer, stereoisomer, pharmaceutically acceptable salt or solvate thereof with at least one pharmaceutically acceptable carrier. Pharmaceutical compositions can be prepared by any method known in the art in view of the present disclosure, and one of ordinary skill in the art will be familiar with such techniques used to prepare pharmaceutical compositions. For example, a pharmaceutical composition according to the application can be prepared by mixing a compound of the application with one or more pharmaceutically acceptable carriers according to conventional pharmaceutical compounding techniques, including but not limited to, conventional admixing, dissolving, granulating, emulsifying, encapsulating, entrapping or lyophilizing processes.

Methods of Use

The application also provides methods of inhibiting a matrix metalloproteinase (MMP), and treating diseases mediated by MMPs using the compounds of the application and pharmaceutical compositions of the application.

Matrix metalloproteinases (MMPs), also known as matrixins, are a group of enzymes that in concert are responsible for the degradation of most extracellular matrix proteins during organogenesis, growth and normal tissue turnover. MMPs are calcium-dependent zinc-containing endopeptidases, and belong to a larger family of proteases known as the metzincin superfamily. MMPs are capable of degrading extracellular matrix proteins, but can also process a number of bioactive molecules, and known to be involved in, e.g., cleavage of cell surface receptors, release of apoptotic ligands, and chemokine/cytokine inactivation. MMPs are also thought to play a major role in cell behaviors such as cell proliferation, migration (adhesion/dispersion), differentiation, angiogenesis, apoptosis, and host defense. The MMPs are inhibited by specific endogenous tissue inhibitor of metalloproteinases (TIMIPs), which comprise a family of four protease inhibitors: TIMP-1, TIMP-2, TIMP-3, and TIMP-4. Examples of MMPs include, but are not limited to, MMP-1(Interstitial collagenase), MMP-2 (gelatinase-A), MMP-3 (stromelysin 1), MMP-7 (matrilysin), MMP-8 (neutrophil collagenase), MMP-9 (gelatinase-B), MMP-10 (stromelysin 2), MMP-11 (stromelysin 3), MMP-12 (macrophage elastase), MMP-13 (collagenase 3), MMP-14 (MT1-MMP), etc.

In a preferred embodiment, compounds of the application are capable of inhibiting microphage elastase (MMP-12) and/or treating diseases mediated by MMP-12. MMP-12, also known as macrophage metalloelastase (MME) or macrophage elastase (ME), is encoded by the MMP12 gene in humans. In other embodiments, compounds of the application are capable of selectively inhibiting MMP-12. The terms "selective," "selectivity," and "selectively" when used with reference to binding or inhibiting the activity of a particular MMP, mean that a compound binds or inhibits the activity of a particular MMP to a greater extent than said compound binds or inhibits the activity of other MMPs. For example, a compound that has selectivity for MMP-12 inhibits the activity of MMP-12 to a greater extent than other MMPs, e.g., MMP-1, MMP-2, MMP-3, MMP-7, MMP-8, MMP-9, MMP-10, MMP-13, MMP-14, etc.

According to embodiments of the application, a compound that is selective for MMP-12 inhibits the activity of MMP-12 by at least about 10-fold, 100-fold, or 1000-fold greater than one or more other MMPs, and preferably inhibits the activity of MMP-12 by at least about 1000-fold greater than at least one other MMP, such as MMP-1 or MMP-7.

The application also provides methods of treating a disease mediated by MMP-12. According to embodiments of the invention, a method of treating a disease mediated by MMP-12 comprises administering to the subject a therapeutically effective amount of a compound of the application or and any tautomer, stereoisomer, pharmaceutically acceptable salt or solvate thereof, or a pharmaceutical composition of the application.

As used herein, the terms "treat," "treating," and "treatment" are all intended to refer to an amelioration or reversal of at least one measurable physical parameter related to a disease mediated by MMP-12, which is not necessarily discernible in the subject, but can be discernible in the subject. The terms "treat," "treating," and "treatment," can also refer to causing regression, preventing the progression, or at least slowing down the progression of a disease mediated by MMP-12. In a particular embodiment, "treat," "treating," and "treatment" refer to an alleviation, prevention of the development or onset, or reduction in the duration of one or more symptoms associated with a disease mediated by MMP-12. In a particular embodiment, "treat," "treating," and "treatment" refer to prevention of the recurrence of a disease mediated by MMP-12. In a particular embodiment, "treat," "treating," and "treatment" refer to an increase in the survival of a subject having a disease mediated by MMP-12. In a particular embodiment, "treat," "treating," and "treatment" refer to elimination of a disease mediated by MMP-12 in the subject.

As used herein, "a therapeutically effective amount" means an amount of a composition or compound that elicits a biological or medicinal response in a tissue system or subject that is being sought by a researcher, veterinarian, medical doctor or other conditions, which can include alleviation of the symptoms of the disease or disorder being treated. A therapeutically effective amount can vary depending upon a variety of factors, such as the physical condition of the subject, age, weight, health, etc.; and the particular disease to be treated. A therapeutically effective amount can readily be determined by one of ordinary skill in the art in view of the present disclosure.

In particular embodiments of the application, a therapeutically effective amount refers to the amount of a composition or compound of the application which is sufficient to inhibit MMP-12 or treat a disease mediated by MMP-12. Diseases mediated by MMP-12 that can be treated according to the methods of the application include, but are not limited to, asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

Embodiments

Embodiment 1 is a compound of formula (I):

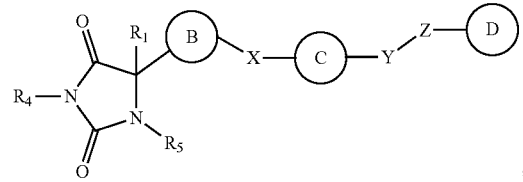

or a tautomer, stereoisomer, pharmaceutically acceptable salt or solvate thereof,
wherein:
  ring B is optionally substituted furanyl;
  ring C is an optionally substituted aryl or optionally substituted heteoraryl;
  ring D is an optionally substituted aryl or optionally substituted heteroaryl;
  each of X, Y and Z is independently selected from the group consisting of $CH_2$, O, $NR_x$ and $S(O)_q$, wherein $R_x$ is hydrogen or alkyl;
  $R_1$ is hydrogen or alkyl;
  $R_4$ is hydrogen or alkyl;
  $R_5$ is hydrogen; and
  q is 0, 1, or 2,
provided that when ring D is phenyl, at least one of the following is true:
  (i) $R_1$ is alkyl;
  (ii) $R_2$ is not methoxy, chloro, or trifluoromethyl; and
  (iii) Ring C is not unsubstituted phenyl.

Embodiment 2 is a compound of formula (II):

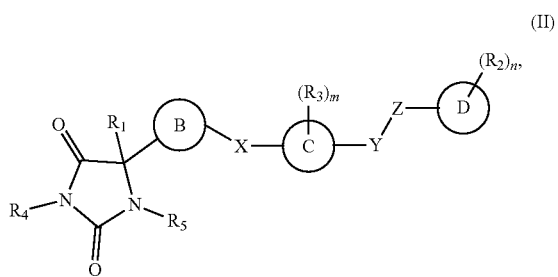

or a tautomer, stereoisomer, pharmaceutically acceptable salt or solvate thereof,
wherein:
  ring B is optionally substituted furanyl;
  ring C is aryl or heteroaryl;
  ring D is aryl or heteroaryl;
  each of X, Y, and Z is independently selected from the group consisting of O, CH, $NR_x$ and $S(O)_q$, wherein $R_x$ is hydrogen or alkyl;
  $R_1$ is hydrogen or alkyl;
  each $R_2$ is independently selected from the group consisting of hydrogen, alkyl, halo, hydroxyl, haloalkyl, alkoxy, alkylthio, amino, amide, alkylamino, aminoalkyl, cyano, hydroxyalkyl, $-(CH_2)_pC(O)OR_6$, and $-(CH_2)_pOC(O)R_6$;
  each $R_3$ is independently selected from the group consisting of hydrogen, alkyl and halo;
  $R_4$ is hydrogen or alkyl;
  $R_5$ is hydrogen;
  each $R_6$ is independently selected from the group consisting of hydrogen and alkyl, wherein the alkyl is unsubstituted or substituted with one or more groups independently selected from the group consisting of amine, hydroxyl, halo, and alkoxy;
  m is 1, 2, 3, or 4;
  n is 1, 2, 3, 4, or 5;
  p is 0, 1, 2, 3, 4, or 5; and
  q is 0, 1, or 2;
provided that when ring D is phenyl, at least one of the following is true:
  (i) $R_1$ is alkyl;
  (ii) $R_2$ is not methoxy, chloro, or trifluoromethyl; and
  (iii) Ring C is not unsubstituted phenyl.

Embodiment 3 is the compound of embodiment 1 or embodiment 2, wherein ring C is phenyl.

Embodiment 4 is the compound of embodiment 1 or embodiment 2, wherein ring C is pyridinyl.

Embodiment 5 is the compound of any one of embodiments 2 to 4, wherein $R_3$ is selected from the group consisting of hydrogen, methyl, fluoro, and chloro.

Embodiment 6 is the compound of any one of embodiments 1 to 5, wherein ring D is pyridinyl.

Embodiment 7 is the compound of any one of embodiments 1 to 5, wherein ring D is phenyl.

Embodiment 8 is the compound of any one of embodiments 2 to 7, wherein $R_2$ is selected from the group consisting of methyl, $-CH_2OH$, hydroxyl, $-OC(O)CH(NH_2)CH(CH_3)_2$, $-COOH$, $-CH_2OC(O)CH(NH_2)CH(CH_3)_2$, $-C(O)NH_2$, $-C(O)NH(CH_3)$, and $C_{1-4}$alkoxy.

Embodiment 9 is the compound of embodiment 8, wherein $R_2$ is selected from the group consisting of $-CH_2OH$, hydroxyl, $-OC(O)CH(NH_2)CH(CH_3)_2$, $-COOH$, $-CH_2OC(O)CH(NH_2)CH(CH_3)_2$, $-C(O)NH_2$, $-C(O)NH(CH_3)$, and $C_{2-4}$alkoxy.

Embodiment 10 is the compound of any one of embodiments 2 to 7, wherein $R_2$ is selected from the group consisting of alkyl, amide, hydroxyl, alkoxy, and hydroxylalkyl.

Embodiment 11 is the compound of embodiment 10, wherein n is 1; and $R_2$ is is —$CH_3$, $C_{1-4}$ alkoxy, —OH, —$CH_2OH$, or —$C(O)NH_2$.

Embodiment 12 is the compound of any one of embodiments 1 to 5, wherein ring D is:

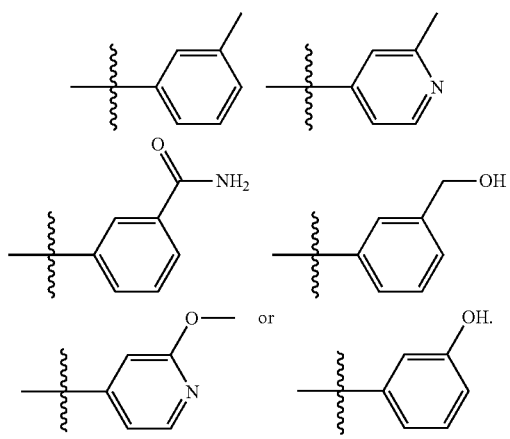

Embodiment 13 is the compound of any one of embodiments 1 to 12, wherein $R_4$ is hydrogen.

Embodiment 14 is the compound of any one of embodiments 1 to 12, wherein $R_4$ is alkyl.

Embodiment 15 is the compound of embodiment 14, wherein $R_4$ is methyl.

Embodiment 16 is the compound of any one of embodiments 1 to 15, wherein $R_1$ is hydrogen.

Embodiment 17 is the compound of any one of embodiments 1 to 15, wherein $R_1$ is alkyl.

Embodiment 18 is the compound of embodiment 17, wherein $R_1$ is $C_{1-4}$ alkyl.

Embodiment 19 is the compound of embodiment 18, wherein $R_1$ is —$CH_3$, —$CH_2CH_3$, —$CH_2CH_2CH_3$, —$CH(CH_3)_2$, or —$CH_2CH(CH_3)_2$.

Embodiment 20 is the compound of any one of embodiments 1 to 19, wherein X is S.

Embodiment 21 is the compound of any one of embodiments 1 to 20, wherein Z is $CH_2$.

Embodiment 22 is the compound of any one of embodiments 1 to 19, wherein X is S, Y is O, and Z is $CH_2$.

Embodiment 23 the compound of embodiment 2, being a compound of formula (III):

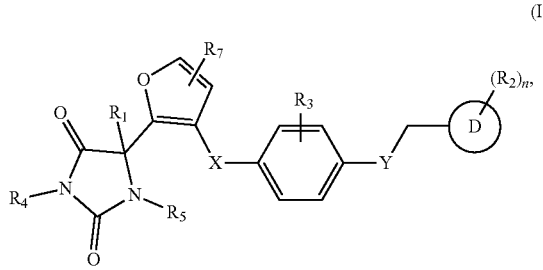

(III)

or a tautomer, stereoisomer, pharmaceutically acceptable salt or solvate thereof,
wherein:
$R_1$ is hydrogen or $C_{1-4}$ alkyl;
X is S;
Y is O, $CH_2$, NH, or $N(CH_3)$;
each $R_2$ is independently selected from the group consisting of hydrogen, alkyl, hydroxyl, alkoxy, amide, and hydroxyalkyl;
each $R_3$ is hydrogen, alkyl or halo;
ring D is phenyl, pyridinyl, or pyridinyl N-oxide;
each of $R_4$ and $R_5$ is hydrogen;
$R_7$ is hydrogen or methyl; and
n is 1 or 2.

Embodiment 24 is a compound of formula (IV):

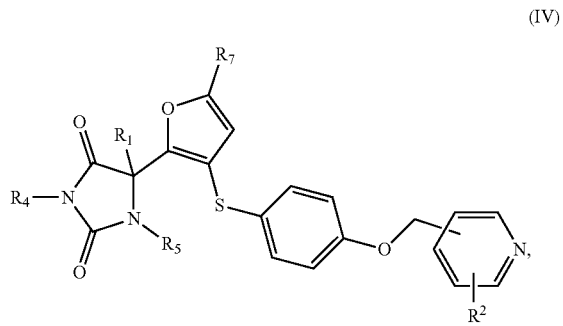

(IV)

or a tautomer, stereoisomer, pharmaceutically acceptable salt or solvate thereof,
wherein:
$R_1$ is hydrogen or alkyl;
$R_2$ is selected from the group consisting of alkyl, amide, hydroxyl, alkoxy, and hydroxylalkyl;
$R_4$ is hydrogen or alkyl;
$R_5$ is hydrogen; and
$R_7$ is methyl or hydrogen.

Embodiment 25 is the compound of embodiment 24, wherein $R_4$ is hydrogen.

Embodiment 26 is the compound of embodiment 24 or 25, wherein $R_2$ is —$CH_3$, $C_{1-4}$ alkoxy, —OH, —$CH_2OH$, or —$C(O)NH_2$.

Embodiment 27 is the compound of any one of embodiments 24 to 26, wherein $R_1$ is $C_{1-4}$ alkyl.

Embodiment 28 is a compound of formula (V):

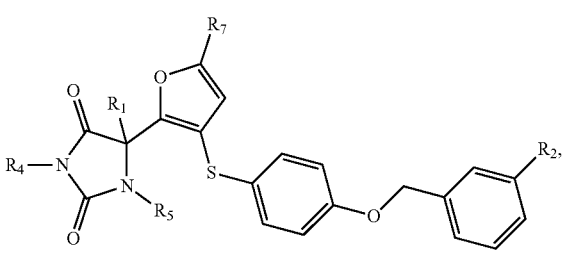

or a tautomer, stereoisomer, pharmaceutically acceptable salt or solvate thereof,
wherein:
$R_1$ is alkyl;
$R_2$ is selected from the group consisting of alkyl, amide, alkoxy, hydroxyl, and hydroxyalkyl;
$R_4$ is hydrogen or alkyl;
$R_5$ is hydrogen; and
$R_7$ is methyl or hydrogen.

Embodiment 29 is the compound of embodiment 28, wherein R₄ is hydrogen.
Embodiment 30 is the compound of embodiment 28 or embodiment 29, wherein R₂ is —CH₃, C₁₋₄ alkoxy, —OH, —CH₂OH, or —C(O)NH₂.
Embodiment 31 is the compound of any one of embodiments 28-30, wherein R₁ is C₁₋₄ alkyl.
Embodiment 32 is the compound of any one of embodiments 1 to 31, which is not:
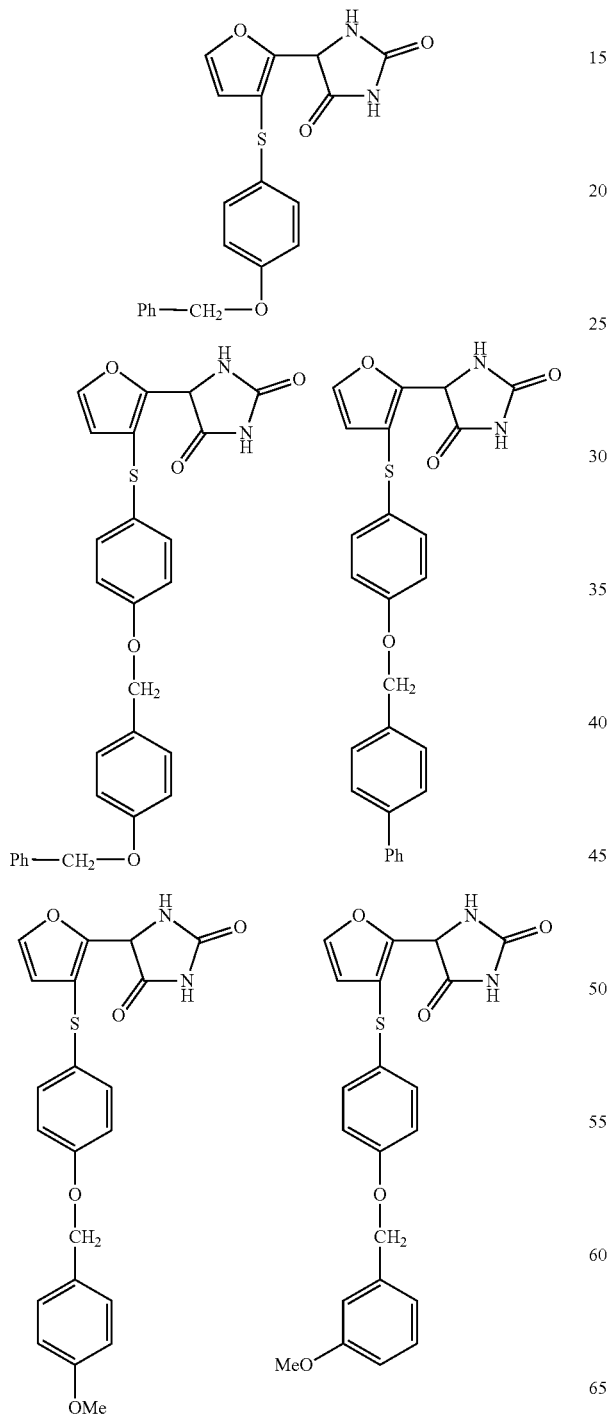
-continued
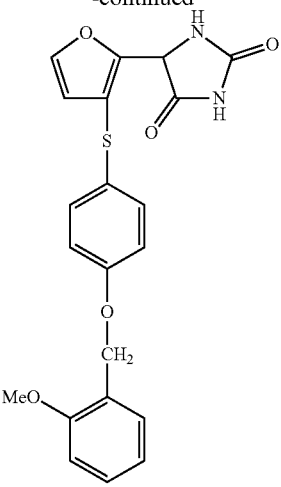
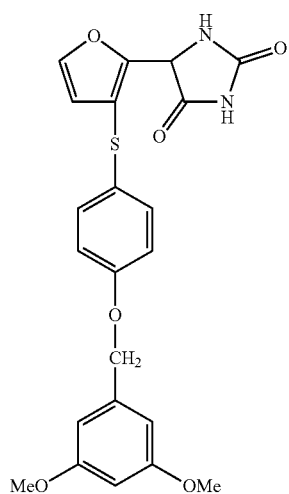
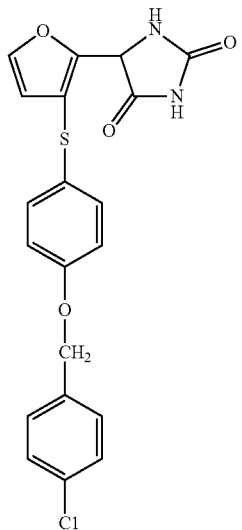

-continued

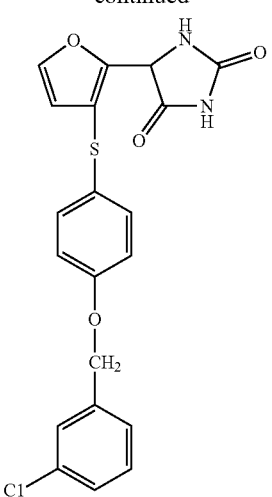

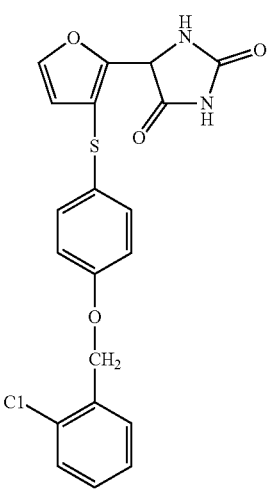

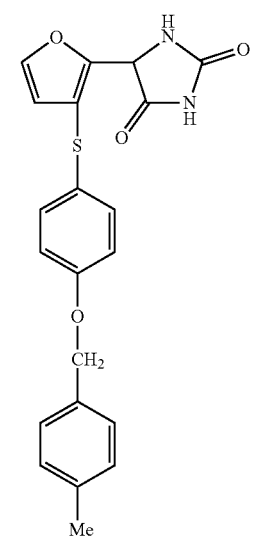

-continued

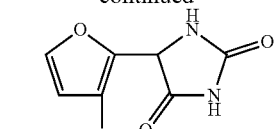

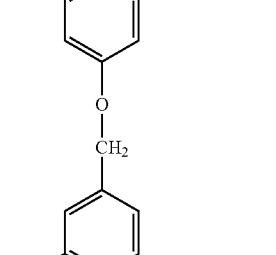

or

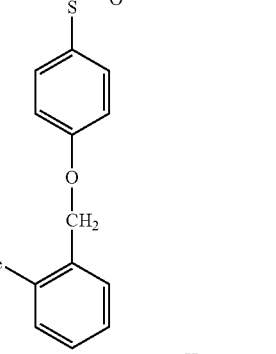

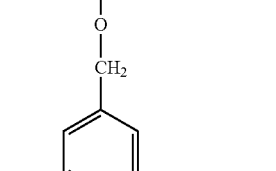

Embodiment 33 is a compound selected from the group consisting of the compounds in Table 1, or a tautomer, stereoisomer, pharmaceutically acceptable salt or solvate thereof.

Embodiment 34 is a pharmaceutical composition comprising the compound of any one of embodiments 1-33, and at least one pharmaceutically acceptable carrier.

Embodiment 35 is a method of inhibiting macrophage elastase (MMP-12) in a subject in need thereof, the method comprising administering to the subject the pharmaceutical composition of embodiment 34.

Embodiment 36 is a method of treating a disease mediated by macrophage elastase (MMP-12) in a subject in need thereof, the method comprising administering to the subject the pharmaceutical composition of embodiment 34.

Embodiment 37 is the method of embodiment 36, wherein the disease is selected from the group consisting of asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

Embodiment 38 is the compound of any one of embodiments 1-33, or the pharmaceutical composition of embodiment 34 for use in inhibiting macrophage elastase (MMP-12).

Embodiment 39 is the compound of any one of embodiments 1-33, or the pharmaceutical composition of embodiment 34 for use treating a disease mediated by macrophage elastase (MMP-12).

Embodiment 40 is the compound or composition for use of embodiment 39, wherein the disease is selected from the group consisting of asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

Embodiment 41 is use of the compound of any one of embodiments 1-33, or the pharmaceutical composition of embodiment 34 in the manufacture of a medicament for inhibiting macrophage elastase (MMP-12).

Embodiment 42 is use of the compound of any one of embodiments 1-33, or the pharmaceutical composition of embodiment 34 in the manufacture of a medicament for treating a disease mediated by macrophage elastase (MMP-12).

Embodiment 43 is use of embodiment 42, wherein wherein the disease is selected from the group consisting of asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

Embodiment 44 is a method of preparing the pharmaceutical composition of embodiment 33, comprising combining the compound or a pharmaceutically acceptable salt thereof with at least one pharmaceutically acceptable carrier.

EXAMPLES

The following examples of the application are to further illustrate the nature of the application. It should be understood that the following examples do not limit the application and the scope of the application is to be determined by the appended claims.

Methods of Synthesis

Unless indicated otherwise, the abbreviations for chemical reagents and synthesis conditions have their ordinary meaning known in the art as follows:

"LDA" refers to lithium diisopropyl amide;

"EA" refers to ethyl acetate;

"PE" refers to petroleum ether;

"r.t." and "rt" refer to room temperature;

"THF" refers to tetrahydrofuran;

"DEAD" refers to diethyl azodicarboxylate;

"TBAB" refers to tetrabutylammonium bromide;

"DCM" refers to dichloromethane;

"HOBT" refers to hydroxybenzotriazole;

"LAH" refers to lithium aluminum hydride;

"TLC" refers to thin layer chromatography;

"Prep-TLC" refers to preparatory thin layer chromatography;

"TMS-I" refers to trimethylsilyl iodide;

"Hex" refers to hexanes;

"DMF" refers to dimethylformamide;

"h" refers to hours;

"EDCI" refers to 1-Ethyl-3-(3-dimethylaminopropyl)carbodiimide;

"DMAP" refers to 4-Dimethylaminopyridine;

"Prep-HPLC" refers to preparative high performance liquid chromatography;

"DHP" refers to dihydropyran;

"DPPF" refers to 1,1'-Bis(diphenylphosphino)ferrocene; and

"DIEA" refers to diisopropylethylamine.

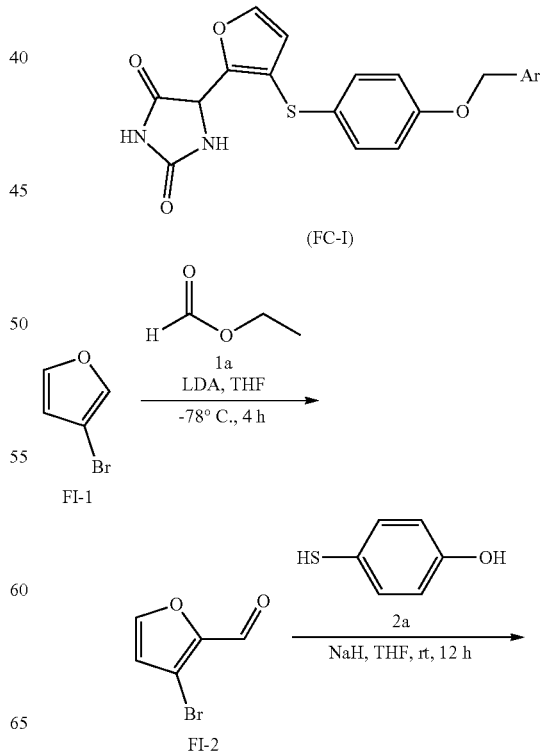

General Scheme 1: Preparation of Compounds FC-I

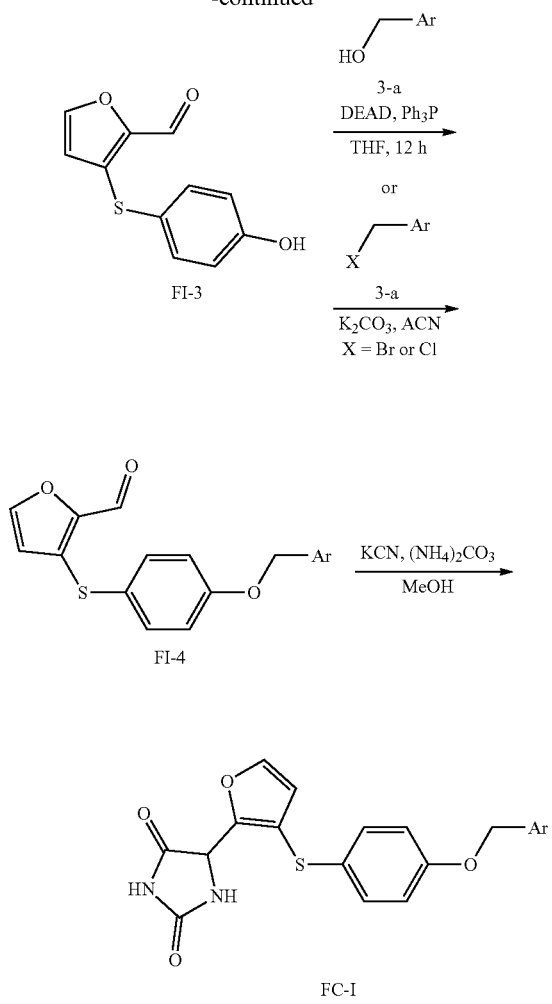

General Procedure for the Preparation of Compound FI-2

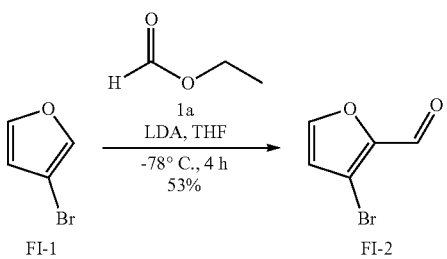

To a solution of lithium diisopropyl amide (LDA) (68 mL, 68.04 mmol, 1.0 eq) in tetrahydrofuran (THF) (100 mL) was added a solution of compound FI-1 (10 g, 68.04 mmol, 1.0 eq) at −78° C. The mixture was stirred at −78° C. for 1 hour. Then compound 1a was added and the mixture was stirred at −78° C. for 3 hours. The reaction was quenched with a saturated aqueous solution of NH₄Cl (100 mL) and extracted with ethyl acetate (EA) three times (50 mL×3). The organic layer was washed with brine and water, dried over Na₂SO₄ and concentrated in a vacuum. The residue was purified by column chromatography on a silica gel (PE:EA, 10:1) to give compound FI-2 (6.3 g, 53%).

General Procedure for the Preparation of Compound FI-3

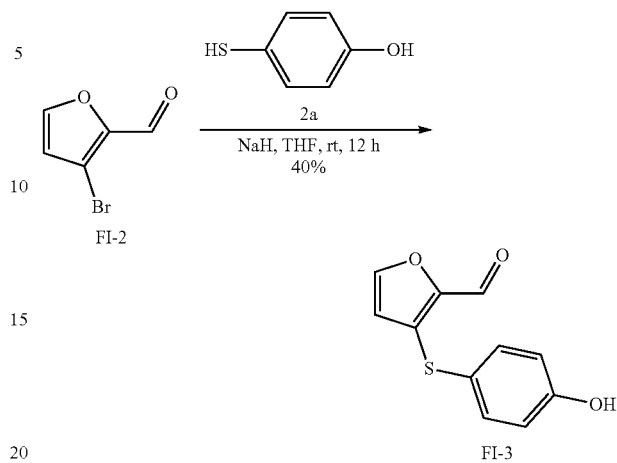

To a mixture of compound FI-2 (5 g, 28.57 mmol, 1.0 eq), compound 2a (5.4 g, 42.86 mmol, 1.5 eq) in THF (100 mL) was added NaH (1.37 g, 57.15 mmol, 2.0 eq) at 0° C. and the mixture was stirred at room temperature (rt) overnight under nitrogen atmosphere. Then the mixture was concentrated to half the amount of solvent, then 2.0 N HCl was added to adjust the pH=6, and filtered to give compound FI-3 (2.5 g, 40%), which was used in the next step without further purification.

Preparation of Compound FC-1:

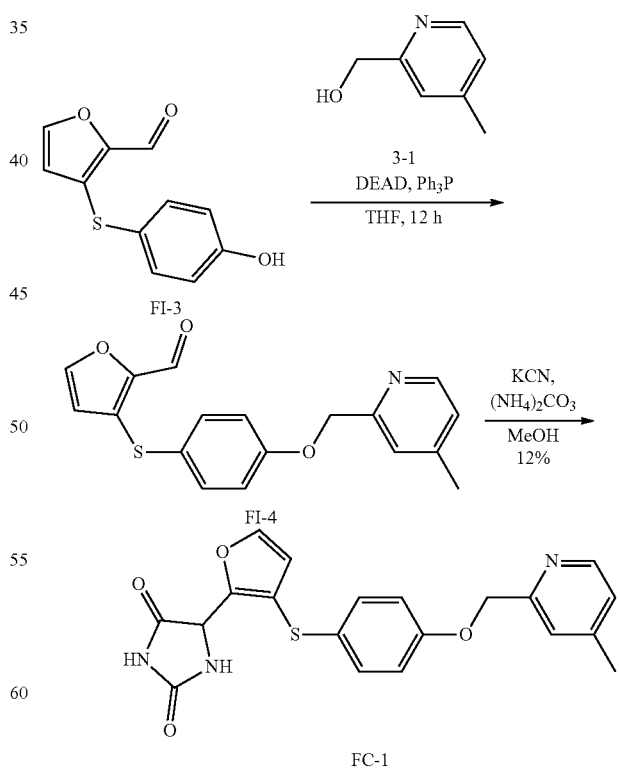

To a solution of compound FI-3 (250 mg, 1.14 mmol, 1.0 eq) in THF (10 mL) was added compound 3-1 (700 mg, 5.68 mmol, 5.0 eq), PPh₃ (600 mg, 2.28 mmol, 2.0 eq) and DEAD (396 mg, 2.28 mmol, 2.0 eq) at 0° C. The mixture was stirred at rt overnight. Then the mixture was quenched with H₂O (10 mL), and extracted with EA (10 mL*2). The organic layer was dried over Na₂SO₄ and concentrated. The residue was purified by column chromatography on a silica gel to give compound FI-4 (50 mg, 14%).

To a mixture of compound FI-4 (80 mg, 0.24 mmol, 1.0 eq) in MeOH (10 mL) was added KCN (32 mg, 0.24 mmol, 2.0 eq) and (NH₄)₂CO₃ (92 mg, 0.48 mmol, 4.0 eq). The mixture was stirred at 40° C. overnight under nitrogen atmosphere. Then the mixture was quenched with H₂O (10 mL), extracted with EA (10 mL*2). The organic layer was dried over Na₂SO₄ and concentrated. The residue was purified by column chromatography on a silica gel to give compound FC-1 (5.6 mg, 12%).

Preparation of Compounds FC-2, FC-3 and FC-4:

Compounds FC-2, FC-3, and FC-4 were synthesized using the same procedure as FC-1 except starting material 3-a was replaced by compounds 3-2, 3-3, and 3-4, accordingly:

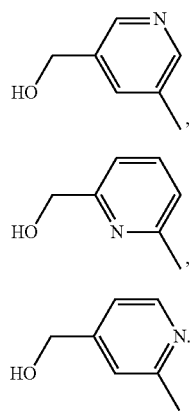

3-2

3-3

3-4

Preparation of Compounds FC-5, FC-6 and FC-7:

Compounds FC-5, FC-6, and FC-7 were synthesized using the same procedure as FC-1, except starting material 3-a was replaced by intermediates 3-5, 3-6, and 3-7, accordingly:

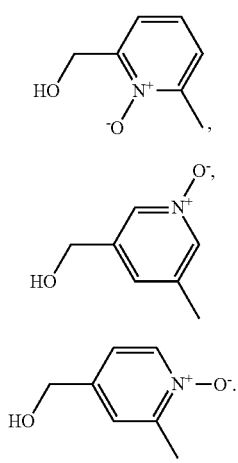

3-5

3-6

3-7

Preparation of the Intermediate 3-5:

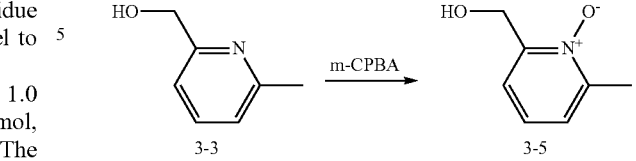

To a mixture of compound 3-3 (1 g, 8.13 mmol, 1.0 eq) in DCM (10 mL) was added m-CPBA (2.1 g, 12.195 mmol, 1.5 eq). The mixture was stirred at room temperature for 16 h. Then the mixture was filtered and concentrated under reduced pressure. The residue was purified by silica gel chromatography to afford compound 3-5 (0.7 g, 62%)

Preparation of Intermediates 3-6 and 3-7:

Intermediates 3-6 and 3-7 were synthesized using the same procedure as the synthesis of intermediate 3-5, except that the starting materials were replaced by starting materials 3-2 and 3-4, accordingly.

General Scheme 2: Preparation of Compounds FC-II

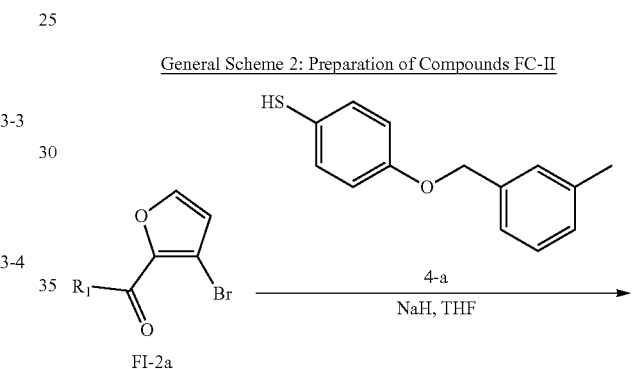

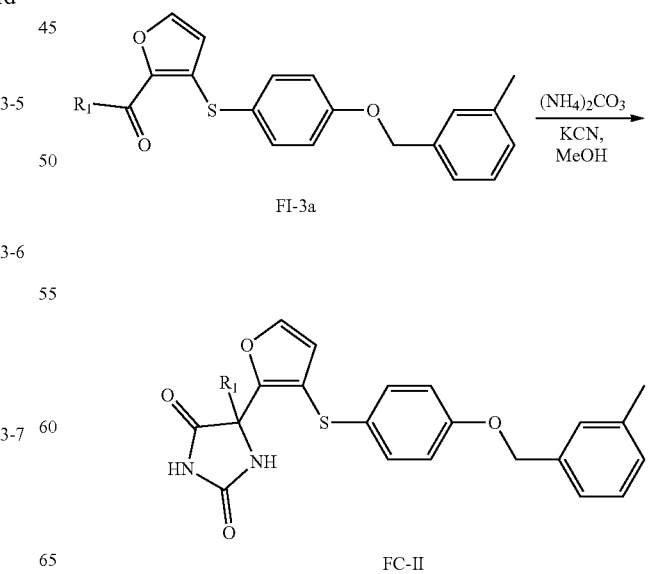

FC-II

General Scheme 3: Preparation of Intermediate 4a-1

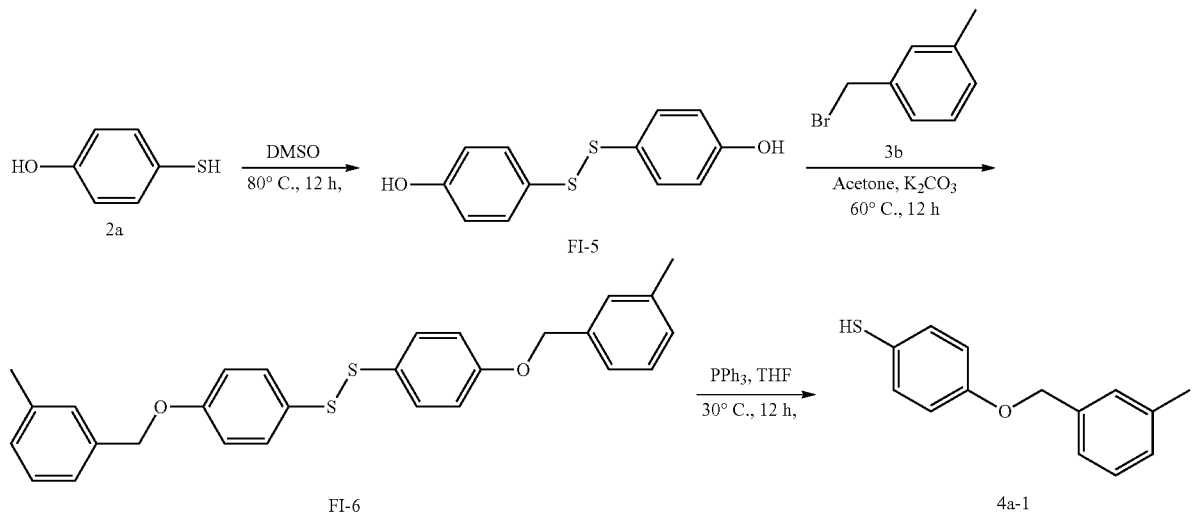

Synthesis of Intermediate FI-5:

A mixture of compound 2a (68 g, 538.9 mmol, 1.0 eq) in DMSO (500 mL) was stirred at at 80° C. overnight under nitrogen atmosphere. Then the mixture was diluted with H₂O (1000 mL) and extracted with ethyl acetate. The organic layer was washed with brine, dried over Na₂SO₄, filtered and concentrated to give compound FI-5 (67 g, 99%).

Synthesis of Intermediate FI-6:

A mixture of compound FI-5 (5 g, 19.97 mmol, 1.0 eq), compound 3b (7.39 g, 39.95 mmol, 2 eq) and K₂CO₃ (11.04 g, 79.89 mmol, 4.0 eq) in acetone (100 mL) was stirred at 60° C. for 4 h under nitrogen atmosphere. Then the mixture was diluted with H₂O (1000 mL) and extracted with ethyl acetate. The organic layer was washed with brine, dried over Na₂SO₄, filtered and concentrated. The residue was purified by column chromatography on a silica gel (PE/EA, 10:1) to give compound FI-6 (8.7 g, 97%).

Synthesis of Compound 4a-1:

To a mixture of compound FI-6 (10.7 g, 23.33 mmol, 1.0 eq) in THF (100 mL) was added PPh₃ (6.11 g, 23.33 mmol, 1 eq), TBAB (15.04 g, 46.66 mmol, 2 eq) and 5% HCl (5 mL). The mixture was stirred at rt for 12 h under nitrogen atmosphere. Then the mixture was concentrated. The residue was purified by column chromatography on a silica gel (PE/EA, 2:1) to give compound 4a-1 (6.6 g, 56%).

Preparation of Compound FC-8:

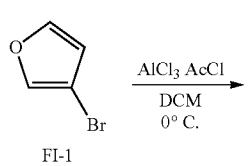

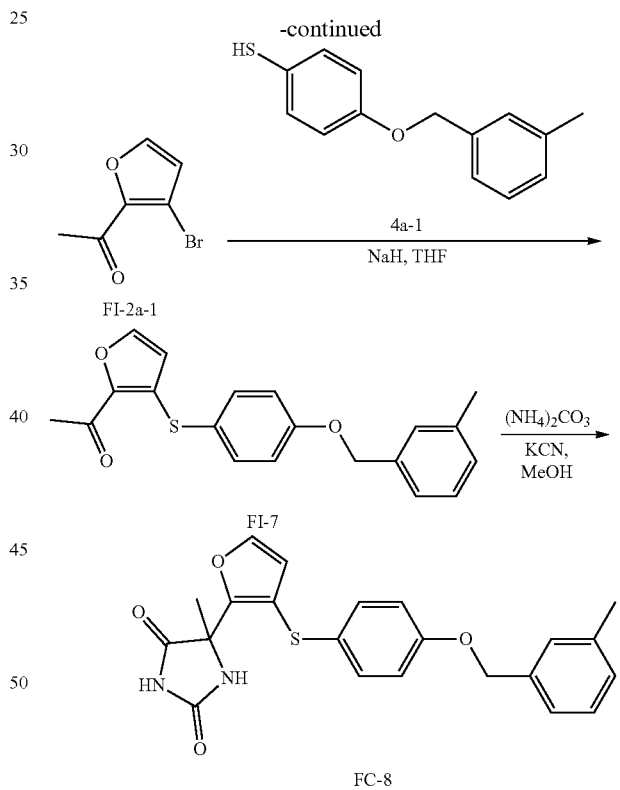

To a solution of AlCl₃ 1.34 g, 10.2 mmol, 3.0 eq) in DCM (15 mL) was added a solution of AcCl (0.8 g, 10.2 mmol, 3.0 eq) in DCM (5 mL) slowly at 0° C. under nitrogen atmosphere. The mixture was stirred at 0° C. for 30 min. Then a solution of compound FI-1 (0.5 g, 3.4 mmol, 1.0 eq) in DCM (5 mL) was added slowly. The mixture was stirred at 0° C. for 20 min. Then the mixture was allowed to warm to room temperature and stirred for 10 min. The mixture was quenched with ice-cold water and extracted with ethyl acetate. The organic phase was dried over anhydrous Na₂SO₄ and concentrated under reduced pressure. The residue was purified by silica gel chromatography to afford compound FI-2a-1 (0.6 g, 93%).

To a mixture of compound FI-2a-1 (0.2 g, 1.23 mmol, 1.0 eq) and compound 4a-1 (0.43 g, 1.85 mmol, 1.5 eq) in THF (10 mL) was added NaH (60 mg, 2.47 mmol, 2.0 eq) at 0° C. The mixture was allowed to warm to room temperature and stirred for 16 h under nitrogen atmosphere. Then the mixture was concentrated to half solvent and 2 N HCl was added to adjust the pH=6, filtered and the filtrated was concentrated. The residue was purified by column chromatography on a silica gel to give compound FI-7 (0.3 g, 83%).

To a mixture of compound FI-7 (0.3 g, 0.888 mmol, 1.0 eq) in MeOH (5 mL) was added KCN (115 mg, 1.775 mmol, 2.0 eq) and (NH$_4$)$_2$CO$_3$ (341 mg, 3.550 mmol, 4.0 eq). The mixture was stirred at room temperature for 12 h. Then the mixture was diluted with water and extracted with ethyl acetate. The organic phase was dried over anhydrous Na$_2$SO$_4$ and concentrated under reduced pressure. The residue was purified by Prep-TLC to give compound FC-8 (65 mg, 18%) as a colorless oil.

Alternative Route to Prepare the Intermediate FI-2a:

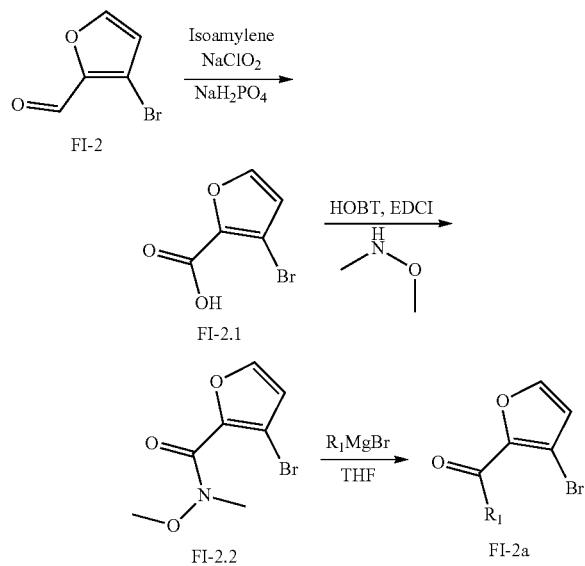

Preparation of Intermediate FI-2a-2:

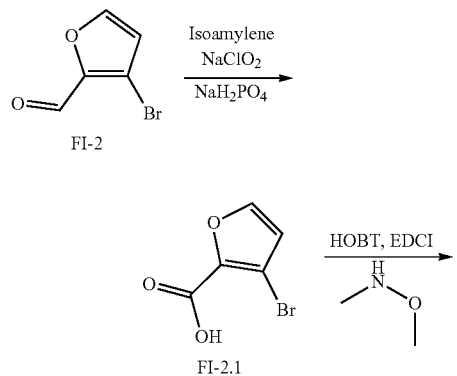

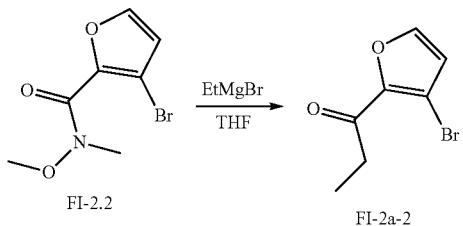

To a solution of compound FI-2 (5 g, 30.9 mmol, 1.0 eq) and isoamylene (9 mL, 77.2 mmol, 2.5 eq) in tert-butanol (50 mL) was added a solution of NaClO$_2$ (8.1 g, 89.6 mmol, 3.0 eq) and NaH$_2$PO$_4$·2H$_2$O (10.3 g, 67.9 mmol, 2.2 eq) in H$_2$O (70 mL) slowly. The mixture was stirred at room temperature for 16 h. The mixture was concentrated under reduced pressure and diluted with H$_2$O. Then 1 M HCl was added to the mixture to adjust pH=1 and filtered to afford compound FI-2.1 (6.2 g, 100%).

To a mixture of compound FI-2.1 (5 g, 26.46 mmol, 1.0 eq) and TEA (8 g, 79.37 mmol, 3.0 eq) was added N,O-dimethylhydroxylamine (5.16 g, 52.91 mmol, 2.0 eq), HOBT (3.93 g, 29.1 mmol, 1.1 eq) and EDCI (6.06 g, 31.75 mmol, 1.2 eq). The mixture was stirred for 5 h. Then the mixture was diluted with water and extracted with ethyl acetate. The organic phase was dried over anhydrous Na$_2$SO$_4$ and concentrated under reduced pressure. The residue was purified by silica gel chromatography to afford compound FI-2.2 (4.3 g, 67%).

To a mixture of compound FI-2.2 (1 g, 4.29 mmol, 1.0 eq) in dry THF (10 mL) was added EtMgBr (1.0 mol/L in THF, 8.6 mL, 8.58 mmol, 2.0 eq) dropwise at 0° C. under nitrogen atmosphere. The mixture was stirred at 0° C. for 1 h. The reaction was quenched with saturated aqueous NH$_4$Cl and extracted with ethyl acetate (3×50 mL). The combined organic layers were washed with brine and water, dried over Na$_2$SO$_4$ and concentrated under vacuum. The residue was purified by column chromatography on a silica gel to give compound FI-2a-2 (0.6 g, 69%).

Preparation of Intermediates FI-2a-3, FI-2a-4 and FI-2a-5:

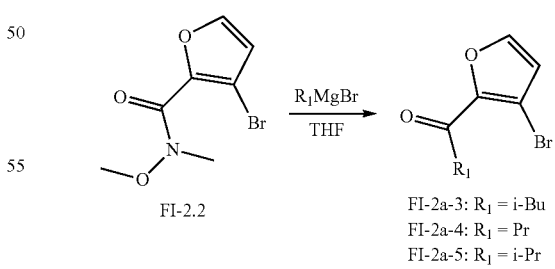

The procedures to prepare FI-2a-3, FI-2a-4 and FI-2a-5 are similar to the synthesis of FI-2a-2 except to replace EtMgBr with i-BuMgBr, PrMgBr, and i-PrMgBr accordingly.

Preparation of Compound FC-9, FC-10, FC-11 and FC-12:

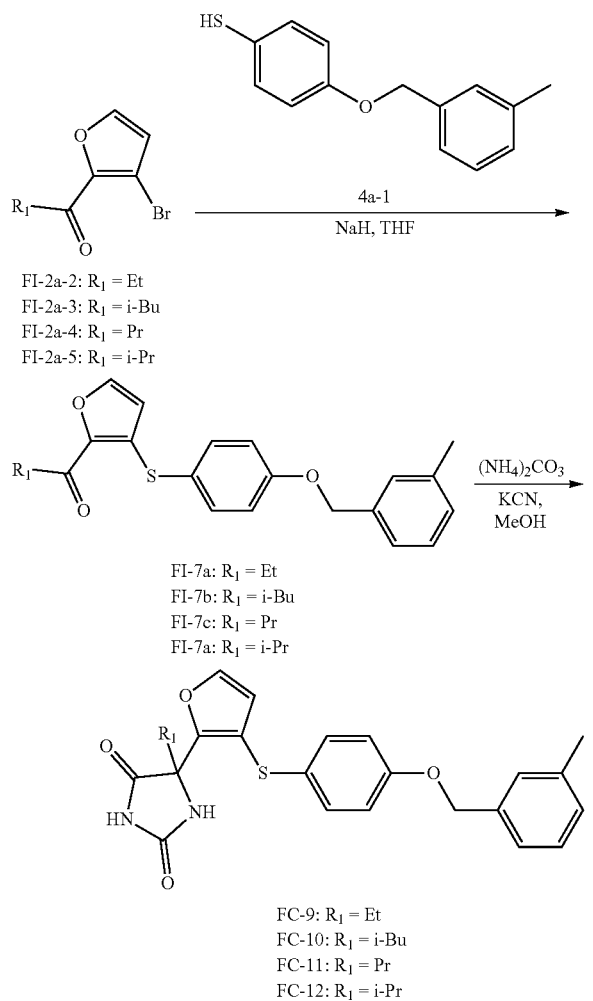

General Scheme to Prepare Compounds FC-13, FC-14, FC-15 and FC16:

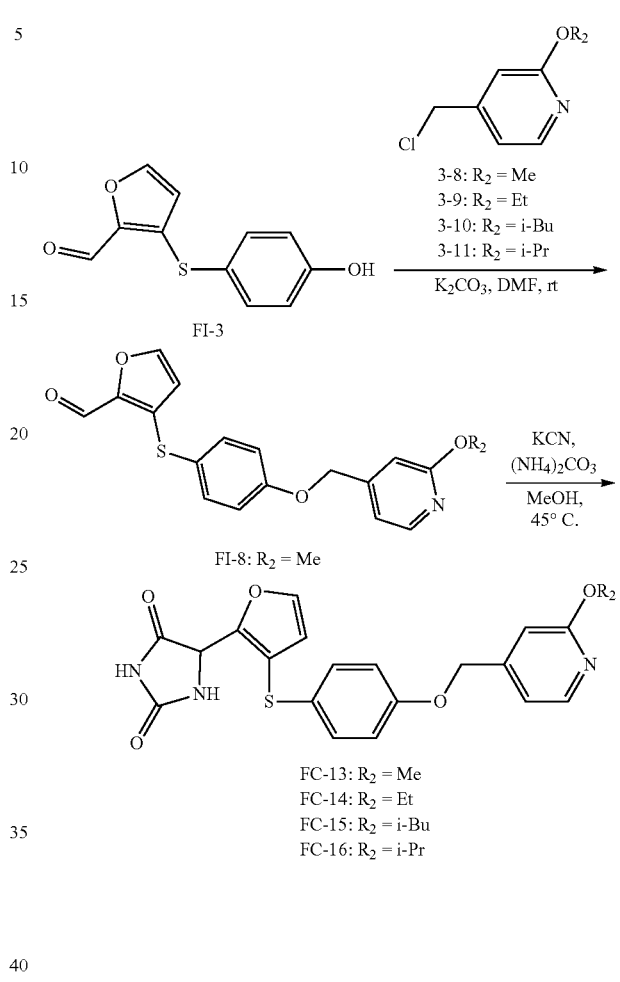

To a mixture of compound FI-2a-2 (200 mg, 0.99 mmol, 1.0 eq) and compound 4a-1 (343 mg, 1.49 mmol, 1.5 eq) in THE (10 mL) was added NaH (79 mg, 1.98 mmol, 2.0 eq) at 0° C. The mixture was allowed to warm to room temperature and stirred for 16 h under nitrogen atmosphere. Then the mixture was concentrated to half solvent and then 2 N HCl was added to adjust pH=6, filtered and the filtrate was concentrated. The residue was purified by column chromatography on a silica gel to give compound FI-7a (180 mg, 52%).

To a solution of compound FI-7a (180 mg, 0.511 mmol, 1.0 eq) in MeOH (5 mL) was added $(NH_4)_2CO_3$ (196 mg, 2.05 mmol, 4.0 eq) and KCN (66 mg, 1.02 mmol, 2.0 eq). The mixture was stirred at 45° C. for 16 h. The reaction was added 3 M HCl to adjust pH=1-2 and stirred at room temperature for 1 h, then a saturated aqueous solution of $NaHCO_3$ was added to adjust pH=6 to 7 and extracted with ethyl acetate. The organic layer was washed with brine, dried over anhydrous $Na_2SO_4$ and concentrated under reduced pressure. The residue was purified by Prep-TLC to give FC-9 (48 mg, 22%) as a colorless oil.

The procedures to prepare FC-10, FC-11 and FC-12 are similar to the synthesis of FC-9 except that FI-2a-2 was replaced with FI-2a-3, FI-2a-4, and FI-2a-5 accordingly.

To a mixture of compound 3-8 (750 mg, 3.876 mmol, 1.0 eq) in DMF (15 mL) was successively added compound FI-3 (895 mg, 3.876 mmol, 1.0 eq) and $K_2CO_3$ (2.14 g, 15.5 mmol, 4.0 eq). The mixture was stirred at room temperature for 16 h under nitrogen atmosphere. Then 3 M HCl was added to adjust the pH=6 to 7. The mixture was extracted with EA and the organic layer was washed with brine, dried over $Na_2SO_4$, and concentrated under reduced pressure. The residue was purified by column chromatography on a silica gel (PE/EA, 1:1) to give compound FI-8 (610 mg, 36%).

To a solution of compound FI-8 (500 mg, 1.419 mmol, 1.0 eq) in MeOH (6 mL) was added $(NH_4)_2CO_3$ (545 mg, 5.676 mmol, 4.0 eq) and KCN (185 mg, 2.838 mmol, 2.0 eq). The mixture was stirred at 45° C. for 16 h. Then, 3 M HCl was added to the reaction to adjust the pH=1 to 2 and stirred at room temperature for 1 h, then saturated aqueous of $NaHCO_3$ was added to adjust the pH=6 to 7 and extracted with ethyl acetate. The organic layer was washed with brine, dried over anhydrous $Na_2SO_4$ and concentrated under reduced pressure. The residue was purified by Prep-TLC to give FC-13 (350 mg, 58%) as a white solid.

Compounds FC-14, FC15 and FC-16 were synthesized by the same procedure as FC-13, except that intermediate 3-8 was replaced with intermediate 3-9, 3-10 or 3-11, accordingly.

Preparation of Intermediates 3-8, 3-9, 3-10 and 3-11:

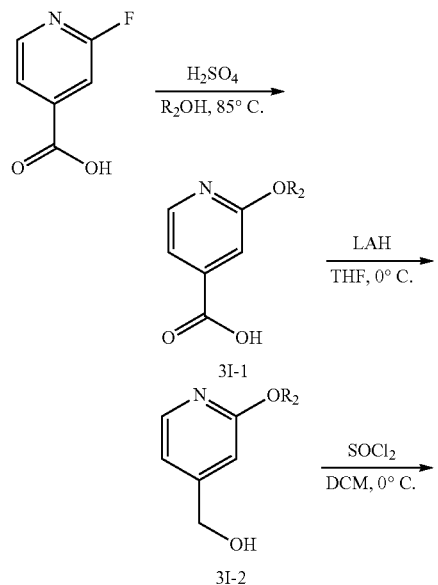

3-8: $R_2$ = Me
3-9: $R_2$ = Et
3-10: $R_2$ = i-Bu
3-11: $R_2$ = i-Pr

Preparation of Intermediate 3-10

First, $H_2SO_4$ (2.5 mL) was added to a mixture of 2-fluoroisonicotinic acid (5 g, 35.5 mmol, 1.0 eq) in 2-Methyl-1-propanol (75 mL). The mixture was stirred for 115° C. for 16 h. TLC analysis of the reaction mixture showed full conversion to the desired product. The reaction mixture was cooled to room temperature and concentrated under reduced pressure. The residue was added with saturated $NaHCO_3$ solution to adjust the pH=8 and extracted with ethyl acetate. The organic layer was washed with brine, dried over anhydrous $Na_2SO_4$ and concentrated under reduced pressure. The residue was purified by column chromatography on a silica gel to give compound 3I-1 (5 g, 56%).

To a mixture of compound 3I-1 (7 g, 25.8 mmol, 1.0 eq) in dry THF (100 mL) was quickly added LAH (1.96 g, 51.6 mmol, 2 eq) at 0° C. under nitrogen atmosphere. The mixture was stirred at 0° C. for 1 h. TLC analysis of the reaction mixture showed full conversion to the desired product. The reaction was quenched with $Na_2SO_4 \cdot 10H_2O$ (7 g, 21.7 mmol, 0.8 eq) and the mixture was stirred for 0.5 h. Then the mixture was filtered, and the organic layer was concentrated in vacuum. The residue was purified by column chromatography on silica gel (PE: EA, 3:1) to give compound 3I-2 (3 g, 60%).

To a mixture of compound 3I-2 (4 g, 18.5 mmol, 1.0 eq) in DCM (100 mL) was added $SOCl_2$ (2.7 mL, 37.1 mmol, 2.0 eq) drop wise at 0° C. under nitrogen atmosphere. The mixture was stirred at 0° C. for 1 h. The reaction mixture was concentrated under reduced pressure to give compound 3-10 (4.2 g, 95%).

Intermediates 3-8, 3-9 and 3-11 were synthesized by the same procedure as intermediate 3-10, except that 2-Methyl-1-propanol was replaced with methanol in the synthesis of intermediate 3-8, ethanol in the synthesis of intermediate 3-9 and i-propanol in the synthesis of intermediate 3-11.

Preparation of Compounds FC-17 and FC-18:

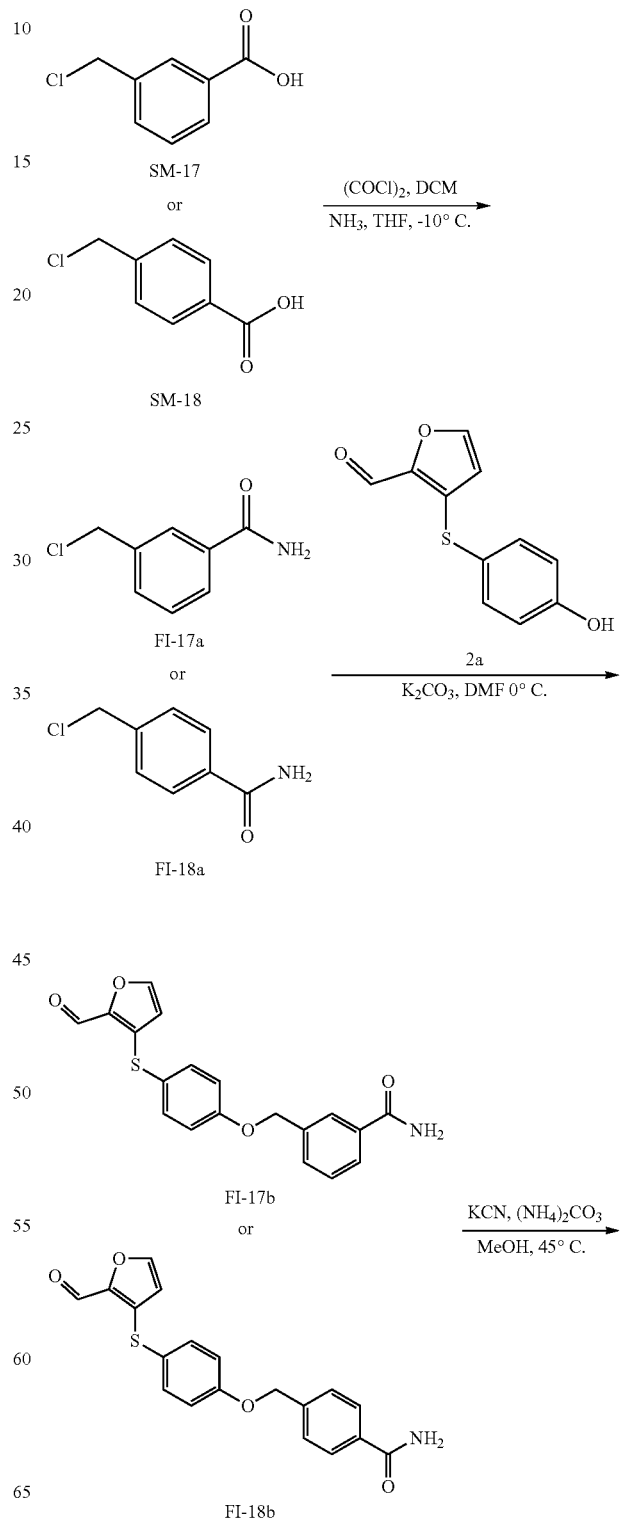

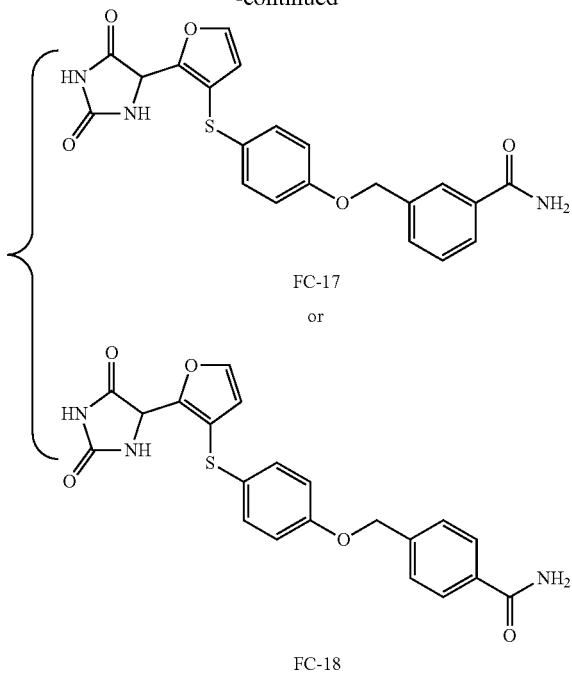

FC-17 or

FC-18

To a mixture of compound SM-17 (1.7 g, 0.01 mol, 1.0 eq) in DCM was added (COCl)₂ (2.5 g, 0.02 mol, 2.0 eq) drop wise at 0° C. The mixture was stirred for 1 h while the solution became clarified. Then the mixture was concentrated under reduced pressure. To a mixture of the residue in DCM was added a solution of NH₃ in THE at −10° C. The mixture was stirred for 0.5 h and then concentrated under reduced pressure to give compound FI-17a (1.3 g, 77%).

To a mixture of compound FI-17a (1.36 g, 5.92 mmol, 1.0 eq) in DMF (50 mL) was successively added compound 2a (1 g, 5.92 mmol, 1.0 eq) and K₂CO₃ (2.45 g, 17.76 mmol, 3.0 eq). The mixture was stirred at room temperature for 16 h under nitrogen atmosphere. TLC analysis of the reaction mixture showed full conversion to the desired product. Then the mixture was diluted with H₂O (100 mL) and extracted with EA (3×100 mL). The combined organic layers were washed with a saturated aqueous solution of NH₄Cl (3×100 mL), brine, dried over anhydrous Na₂SO₄ and concentrated under reduced pressure. The residue was purified by column chromatography on silica gel (PE/EA, 1:1) to give compound FI-17b (850 mg, 30%).

To a solution of compound FI-17b (850 mg, 2.41 mmol, 1.0 eq) in MeOH (10 mL) was added (NH₄)₂CO₃ (934 mg, 9.64 mmol, 4.0 eq) and KCN (313 mg, 4.82 mmol, 2.0 eq). The mixture was stirred at 45° C. for 16 h. Then, 3 M HCl was added to the reaction to adjust the pH=1 to 2 and stirred at room temperature for 1 h, then a saturated aqueous solution of NaHCO₃ was added to adjust the pH=6 to, 7 and the mixture was extracted with ethyl acetate. The organic layer was washed with brine, dried over anhydrous Na₂SO₄ and concentrated under reduced pressure. The residue was purified by Prep-TLC to give compound FC-17 (500 mg, 49%) as a white solid. Compound FC-18 was synthesized by the same procedure as the preparation of FC-17 except replaced SM-17 with SM-18 as starting material.

Preparation of Compound FC-19:

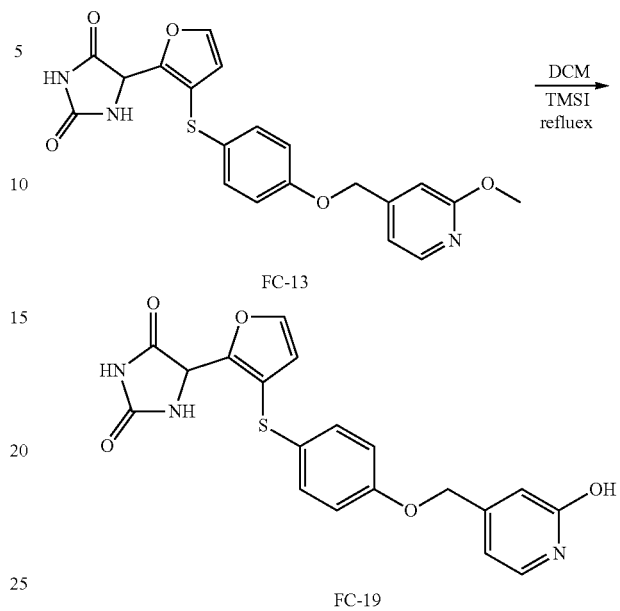

FC-13

FC-19

To a solution of compound FC-13 (500 mg, 1.21 mmol, 1.0 eq) in CHCl₃ (30 mL) was added TMS-I (1.7 mL, 12.1 mmol, 10.0 eq). The mixture was stirred at 55° C. for 16 h. The reaction mixture was cooled to room temperature and concentrated under reduced pressure. The residue was purified by prep-TLC (EA:MeOH, 10:1) to provide compound FC-19 (100 mg, 21%) as a white solid.

Preparation of Intermediates 3-12, 3-13, and 3-14

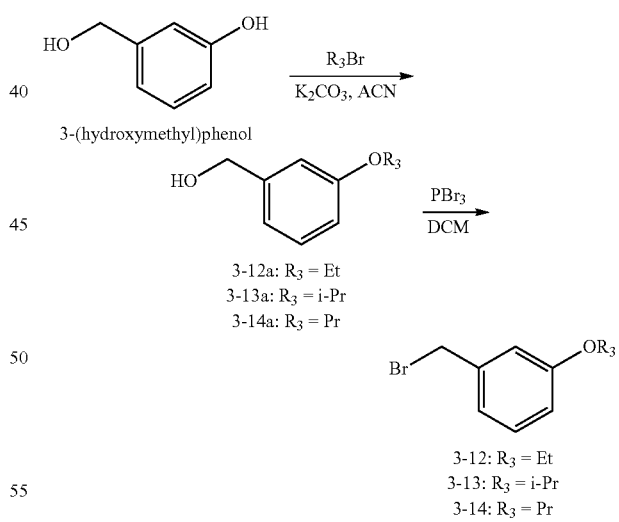

3-(hydroxymethyl)phenol 3-12a: R₃ = Et
3-13a: R₃ = i-Pr
3-14a: R₃ = Pr 3-12: R₃ = Et
3-13: R₃ = i-Pr
3-14: R₃ = Pr A solution of 3-(hydroxymethyl)phenol (0.5 g, 4.0 mmol), bromoethane (0.86 g, 8 mmol), and K₂CO₃ (2.2 g, 16 mmol) in ACN (20 mL) was stirred at r.t. overnight. The reaction mixture was added with water and EA, and extracted with EA twice. The combined organic layer was dried with MgSO₄, and evaporated under high vacuum. The residue was purified by flash chromatography with EA/Hex (EA/Hex=1:4) to give intermediate 3-12a as an oil (0.48 g, 79%).

To a solution of intermediate 3-12a (0.18 g, 1.1 mmol) in DCM (20 mL) was added PBr₃ (0.15 mL, 1.5 mmol, 33% in acetic acid). The reaction mixture was stirred at r.t. for 1 hour, added with DCM and water, and extracted with DCM twice. The combined organic layer was dried with MgSO₄ and evaporated under high vacuum. The residue was purified by flash chromatography with EA/Hex (EA/Hex=1:4) to give a white solid of intermediate 3-12 (0.16 g, 63%). Intermediates 3-13 and 3-14 were synthesized by the same procedure as the preparation of intermediate 3-12 except that bromoethane was replaced with 2-bromopropane or 1-bromopropane as starting material.

Preparation of Intermediates 3-15, 3-16, and 3-17:

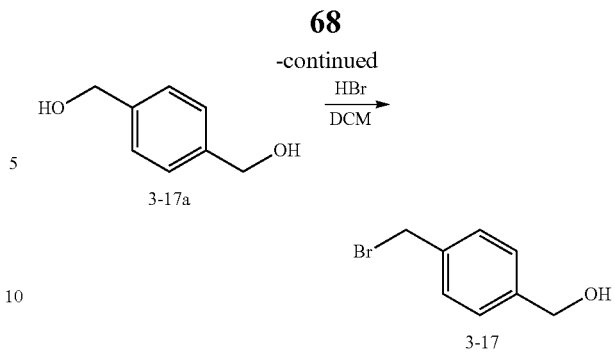

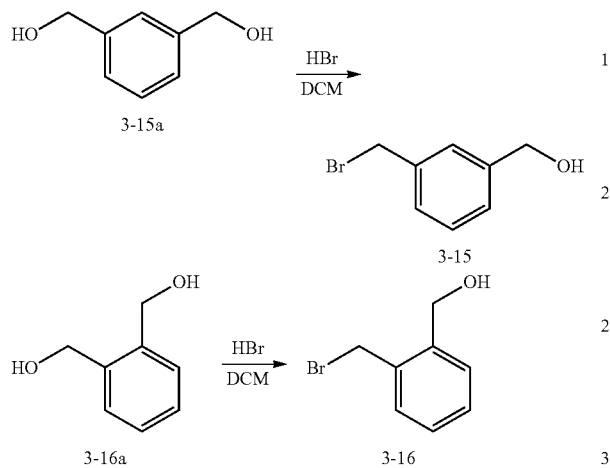

To a solution of 1,4-benzenedimethanol (0.14 g, 1 mmol) in DCM (5 mL) was added HBr (33% in acetic acid, 0.18 mL, 1 mmol) dropwise. The reaction mixture was stirred at r.t. for 1 hour. It was determined by TLC that the spot for the starting material (SM) disappeared. The reaction mixture was added with EA and water, and extracted EA twice. The combined organic layer was dried with MgSO₄, and evaporated under high vacuum. The residue was purified by flash chromatography with EA/Hex (EA/Hex=1:10 to 1:4) to give a white solid of intermediate 3-15 (0.4 g, 52%). The intermediates 3-16 and 3-17 were synthesized by the same procedure except that intermediate 3-15a was replaced with intermediate 3-16a or 3-17a as starting materials.

General Scheme to Prepare Compound FC-20 to FC-25:

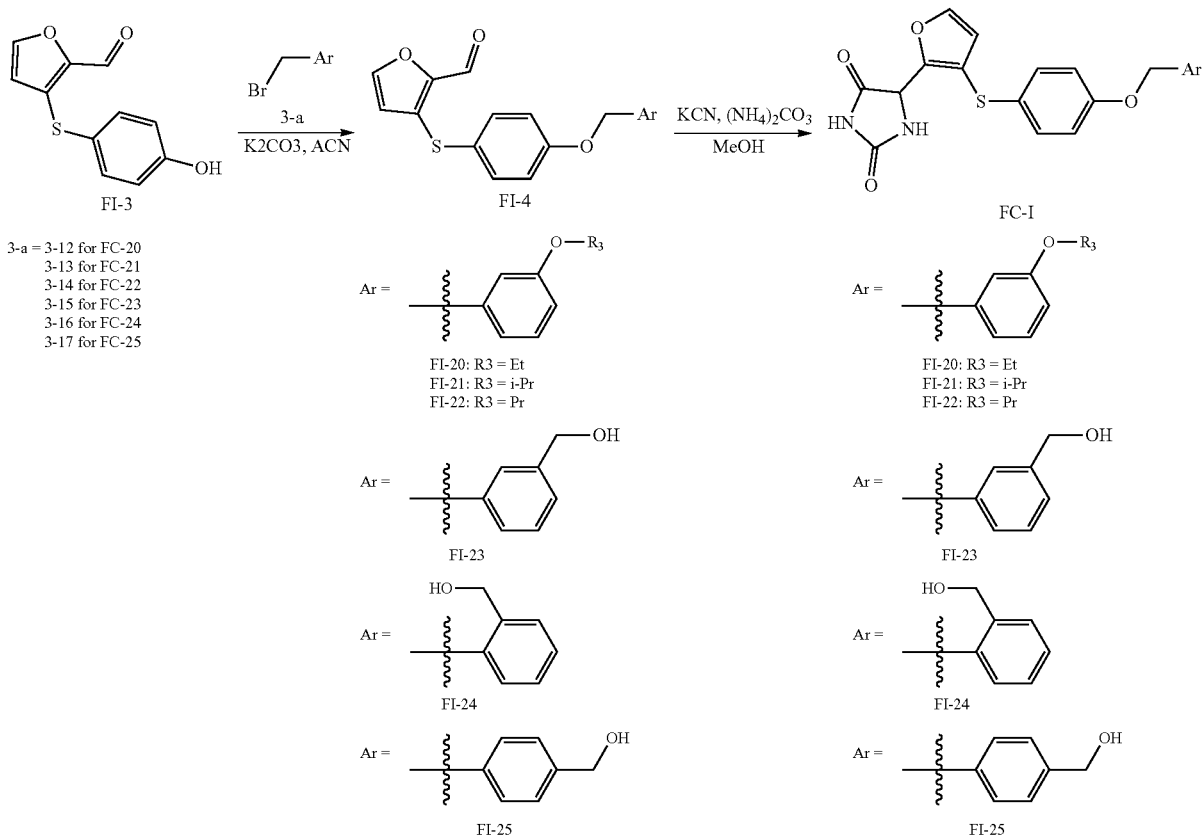

To a solution of 1-Bromomethyl-3-ethoxy-benzene 3-12 (0.42 g, 1.96. mmol), FI-3 (0.43 g, 1.96. mmol), and K$_2$CO$_3$ (0.83 g) in ACN was stirred at r.t. overnight. The reaction was checked by TLC (EA/Hex=1/3), and it was determined that the benzyl bromide spot disappeared. The reaction mixture was added with EA and water, and extracted with EA twice. The combined organic layer was dried with MgSO$_4$, and purified on a silica gel column to yield the intermediate FI-20 (0.52 g, 60%). Intermediates FI-21, FI-22, FI-23, FI-24 and F1-25 were synthesized using the same procedure except that the starting material 3-12 was replaced with starting materials 3-13, 3-14, 3-15, 3-16 or 3-17, accordingly.

To a solution of FI-20 (0.52 g, 1.41 mmol) in EtOH/H$_2$O (10 mL/5 mL) was added (NH$_4$)$_2$CO$_3$ (2.01 g, 21.0 mmol) and KCN (0.16 g, 2.31 mmol). The reaction mixture was stirred at r.t. overnight. The solution was evaporated to remove most of the solvent. The mixture was added with water and then extracted with EA twice. The organic layers were combined, dried with MgSO$_4$ and evaporated. The residue was purified by flash chromatography with EA/Hexane (EA/Hexane=1:1) to yield FC-20 as a light yellow solid (0.22 g, 38%). Compounds FC-21, FC-22, FC-23, FC-24 and FC-25 were synthesized by the same procedure except that intermediate F1-20 was replaced with intermediates FI-21, FI-22, FI-23, F1-24 or F1-25, accordingly.

Preparation of Compound FC-26:

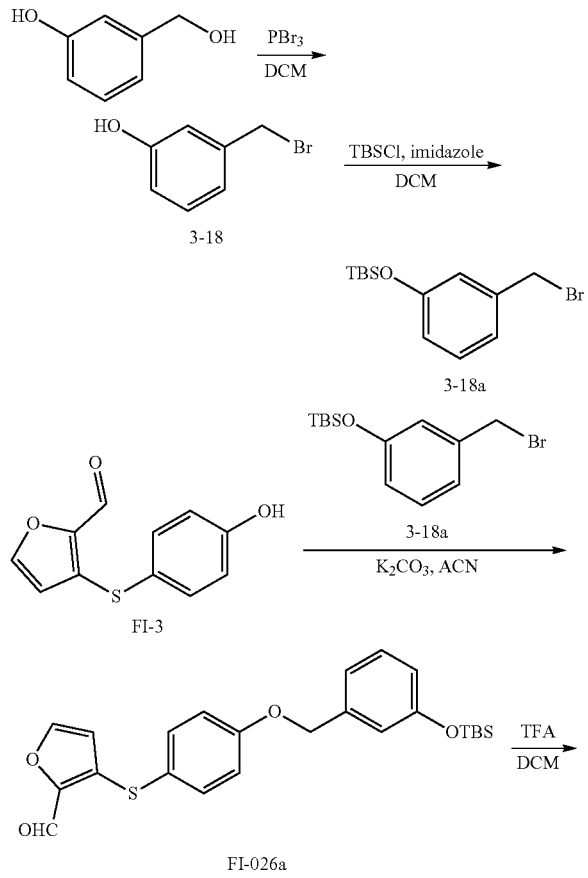

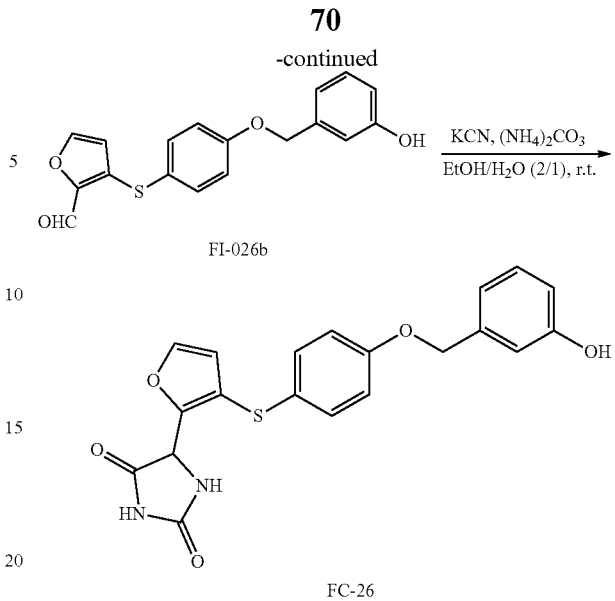

FC-26

To a solution of 3-hydroxybenzyl alcohol (1.5 g, 12.1 mmol) in DCM (45 mL) was added PBr$_3$ (1.5 mL, 15.8 mmol) dropwise in an ice bath. The mixture was stirred at r.t. for 1 hour. The progress of the reaction to completion was monited by TLC (EA/Hex=1/10). The reaction mixture was then added with DCM and water, and extracted with DCM twice. The combined organic layer was filter with silica gel and MgSO$_4$, and evaporated under high vacuum. The white solid intermediate 3-18 was used for next step without further purification (1.27 g, 57%).

To a solution of intermediate 3-18 (1.27 g, 6.79 mmol) and imidazole (0.92 g, 13.58 mmol) in DCM (30 mL) was added a solution of TBSCl in DCM (1.53 g, 10.2 mmol, 5 mL) dropwise at r.t. The reaction mixture was stirred at r.t. overnight. The reaction mixture was added with DCM and water, and extracted with DCM twice. The combined organic layer was dried with MgSO$_4$, filtered with silica gel and evaporated under high vacuum. The oily compound 3-18a was used in the next step without further purification (1.7 g, 84%).

A solution of compound 3-18a (1.7. g, 5.8. mmol), compound FI-3 (1.28 mg, 5.8 mmol) and K$_2$CO$_3$ (3.5. g, 22. mmol) in ACN (10 mL) was stirred at r.t. for overnight. The reaction mixture was added with water and EA, and extracted with EA twice. The combined organic layer was dried with MgSO$_4$, and evaporated under high vacuum. The residue was purified by flash chromatography with EA/Hex (EA/Hex=1:4) to afford compound FI-026a (1.2 g, 47%).

To a solution of compound FI-026a (1.03 g) in DCM (25 mL) was added TFA (1 mL) dropwise at r.t. The reaction mixture was stirred overnight, and then the solvent and TFA were removed. The brown oil was added with NaHCO$_3$ and MeOH. Then the solvent was removed again. The residue was purified by flash chromatography with EA/Hex (EA/Hex=1:4) to give white solid FI-026b (0.14 g).

To a solution of compound FI-026b (0.2 g, 0.61 mmol) in EtOH/H$_2$O (5 mL/2.5 mL) was added (NH$_4$)$_2$CO$_3$ (0.35 g, 3.66 mmol) and KCN (47 mg, 0.74 mmol). The reaction mixture was stirred at r.t. overnight. The solution was evaporated to remove most of the solvent. The mixture was added with water and EA, and then extracted with EA twice. The organic layers were combined, dried with MgSO$_4$ and evaporated under high vacuum. The residue was purified by flash chromatography with DCM/MeOH (DCM/MeOH=20:1) to give compound FC-26 as a white solid (0.11 g, 45%).

Preparation of Compound FC-27:

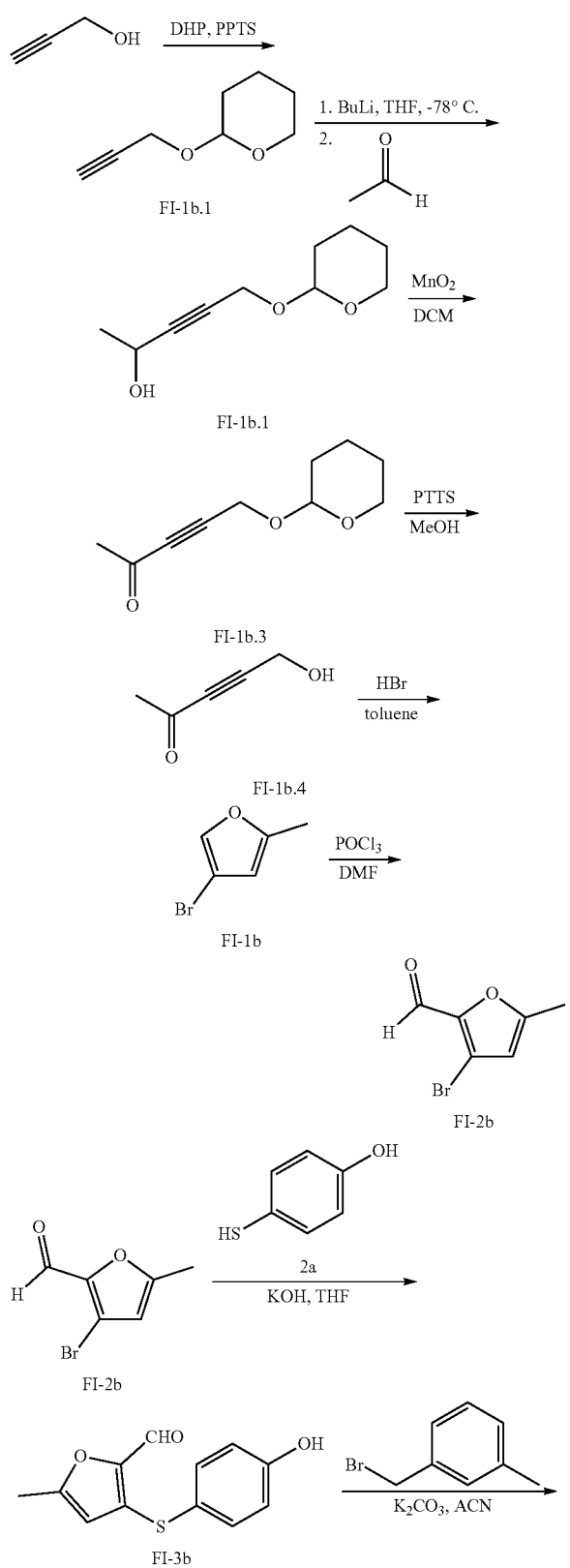

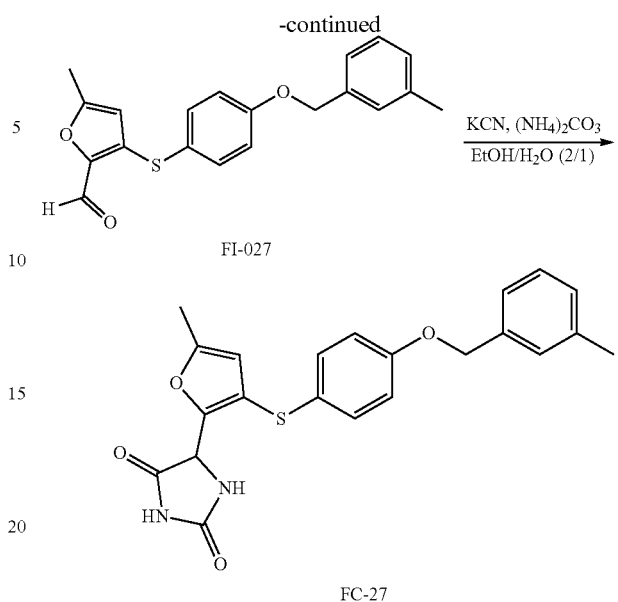

A mixture of propargyl alcohol (0.6 ml, 103.82 mmol), DHP (1.2 ml, 13.5 mmol) and PPTS (21 mg, 0.1 mmol, 1 mol %) were stirred for 1 h at 0° C. The reaction mixture was directly purified by silica gel column chromatography (Hex:$Et_2O$, 30:1) to give FI-1b.1 (11 g, 78%).

To a stirred solution of THP-protected propargylic alcohol FI-1b.1 (0.52 g, 3 mmol) in THE (15 mL), n-BuLi solution (1.5 mL, 3.6 mmol, 2.5 M in Hexane) was added at −78° C. The reaction was stirred for 30 min, follow by addition of acetaldehyde (0.18 mL, 3.3 mmol). The mixture was stirred for 2 h, and then 0° C. for 30 min. The reaction mixture was extracted with ether/$NH_4Cl$(sat.), and concentrated to give oily FI-1b.2 (0.12 g, 22%).

To a stirred solution of FI-1b.2 (0.12 g, 0.65 mmol) in DCM (5 mL) was added $MnO_2$ (67 mg, 0.78 mmol) at 0° C. overnight. TLC evaluation of the reaction indicated that starting material remained. Then, additional $MnO_2$ (0.15 g) was added, and the solution was stirred for an additional 16 hours. The reaction mixture was filtered with $MgSO_4$ and silica gel. The residue was purified by flash chromatography with EA/Hex (EA/Hex=1:4) to give oily FI-1b.3 (0.1 g, 90%).

To a stirred solution of FI-1b.3 (1.8 g, 10 mmol) in MeOH (50 mL) was added PPTS (0.5 g). The reaction mixture was stirred overnight at r.t. The mixture was diluted with $H_2O$ and EA. The aqueous phase was extracted with EA, the combined organic fractions were washed with brine, and the solvents were removed. The residue was purified by flash chromatography with EA/Hex (EA/Hex=3:1) to give yellow liquid FI-1b.4 (1 g, ~100%).

To a stirred solution of FI-1b.4 (0.1 g, 1 mmol) in toluene (5 mL) was added HBr (1 mL, 2 M $HBr_{(aq)}$) at r.t. The mixture was diluted with toluene and water. The aqueous phase was extracted with toluene. The combined organic fractions were washed with brine. The crude NMR of the toluene solution was checked, which indicated that the desired product FI-1b (0.15 g) was present. The toluene solution of FI-1b was used in the next step without further purification.

$POCl_3$ (0.1 mL, 1.1 mmol) was added dropwise to DMF (1 mL) at r.t. A solution of F1-1b (0.15 g) in toluene (5 mL) was added to the DMF/$POCl_3$ solution with stirring. After two hours, the reaction mixture was neutralized with NaHCO$_3$ $_{(sat.\ aq.)}$ and stirred for 30 mins. The aqueous phase was extracted with EA, the organic phase liquids were combined, washed with brine, dried over MgSO$_4$ and the solvent was removed. The crude NMR was checked, which indicated that the desired product FI-2b (0.18 g) was present. FI-2b was used in the next step without further purification. To a solution of FI-2b (0.18 g) in THF (5 mL) was added NaOH (60 mg) and 4-mercaptophenol (0.13 g, 1 mmol), and the reaction mixture was stirred overnight. The reaction mixture was extracted with EA and water, washed with brine, dried over MgSO$_4$ and the solvent was removed. The residue was purified by flash chromatography with EA/Hex (EA/Hex=1/4) to give the desired product FI-3b (0.14 g, 60%) as an intermediate for the synthesis of FC-27 and FC-28.

A solution of FI-3b (0.3 g, 1.28 mmol), 3-methyl benzyl bromide (0.3 mg, 1.92 mmol), and K$_2$CO$_3$ (0.71 g, 5.12 mmol) in ACN (6 mL) was stirred at r.t. overnight. The reaction mixture was added with water and EA, and extracted with EA twice. The combined organic layer was dried with MgSO$_4$, and evaporated under high vacuum. The residue was purified by flash chromatography with EA/Hex (EA/Hex=1:4) to give a yellow oil FI-027 (0.34 g, 79%).

To a solution of FI-027 (0.34 g, 1.0 mmol) in EtOH/H$_2$O (5 mL/2.5 mL) was added (NH$_4$)$_2$CO$_3$ (0.58 g, 6 mmol) and KCN (78 mg, 1.2 mmol). The reaction mixture was stirred at r.t. overnight. The solution was evaporated to remove most of the solvent. The mixture was added with water and EA, and then extracted with EA twice. The organic layers were combined, dried with MgSO$_4$ and evaporated under high vacuum. The residue was purified by flash chromatography with DCM/MeOH (DCM/MeOH=50:1-30:1) to give FC-27 as a yellow solid (105 mg, 25%).

Preparation of Compound FC-28:

A solution of FI-3b (0.3 g, 1.28 mmol), 3-15 (0.3 mg, 1.92 mmol), K$_2$CO$_3$ (0.71 g, 5.12 mmol) in ACN (6 mL) was stirred at r.t. for overnight. The reaction mixture was added with water and EA, and extracted with EA twice. The combined organic layer was dried with MgSO$_4$, and evaporated under high vacuum. The residue was purified by flash chromatography with EA/Hex (EA/Hex=1:4) to give a yellow oil FI-028 (0.34 g, 79%).

To a solution of FI-028 (0.34 g, 1.0 mmol) in EtOH/H$_2$O (5 mL/2.5 mL) was added (NH$_4$)$_2$CO$_3$ (0.58 g, 6 mmol) and KCN (78 mg, 1.2 mmol). The reaction mixture was stirred at r.t. overnight. The solution was evaporated to remove most of the solvent. The mixture was added with water and EA, and then extracted with EA twice. The organic layers were combined, dried with MgSO$_4$ and evaporated under high vacuum. The residue was purified by flash chromatography with DCM/MeOH (DCM/MeOH=50:1-30:1) to give FC-28 as a yellow solid (105 mg, 25%).

Preparation of Compound FC-29:

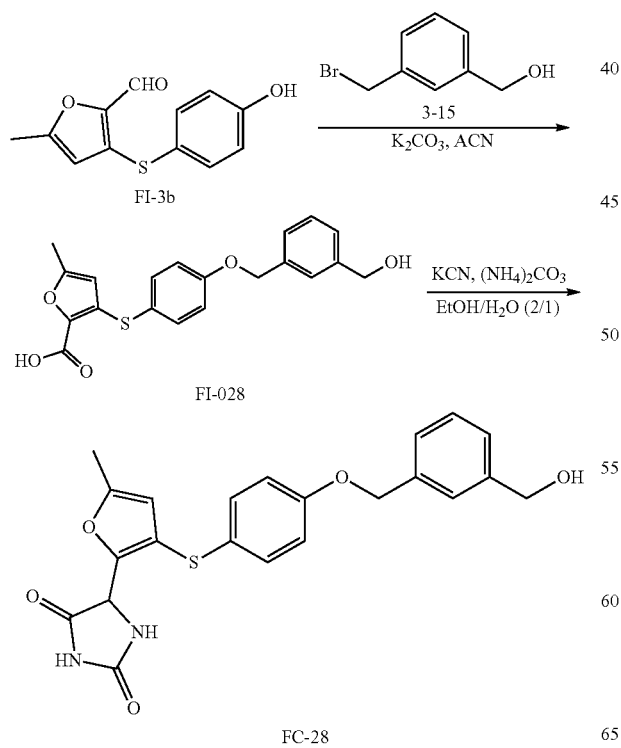

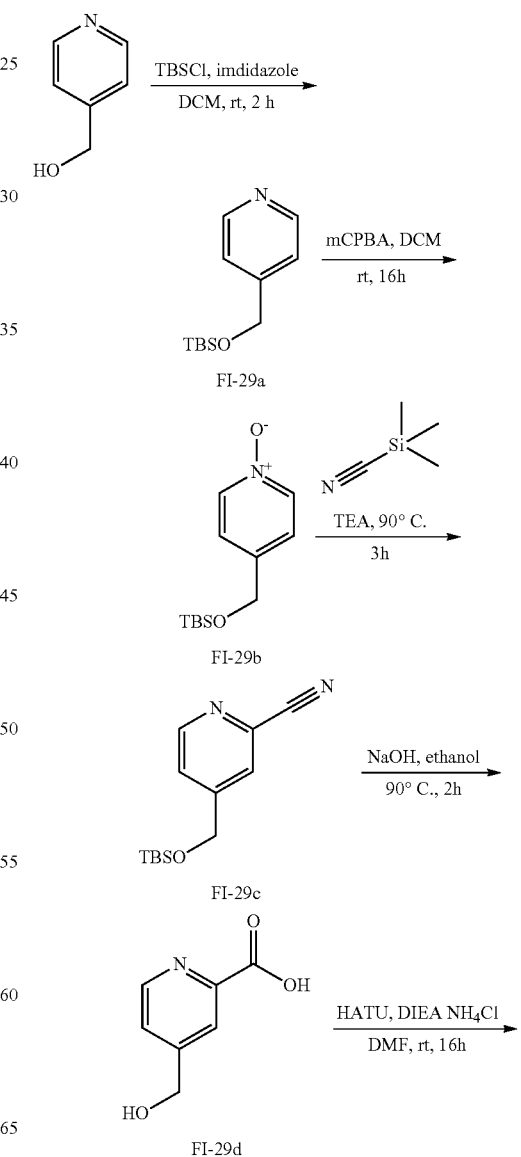

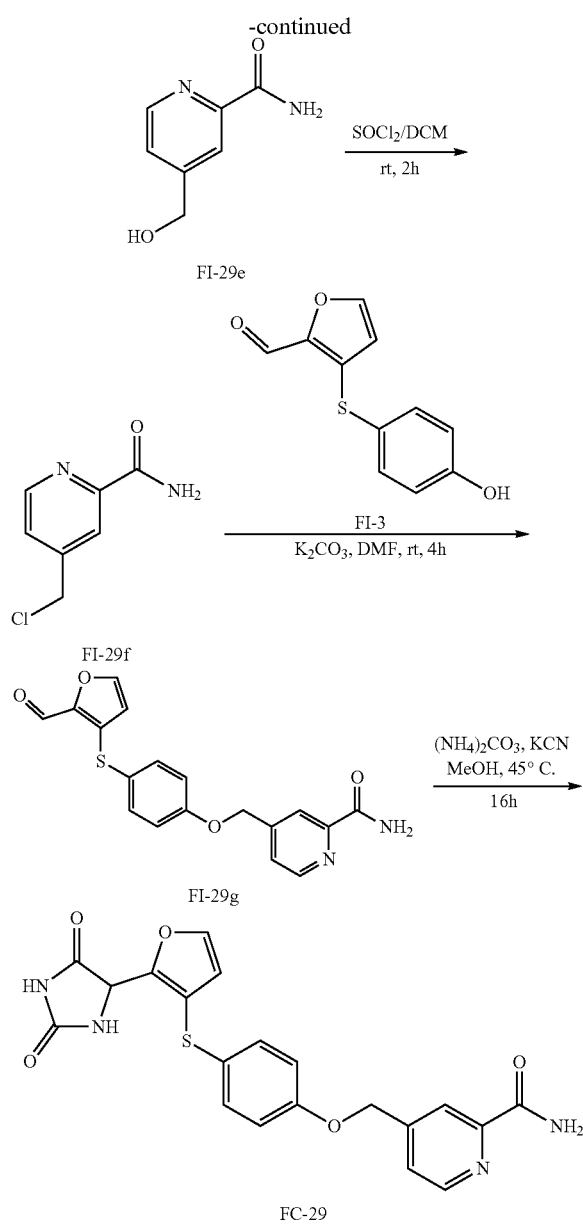

sure. The residue was purified by silica gel chromatography to afford compound F1-29b (8.1 g, 75%).

To a mixture of compound FI-29b (10.3 g, 43.4 mmol, 1.0 eq) in TEA (40 mL) was added trimethylsilyl cyanide (13 g, 130.4 mmol, 3 eq). The mixture was heated at 90° C. for 3 h under nitrogen atmosphere. Then the mixture was concentrated under reduced pressure. The residue was purified by silica gel chromatography to give FI-29c (5.1 g, 47%).

To a solution of FI-29c (5.1 g, 20.53 mmol, 1.0 eq) in ethanol/H₂O (100/17 mL) was added NaOH (6.9 g, 172.5 mmol, 8.4 eq). The mixture was stirred at 90° C. for 2 h. Then the mixture was cooled to room temperature and diluted with water (100 mL) and extracted with ethyl acetate. The aqueous layer was acidified to pH=4-5 and extracted with ethyl acetate. The organic layer was washed with brine, dried over anhydrous Na₂SO₄ and concentrated under reduced pressure. The residue was purified by silica gel chromatography to afford FI-29d (3.2 g, 99%).

To a solution of FI-29d (2.2 g, 14.36 mmol, 1.0 eq) in DMF (100 mL) was successively added NH₄Cl (1.54 g, 28.73 mmol, 2.0 eq), HATU (5.46 g, 14.36 mmol, 1.0 eq) and DIEA (5.57 g, 43.08 mmol, 3.0 eq). The mixture was stirred at room temperature for 16 h. The reaction mixture was diluted with ethyl acetate (200 mL) and washed with brine, water, dried over anhydrous Na₂SO₄ and concentrated under reduced pressure. The residue was purified by silica gel chromatography to afford FI-29e (0.6 g, 27%).

To a mixture of FI-29e (0.53 g, 3.48 mmol, 1.0 eq) in DCM (50 mL) was added SOCl₂ (0.83 g, 6.96 mmol, 2.0 eq) drop wise at 0° C. under nitrogen atmosphere. The mixture was stirred at room temperature for 2 h. The reaction mixture was diluted with DCM (50 mL) and washed with a saturated aqueous solution of NaHCO₃, brine, dried over anhydrous Na₂SO₄ and concentrated under reduced pressure to afford FI-29f (0.47 g, 79%).

To a solution of FI-29f (470 mg, 2.75 mmol, 1.0 eq) in DMF (20 mL) was added FI-3 (607 mg, 2.75 mmol, 1.0 eq) and K₂CO₃ (759 mg, 5.5 mmol, 2 eq). The mixture was stirred at room temperature for 4 h. Then the mixture was diluted with water (50 mL) and extracted with ethyl acetate (30 mL×3). The organic layer was washed with brine, dried over anhydrous Na₂SO₄ and concentrated under reduced pressure. The residue was purified by silica gel chromatography to afford FI-29 g (210 mg, 22%).

To a solution of FI-29 g (250 mg, 0.71 mmol, 1.0 eq) in MeOH (7 mL) was added (NH₄)₂CO₃ (270 mg, 2.82 mmol, 4.0 eq) and KCN (91 mg, 1.41 mmol, 2.0 eq). The mixture was stirred at 45° C. for 16 h. The reaction was added with 3 M HCl to adjust pH=1-2 and stirred at room temperature for 1 h, then a saturated aqueous solution of NaHCO₃ was added to adjust pH=7-8 and extracted with ethyl acetate. The organic layer was washed with brine, dried over anhydrous Na₂SO₄ and concentrated under reduced pressure. The residue was purified by silica gel chromatography to give FC-29 (75 mg, 25%) as a white solid.

Preparation of Compound FC-30:

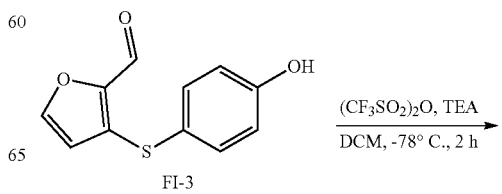

To a solution of compound 4-Pyridinemethanol (5 g, 45.82 mmol, 1.0 eq) and imidazole (7.97 g, 137.45 mmol, 3.0 eq) in DCM (100 mL) was added TBSCl (13.8 g, 91.64 mmol, 2.0 eq) at 0° C. The mixture was stirred at room temperature for 2 h. Then the mixture was quenched with saturated NH₄Cl solution (100 mL). The mixture was extracted with ethyl acetate (50 mL×3). The combined organic phases were washed with brine, dried over anhydrous Na₂SO₄ and concentrated under reduced pressure. The residue was purified by silica gel chromatography to afford compound FI-29a (7.2 g, 70%).

To a solution of compound FI-29a (10 g, 44.76 mmol, 1.0 eq) in DCM (150 mL) was added m-CPBA (11.58 g, 67.14 mmol, 1.5 eq) at room temperature. The mixture was stirred at room temperature for 16 h. TLC analysis of the reaction mixture showed full conversion to the desired product. Then the mixture was quenched with saturated aqueous of sodium sulfite. The organic layer was washed with brine, dried over anhydrous Na₂SO₄ and concentrated under reduced pres- -continued

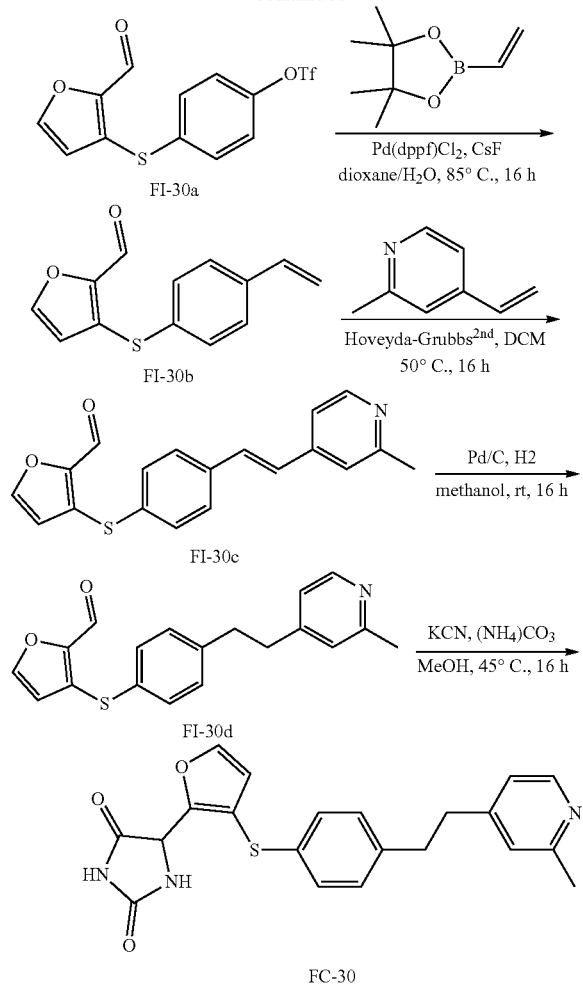

To a solution of compound FI-3 (13.9 g, 63.11 mmol, 1.0 eq) in DCM (500 mL) was added TEA (20.63 g, 189.34 mmol, 3 eq), (CF$_3$SO$_2$)$_2$O (19.59 g, 69.42 mmol, 1.1 eq) at −78° C. under nitrogen atmosphere. The mixture was stirred at −78° C. for 2 h under nitrogen atmosphere. Then the mixture was warmed to 0° C. and quenched with saturated Na$_2$CO$_3$ (200 mL) solution. The organic phases were washed with brine, dried over anhydrous Na$_2$SO$_4$ and concentrated under reduced pressure. The residue was purified by silica gel chromatography to afford compound FI-30a (9.7 g, 44%).

To a solution of FI-30a (2.5 g, 7.12 mmol, 1.0 eq) in dioxane/H$_2$O (5/1, 60 mL) was successively added 4,4,5,5-tetramethyl-2-vinyl-1,3,2-dioxaborolane (1.2 g, 7.83 mmol, 1.1 eq), Pd(dppf)$_2$Cl$_2$ (0.52 g, 0.71 mmol, 0.1 eq) and CsF (2.8 g, 15.45 mmol, 2 eq) under nitrogen atmosphere. The mixture was stirred at 85° C. for 16 h. Then the reaction was cooled to room temperature and quenched with H$_2$O (50 mL) and extracted with ethyl acetate (30 mL×3). The combined organic phases were washed with brine, dried over anhydrous Na$_2$SO$_4$ and concentrated under reduced pressure. The residue was purified by silica gel chromatography to afford FI-30b (1.3 g, 79%).

To a solution of FI-30b (1.3 g, 5.65 mmol, 1.0 eq) in DCM (50 mL) was added 2-methyl-4-vinylpyridine (0.74 g, 6.21 mmol, 1.1 eq) and Hoveyda-Grubbs II reagent (354 g, 0.57 mmol, 0.1 eq). The mixture was stirred at 50° C. for 14 h under nitrogen atmosphere. Then the mixture was diluted with DCM (100 mL) and washed with brine, dried over anhydrous Na$_2$SO$_4$ and concentrated under reduced pressure. The residue was purified by silica gel chromatography to afford FI-30c (0.3 g, 16%).

To a solution of FI-30c in methanol is added Pd/C. The mixture is stirred under hydrogen atmosphere (20 psi) at room temperature for 16 h. The mixture is filtered and the filtrate is concentrated and purified to obtain FI-30d.

To a solution of FI-30d is added (NH$_4$)$_2$CO$_3$ and KCN. The mixture is stirred at 45° C. for about 16 h. Then, 3 M HCl is added to adjust pH=1-2 at room temperature for 1 h, then a saturated aqueous solution of NaHCO$_3$ is added to adjust pH=7-8. The mixture is extracted and the residue purified by silica gel chromatography to give FC-30.

Preparation of Compound FC-31:

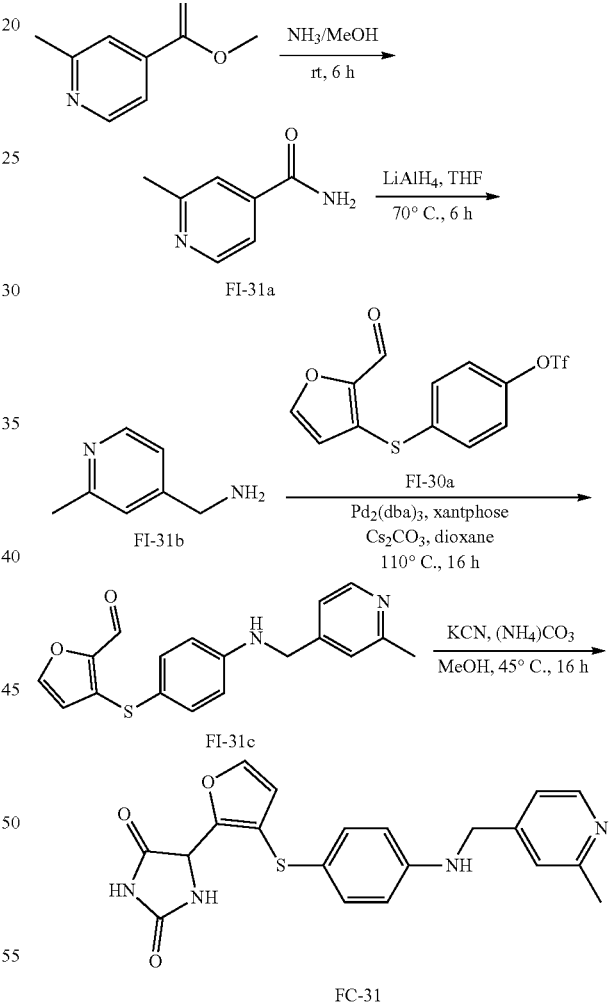

The starting material methyl 2-methylisonicotinate (20 g, 132.31 mmol, 1.0 eq) was dissolved in NH$_3$/MeOH (100 mL, 500 mmol, 3.78 eq, 5M) and stirred at room temperature for 6 h under nitrogen atmosphere. The mixture was concentrated under reduced pressure. The residue was purified by silica gel chromatography to afford FI-31a (10.2 g, 56%).

To a mixture of FI-31a (7.65 g, 56.18 mmol, 1.0 eq) in THF (250 mL) was added LiAlH$_4$ (6.4 g, 168.56 mmol, 3 eq) at 0° C. under nitrogen atmosphere. The mixture was stirred at 70° C. for 6 h. Then the mixture was cooled to 0° C. and quenched with saturated Na₂SO₄ solution (100 mL). The mixture was filtered and the filtrate was extracted with DCM (3×30 mL). The combined organic phases were washed with brine, dried over anhydrous Na₂SO₄ and concentrated under reduced pressure. The residue was purified by silica gel chromatography to afford FI-31b (0.9 g, 13%).

To a solution of FI-30a (400 mg, 1.13 mmol, 1.0 eq) and FI-31b (183 mg, 1.13 mmol, 1.0 eq) in dioxane (20 mL) was successively added xantphose (65 mg, 0.11 mmol, 0.1 eq), Pd₂(dba)₃ (103 mg, 0.11 mmol, 0.1 eq) and C₂CO₃ (1.1 g, 3.4 mmol, 3 eq) under nitrogen atmosphere. The mixture was stirred at 110° C. for 16 h under nitrogen atmosphere. Then the mixture was quenched with H₂O (50 mL) and extracted with ethyl acetate (100 mL×3). The combined organic phases were washed with brine, dried over anhydrous Na₂SO₄ and concentrated under reduced pressure. The residue was purified by silica gel chromatography to afford FI-31c (80 mg, 22%).

To a solution of FI-31c (180 mg, 0.55 mmol, 1.0 eq) in MeOH (5 mL) was added (NH₄)₂CO₃ (213 mg, 2.22 mmol, 4.0 eq) and KCN (72 mg, 1.11 mmol, 2.0 eq). The mixture was stirred at 45° C. for 16 h. The reaction was added with 3 M HCl to adjust pH=1-2 and stirred at room temperature for 1 h, then a saturated aqueous solution of NaHCO₃ was added to adjust pH=7-8 and extracted with ethyl acetate. The organic layer was washed with brine, dried over anhydrous Na₂SO₄ and concentrated under reduced pressure. The residue was purified by silica gel chromatography to give FC-31 (33 mg, 15%) as a yellow solid.

Preparation of Compound FC-32:

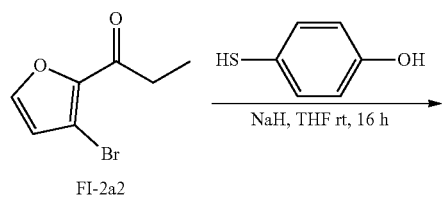

FI-2a2

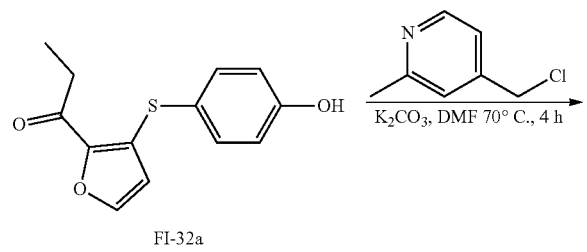

FI-32a

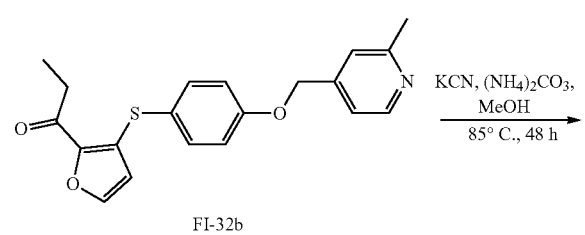

FI-32b

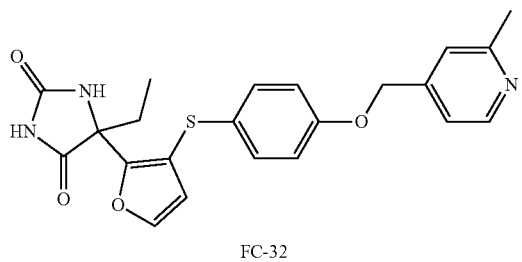

FC-32

To a mixture of FI-2a2 (600 mg, 2.97 mmol, 1.0 eq) and 4-mercaptophenol (450 mg, 2.97 mmol, 1.0 eq) in THF (10 mL) was added NaH (143 mg, 3.56 mmol, 1.2 eq) at 0° C. The mixture was allowed to warm to room temperature and stirred for 16 h under nitrogen atmosphere. Then the mixture was concentrated to half the amount of solvent and then 2 N HCl was added to adjust pH=6, filtered and the filtrate was concentrated. The residue was purified by column chromatography on a silica gel to give compound FI-32a (750 mg, 99%).

To a mixture of FI-32a (680 mg, 2.62 mmol, 1.0 eq) and 4-(chloromethyl)-2-methylpyridine (557 mg, 3.94 mmol, 1.5 eq) in DMF (20 mL) was added K₂CO₃ (1.08 g, 7.87 mmol, 3 eq). The mixture was stirred at 70° C. for 4 h under nitrogen atmosphere. Then the mixture was quenched with H₂O (60 mL) and extracted with ethyl acetate (40 mL×3). The combined organic phases were washed with brine, dried over anhydrous Na₂SO₄ and concentrated under reduced pressure. The residue was purified by silica gel chromatography to afford FI-32b (740 mg, 80%).

To a solution of FI-32b (800 mg, 2.26 mmol, 1.0 eq) in MeOH (20 mL) was added (NH₄)₂CO₃ (870 mg, 9.06 mmol, 4.0 eq) and KCN (294 mg, 4.5 mmol, 2.0 eq). The mixture was stirred at 45° C. for 16 h. The reaction was added 3 M HCl to adjust pH=1-2 and stirred at room temperature for 1 h, then saturated aqueous of NaHCO₃ was added to adjust pH=7-8 and extracted with ethyl acetate. The organic layer was washed with brine, dried over anhydrous Na₂SO₄ and concentrated under reduced pressure. The residue was purified by silica gel chromatography to give FC-32 (720 mg, 75%) as a white solid.

Preparation of Compound FC-33:

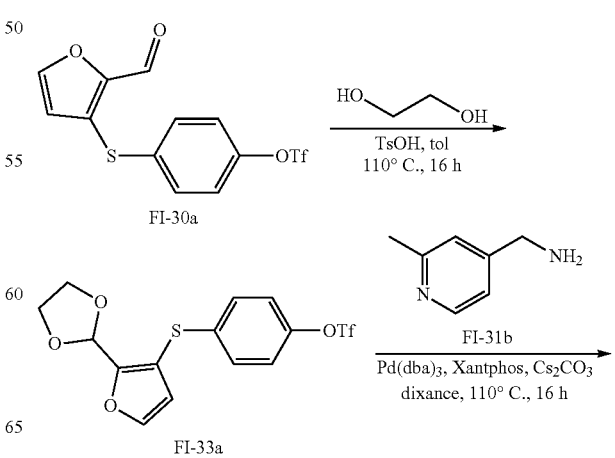

FI-30a

FI-31b

FI-33a

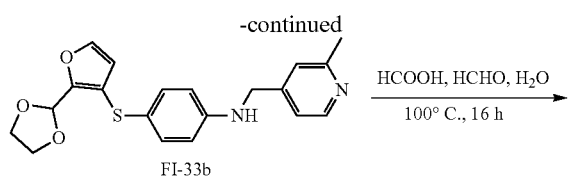

FI-33b

HCOOH, HCHO, H₂O
100° C., 16 h

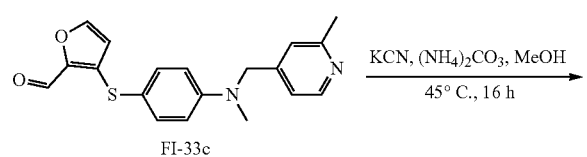

FI-33c

KCN, (NH₄)₂CO₃, MeOH
45° C., 16 h

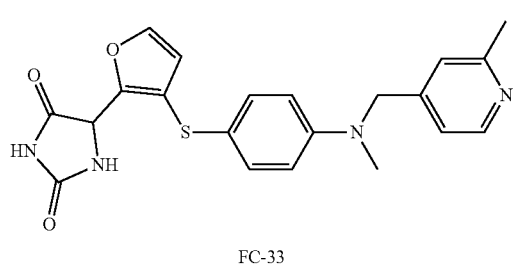

FC-33

To a solution of FI-30a (7.0 g, 19.87 mmol, 1.0 eq) in toluene (100 mL) was successively added ethane-1,2-diol (24.6 g, 397.3 mmol, 20 eq) and TsOH (0.16 g, 0.99 mmol, 0.05 eq). The mixture was heated under reflux for 12 h under nitrogen atmosphere. Then the mixture was concentrated under reduced pressure. The residue was purified by column chromatography on a silica gel to give FI-33a (3.78 g, 48%).

To a solution of FI-33a (3.78 g, 9.53 mmol, 1.0 eq) and FI-31b (1.16 g, 9.53 mmol, 1.0 eq) in dioxane (100 mL) was successively added xantphose (561 mg, 0.95 mmol, 0.1 eq), Pd₂(dba)₃ (889 mg, 0.95 mmol, 0.1 eq) and C₂CO₃ (9.31 g, 28.59 mmol, 3 eq) under nitrogen atmosphere. The mixture was stirred at 110° C. for 16 h under nitrogen atmosphere. Then the mixture was quenched with H₂O (50 mL) and extracted with ethyl acetate (100 mL*3). The combined organic phases were washed with brine, dried over anhydrous Na₂SO₄ and concentrated under reduced pressure. The residue was purified by silica gel chromatography to afford FI-33b (800 mg, 22%).

To a solution of FI-33b (800 mg, 2.17 mmol, 1.0 eq) in formic acid (10 mL, 40%) was added formaldehyde (13 mg, 4.34 mmol, 2.0 eq). The mixture was stirred at 100° C. for 16 h under nitrogen atmosphere. Then the mixture was concentrated under reduced pressure, diluted with aqueous NaHCO₃ and extracted with ethyl acetate (100 mL*3). The combined organic phases were washed with brine, dried over anhydrous Na₂SO₄ and concentrated under reduced pressure. The residue was purified by silica gel chromatography to afford FI-33c (180 mg, 24%).

To a solution of FI-33c (300 mg, 0.89 mmol, 1.0 eq) in MeOH (5 mL) was added (NH₄)₂CO₃ (340 mg, 3.54 mmol, 4.0 eq) and KCN (115 mg, 1.77 mmol, 2.0 eq). The mixture was stirred at 45° C. for 16 h. The reaction was added with 3 M HCl to adjust pH=1-2 and stirred at room temperature for 1 h, then a saturated aqueous solution of NaHCO₃ was added to adjust pH=7-8 and extracted with ethyl acetate. The organic layer was washed with brine, dried over anhydrous Na₂SO₄ and concentrated under reduced pressure. The residue was purified by silica gel chromatography to give FC-33 (38 mg, 10%) as a yellow solid.

Preparation of Compound FC-34:

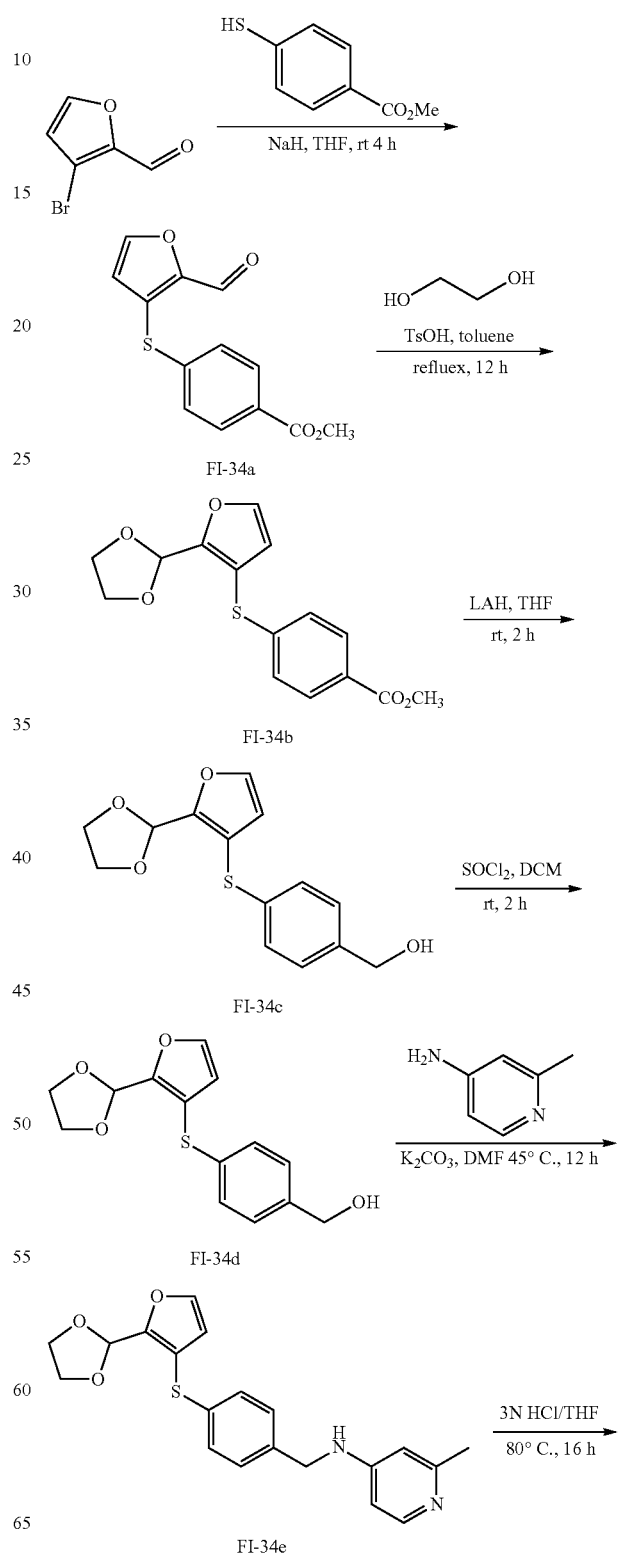

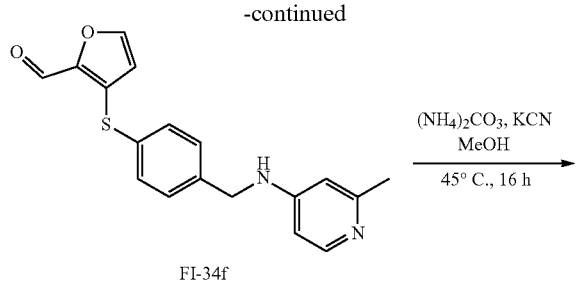

FI-34f

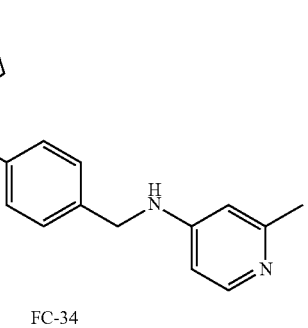

FC-34

To a mixture of 3-bromofuran-2-carbaldehyde (5.0 g, 28.57 mmol, 1.0 eq) and methyl 4-mercaptobenzoate (4.8 g, 28.57 mmol, 1.0 eq) in THF (100 mL) was added NaH (1.14 g, 28.57 mmol, 1.0 eq, 60% w/w) at 0° C. The mixture was allowed to warm to room temperature and stirred for 4 h under nitrogen atmosphere. Then the mixture was quenched with ice water (100 mL) and added with 2 N HCl to adjust pH=7, and extracted with EA (3×50 mL). The combined organic phases were washed with brine, dried over anhydrous $Na_2SO_4$ and concentrated under reduced pressure. The residue was purified by silica gel chromatography to afford FI-34a (2.7 g, 36%).

To a solution of FI-34a (4.8 g, 18.3 mmol, 1.0 eq) in toluene (100 mL) was successively added ethane-1,2-diol (22.7 g, 36.6 mmol, 20 eq) and TsOH (0.16 g, 0.9 mmol, 0.05 eq). The mixture was heated under reflux for 12 h under nitrogen atmosphere. Then the mixture was concentrated under reduced pressure. The residue was purified by column chromatography on a silica gel to give FI-34b (2.4 g, 36%).

To a solution of FI-34b (2.4 g, 7.83 mmol, 1.0 eq) in THF (80 mL) was added $LiAlH_4$ (0.89 g, 23.5 mmol, 3 eq) at 0° C. under nitrogen atmosphere. The mixture was stirred at room temperature for 2 h. Then the mixture was cooled to 0° C. and quenched with 1N HCl (30 mL). The mixture was extracted with DCM (3×50 mL). The combined organic phases were washed with saturated aqueous of $NaHCO_3$, brine, dried over anhydrous $Na_2SO_4$ and concentrated under reduced pressure. The residue was purified by silica gel chromatography to afford FI-34c (2.0 g, 22%).

To a solution of FI-34c (1.0 g, 3.59 mmol, 1.0 eq) in DCM (20 mL) was added $SOCl_2$ (0.85 g, 7.18 mmol, 2 eq) at 0° C. under nitrogen atmosphere. The mixture was stirred at room temperature for 2 h. Then the mixture was concentrated under reduced pressure to afford FI-34d (1.01 g, 99%), which was directly used in next step.

To a solution of FI-34d (0.7 g, 2.36 mmol, 1.0 eq) in DMF (20 mL) was added 4-Amino-2-methylpyridine (0.26 g, 2.36 mmol, 1.0 eq) and $K_2CO_3$ (0.65 g, 4.7 mmol, 2 eq). The mixture was stirred at 45° C. for 12 h. Then the mixture was diluted with water (50 mL) and extracted with ethyl acetate (30 mL*3). The organic layer was washed with brine, dried over anhydrous $Na_2SO_4$ and concentrated under reduced pressure. The residue was purified by silica gel chromatography to afford FI-34e (0.5 g, 57%).

A mixture of FI-34e (0.8 g, 2.17 mmol, 1.0 eq) in HCl/THF (3.0 M, 3 mL/3 mL) was stirred at 80° C. for 16 h. The reaction mixture was concentrated under reduced pressure. The residue was added with saturated $NaHCO_3$ solution to adjust pH=8 and extracted with ethyl acetate. The organic layer was washed with brine, dried over anhydrous $Na_2SO_4$ and concentrated under reduced pressure. The residue was purified by silica gel chromatography to afford FI-34f (0.5 g, 70%).

To a solution of FI-34f (0.5 g, 1.54 mmol, 1.0 eq) in MeOH (5 mL) was added $(NH_4)_2CO_3$ (0.59 g, 6.16 mmol, 4.0 eq) and KCN (0.2 g, 3.08 mmol, 2.0 eq). The mixture was stirred at 45° C. for 16 h. The reaction was added with 3 M HCl to adjust pH=1-2 and stirred at room temperature for 1 h, then a saturated aqueous solution of $NaHCO_3$ was added to adjust pH=7-8 and extracted with ethyl acetate. The organic layer was washed with brine, dried over anhydrous $Na_2SO_4$ and concentrated under reduced pressure. The residue was purified by silica gel chromatography to give FC-34 (41 mg, 6%) as a yellow solid.

Biological Testing

Example 1: MMP Inhibitory Assays

The inhibitory effect of compounds on the rate of cleaving fluorogenic MMP substrate (Enzo, BML-P128) by recombinant human MMP-12 catalytic domain (Enzo, BM1L-SE138) was carried out by methods known in the art. Briefly, to each well of a 96-well black opaque plate, all the reagents were sequentially added by pipetting, and the final reaction contained 4 nM of recombinant human MMP-12 catalytic domain, 4 μM of fluorogenic MMP substrate, and various concentrations (0.15 nM to 10,000 nM) of tested compound dilutions in HEPES buffer (pH 7.5) containing 10 mM of $CaCl_2$, 0.01% Brij® 35 (polyoxyethylene (23) lauryl ether), and 0.1 mg/ml of BSA.

The enzyme and compounds were pre-incubated on a shaker to mix in wells. After an hour of mixing, fluorogenic substrate was added to each well. Reaction without enzyme was used as a blank control in the plate. The plate was then fed into a plate reader to measure fluorescence intensity at Excitation/Emission wavelengths of 340 nm/440 nm every 10 mins for at least 1 hour at 37° C. The $IC_{50}$ of each compound in MMP-12 inhibition was determined by using a readout obtained at time point 30 minutes. The results for each compound tested are show in Table 1.

Example 2: Selectivity Assay

The MMP selectivity assay was performed by using other recombinant human MMPs, including MMP-1, MMP-2, MMP-3, MMP-7, MMP-8, MMP-9, MMP-10, MMP-13, and MMP-14. The $IC_{50}$ of the compounds for the other recombinant human MMPs was determined as described above in Example 1, and are shown in Table 2.

TABLE 2

Selectivity Profile from MMP-12 of Compounds According to Embodiments of the Application Compound Activity

| ID | MMP-12 | MMP-1 | MMP-2 | MMP-3 | MMP-7 | MMP-8 | MMP-9 | MMP-10 | MMP-13 | MMP-14 |
|---|---|---|---|---|---|---|---|---|---|---|
| FC-4  | A | E | C | C | E | B | C | C | B | D |
| FC-10 | A | E | D | C | E | D | D | D | D | D |
| FC-11 | A | E | D | C | E | D | D | D | D | D |
| FC-17 | A | E | C | C | E | C | D | C | C | D |
| FC-23 | A | E | C | D | E | D | D | D | D | D |
| FC-27 | A | E | C | C | E | C | D | C | C | D |

A = less 10 nM,
B = 10 nM to 100nM,
C = 100 nM to 1000 nM,
D = 1000 nM to 10000 nM,
E = greater than 10000 nM The results in Table 2 above show that compounds according to embodiments of the application have high selectivity for MMP-12 as compared to other MMPs, including MMP-1 MMP-2, MMP-3, MMP-7, MMP-8, MMP-9, MMP-10, MMP-13, and MMP-14.

Example 3: Therapeutic Efficacy Study of MMP-12 Inhibitor in Bleomycin-Induced SD Rat Unilateral Lung Fibrosis Model for Idiopathic Pulmonary Fibrosis (IPF)

The purpose of this study was to evaluate the therapeutic effect of FC-4 on bleomycin (BLM) induced unilateral lung fibrosis model in Sprague Dawley (SD) rats. Male SD rats (n=50) were randomly divided into the following groups: Sham group (n=10), Model group (n=10), FC-4 administered at 10 mg/kg/day group (n=10), FC-4 administered at 30 mg/kg/day group (n=10), and FC-4 administered at 100 mg/kg/day group (n=10). All test drugs were delivered orally starting from day 8 of modeling for 14 days. Saline solution was taken for sham and model groups once a day, and FC-4 twice a day for drug treatment groups. Rats were anesthetized and the trachea was exposed. Saline was administrated via direct intra-trachea injection in the sham group, and the other groups' animals received a BLM injection at a dose of 3 mg/kg in volume of 1.0 ml/kg. All animals were processed using a non invasive lung function test with EMMS Whole Body Plethysmography system at pre-modeling, and at days 3, 7, 11, 14, 18 and 21 of modeling. One day after the last drug delivery, the left lung of all animals was perfused with 10% formalin, and processed for pathology analysis.

All animals' lung function changed minimally after modeling showing at tidal volume (TV), breath rate, inspiratory volume per minute (MV) and Penh. index. FC-4 treatment did not significantly affect the lung function, and there was no significant difference as compared to vehicle animals at each test time point. Histology examination revealed that fibrotic lungs in the model group showed epithelial cell hyperplasia in the bronchial and alveolar ducts, a different quantity of mucus mass in the bronchial lumen, and inflammatory cell infiltration, especially in the adventitial area. Alveoli in the fibrosis core were damaged as alveolar epithelial cell shedding and regeneration, alveolar wall inflammatory cell infiltration and fibrosis, and alveolar cavity inflammatory cell infiltration with fibrosis mass were observed. Animals treated with FC-4 at dosage of 10 mg/kg/day showed a significant therapeutic effect on lung fibrosis as compared to the model group. Increasing the dose of FC-4 to 30 mg/kg/day and 100 mg/kg/day also showed a significant therapeutic effect, however a clear dose dependent effect was not observed. Fibrosis Ashcraft scoring data showed FC-4 had a similar significant reduction in fibrosis score. Biomarker analysis using immunohistochemistry (IHC) indicated FC-4 treatment had a similar reduction in Collagen-I and collagen-IV deposition in fibrosis core; MMP-12, TGF-β1 and elastin expression in the fibrosis core also had a clear reduction in expression.

In conclusion, successful BLM induced unilateral lung fibrosis model was achieved. Oral administration of FC-4 starting on day-8 of the lung fibrosis model for 2 weeks provided a significant therapeutic effect either at a dose of 10 mg/kg/day, 30 mg/kg/day or 100 mg/kg/day. Treatment with FC-4 also showed a significant therapeutic effect on lung fibrosis as compared to model group with all dosing group. Fibrosis related biomarker analysis indicated that FC-4 treatment reduced the related biomarker expression and collagen deposition in the fibrosis core, suggesting the therapeutic mechanism of FC-4 for IPF.

Detailed Experimental Methods

Animals: Species and quality level: SD rats, SPF grade. Gender and number: male, 93. Purchasing body weight range: 260-280 g. Company Certificate No.: SCXX (Jing) 2012-001, Beijing Vital River Laboratory Animal Technology Co., Ltd. Animal Housing: Rats were housed in the Animal House Facility of the Nanjing BioSciKin Co. Ltd. under international standards for temperature, humidity and light control system. The animal use protocol was reviewed and approved by the Institutional Animal Care and Use Committee (IACUC) of KCI Biotech Inc. All experimental procedures were conducted in conformity with institutional guidelines of KCI Biotech Inc.

Model Establishment: This study was carried out in strict accordance with the SOP institutional guidelines for the care and use of laboratory animals. Rats were anesthetized by intraperitoneal injection of pentobarbital sodium at dose of 50 mg/kg. Then rat neck skin was disinfected and opened in layers. The trachea was exposed carefully. Bleomycin (BLM) was directly injected into the left main bronchus at a dose of 3 mg/kg body weight in volume of 1.0 ml/kg via a cannula. After closing the trachea and skin in layers the animal was moved on an electric heat pad at 37° C. to await waking up from the anesthesia before returning to holding cages with free access to water and diet.

Experiment Grouping: Rats were assigned into 5 groups: Sham (Group-1, n=10), Model (Group-2, n=10), FC-4-Low dose (Group-3, 10 mg/kg/day, n=10), FC-4-Middle dose (Group-4, 30 mg/kg/day, n=10), FC-4-High dose (Group-5, 100 mg/kg/day, n=10) (Table 1). Drug administration: Test article FC-4 were designed as an oral administration via a gastric perfusion. FC-4 was delivered twice a day starting from day-8 of modeling for 14 days. (Table 3.1).

Figure 1B:
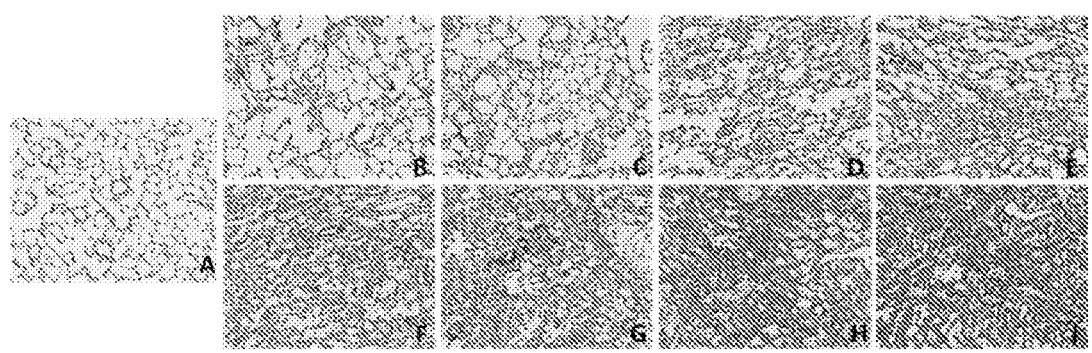

Endpoint: a) Non invasive lung function test: All animals were given a non-invasive lung function examination with EMMS Whole Body Plethysmography (WBP) system at multiple time points during the study periods, including at pre-IPF modeling, day-3 of IPF, day-7 of IPF before dosing, day-11 of IPF, day-14 of IPF, day-18 of IPF and day-21 of IPF before sacrificing the animals, focusing on the parameters of tidal volume (TV), breath rate, inspiratory volume per minute (MV) and Penh. index. b) Left lung collection for pathology analysis: After the last examination of lung function, all animals were euthanized according to the standard SOP at KCI. After confirming the animal death, each animal received a systemic perfusion with 10% formaldehyde solution, then the left lung was harvested and perfused again with an equal volume of 10% formaldehyde solution (3 ml for each lung). Lung pathology was processed after lung fixation. c) Left lung pathology assay: The whole left lung was dehydrated and wax embedded following KCI pathology SOP, then sectioned at 3 μm in thickness. Hematoxylin and eosin (H&E), and Masson Trichrome staining were processed following KCI pathology standard staining SOPs, and whole slides were then scanned by Hamamatsu NanoZoomer Digital Pathology S210 slide scanner after staining. Bronchiole and pulmonary arteriole damage and inflammatory cell infiltration in fibrosis core and fibrosis board area were scored with H&E stained slides according to the criteria set forth in Table 3.2 and Table 3.3 (see also FIG. 1A). BLM induced left lung injury area and pathological fibrosis score were evaluated with Masson Trichrome stained slides according to the criteria set forth in Table 3.4 and FIG. 1B. Also, five animals from each group (three animals from the sham group) were randomly selected for biomarker analysis using IHC methods, such as Collagen-I (Abcam, Cat #ab34710), Collagen-IV (Abcam, Cat #ab6586), MMP-12 (LSBio, Cat #LS-C497709), TGF-β1 (Invitrigen, Cat #MA5-16949) and elastin (Abcam, Cat #GR134273-29). The IHC staining was processed according to the standard protocol of IHC at KCI. The stained slides were then scanned by Hamamatsu NanoZoomer Digital Pathology S210 slide scanner and analyzed using the software to get the positive staining area/analysis area (%). d) Statistical analysis: Statistical analysis was performed using Graphpad prism 5.0 software. Descriptive results were expressed as mean sem or mean±sd. Statistical comparisons were performed using t-test, one-way analysis of variance or two-way analysis of variance test. $p<0.05$ was considered as statistically significant.

TABLE 3.1

Animal Experimental groups

| Group | N | BLM (3.0 mg/kg) | CPD[1] dosing | CPD | Route | Dosage (mL/kg) | Dosing rate |
|---|---|---|---|---|---|---|---|
| G1 | 10 | No | No | Saline | p.o. | 10 | QD |
| G2 | 10 | Yes | Yes | Vehicle | p.o. | 10 | QD |
| G3 | 10 | Yes | Yes | FC-4 10 mg/kg/d | p.o. | 10 | BID |
| G4 | 10 | Yes | Yes | FC-4 30 mg/kg/d | p.o. | 10 | BID |
| G5 | 10 | Yes | Yes | FC-4 100 mg/kg/d | p.o. | 10 | BID |

[1]CPD Dosing = Compound dosing

TABLE 3.2

| | Criteria for grading bronchiole damage and inflammatory cell infiltration |
|---|---|
| Score | The damage of terminal bronchiole wall |
| 0 | Normal structure |
| 1 | Normal structure with less than ½ of the terminal bronchiole wall area injury and characterized by bronchial epithelial cells damage and epithelium regeneration, wall edema, medium layer of the mucosal muscle degeneration or regeneration. |
| 2 | Normal structure with more than ½ of the terminal bronchiole wall area injury and characterized by bronchial epithelial cells damage and epithelium regeneration, wall edema, medium layer of the mucosal muscle degeneration or regeneration. |
| 3 | Normal structure with more than ½ area of the terminal bronchiole wall injury and characterized by bronchial epithelial cells damage and epithelium regeneration, wall edema, medium layer of the mucosal muscle degeneration or regeneration, granulomas formation or fibrosis. |
| Score | The terminal bronchiole wall inflammatory cells infiltration |
| 0 | Normal structure with no inflammatory cells infiltration |
| 1 | The terminal bronchiole outside wall with a few scattered inflammatory cell infiltration (less than 10) but no focal. |
| 2 | The terminal bronchiole outside wall with a lot scattered inflammatory cell infiltration which is focal or diffuse and totaled less than ½ area of the terminal bronchiole wall. |
| 3 | The terminal bronchiole outside wall with diffuse infiltration of inflammatory cells and totaled more than ½ area of the terminal bronchiole wall, inflammatory cells infiltration in the inner and medium layer of the membrane. |

TABLE 3.3

Criteria for grading pulmonary arteriole damage and inflammatory cell infiltration

| Score | Pulmonary small arteries wall damage |
|---|---|
| 0 | The structure of pulmonary small arteries is clear and complete |
| 1 | The parts endothelial cells exfoliate |
| 2 | The endothelial cells exfoliate, medium layer of the smooth muscle degeneration, regeneration or small focal necrosis. |
| 3 | The endothelial cells exfoliate, medium layer of the smooth muscle degeneration, regeneration or small focal necrosis, medium layer of the smooth muscle degeneration, regeneration or small focal necrosis, medium layer granulomas formation or fibrosis. |

| Score | Pulmonary arteriole inflammatory cell infiltration |
|---|---|
| 0 | Normal structure of pulmonary small arteries |
| 1 | The pulmonary small arteries outside wall with a few scattered inflammatory cell infiltration (less than 10) but no focal. |
| 2 | The pulmonary small arteries outside wall with a lot scattered inflammatory cell infiltration which is focal or diffuse and totaled less than ½ area of the artery wall. |
| 3 | The pulmonary small arteries outside wall with diffuse infiltration of inflammatory cells and totaled more than ½ area of the pulmonary small artery wall, inflammatory cells infiltration in the medium layer of the membrane. |

TABLE 3.4

Criteria of histological features for lung fibrosis scoring

| Grade of fibrosis | Ashcroft scoring criteria |
|---|---|
| 0 | Alveolar septum: no fibrosis lesion<br>Structure: normal |
| 1 | Alveolar septum: Isolated and Simple Pulmonary fibrosis ( alveolar walls thicken but less than three times thicker than that in normal lung)<br>Structure: Large alveolar areas, little exudate, no fibrosis material. |
| 2 | Alveolar septum: Clear fibrosis change (alveolar walls thicken and more than three times thicker than that in normal lung), small nodule formation but no connection.<br>Structure: Large alveolar areas, little exudate, no fibrosis material. |
| 3 | Alveolar septum: Early stage fibrosis forms in all alveolar (alveolar walls thicken and more than three times thicker than that in normal lung). Structure: Large alveolar areas, little exudate, no fibrosis material. |
| 4 | Alveolar septum: Alveolar septum is still visible.<br>Structure: Isolated fibrosis nodule formation in alveolar ($\leq$10% at high magnification) |
| 5 | Alveolar septum: Alveolar septum is still visible.<br>Structure: Integrate fibrosis nodule formation in alveolar (>10% and $\leq$50% at high magnification). Lung structure is substantially impaired but exists. |
| 6 | Alveolar septum: seen but barely exists.<br>Structure: Integrate fibrosis nodule formation in alveolar (>50% at high magnification). Lung structure barely exists. |
| 7 | Alveolar septum: does not exist.<br>Structure: Pulmonary alveoli and interstitial fibrosis proliferation were seen but there are still 5 vacuole structures. |
| 8 | Alveolar septum: does not exist.<br>Structure: Pulmonary alveoli and interstitial fibrosis proliferation were seen at high magnification. |

Figure 1C:
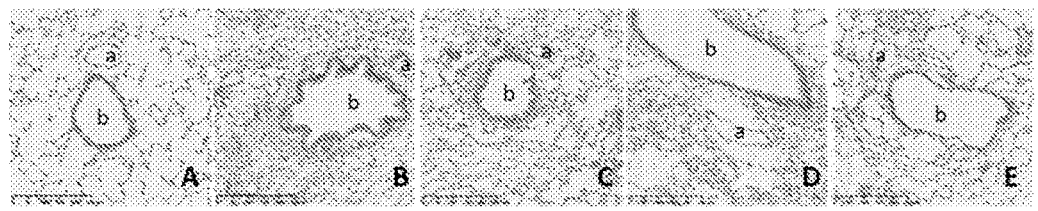
Figure 1D:
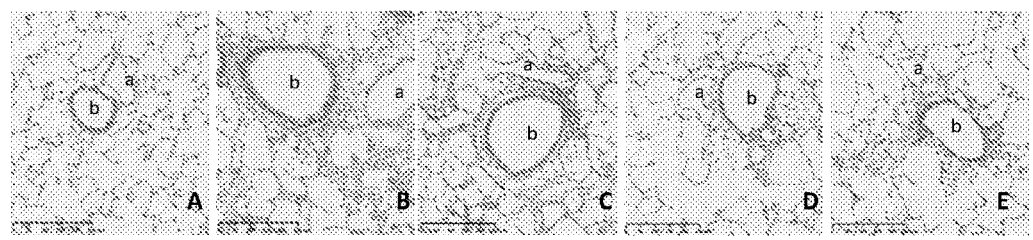
Figure 1E:
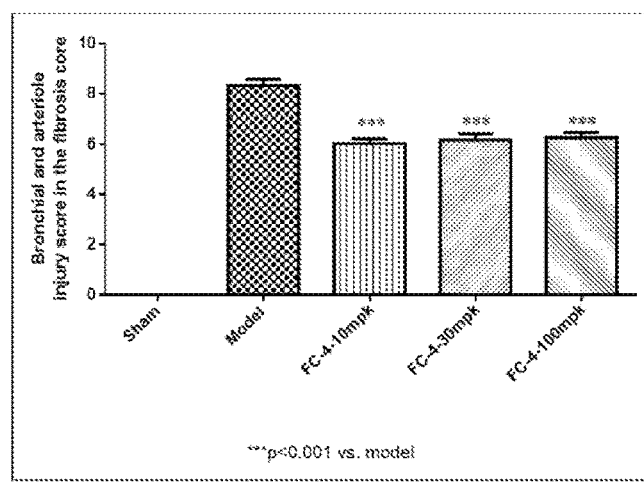
Figure 1F:
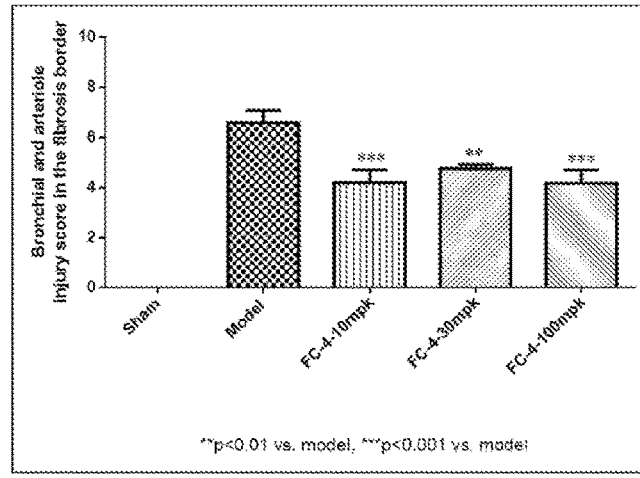

Results:
a) There was no obviously physical and behavior abnormality change in all tested rats during the experiment.
b) All rat body weights were reduced slightly over the first six to seven days after surgery, except group-1 rats during the experimental period. Then, all rat body weights began to recover gradually with the experimental process. There was no significant difference in body recovery among the CPD treatment groups and model group.
c) Changes in non invasive lung function: The test parameters for lung function indicated the minimal changes in TV, MV, breath rate and Penh over the first week of unilateral lung fibrosis modeling. With the treatment of FC-4 these test parameters in treated animals did not show any significant changes as compared to vehicle treated animals.
d) Pathological analysis of bronchi and arterioles in left lung: Left lung histology represented a significant lung injury with a clear damage board, which showed as a different degree of bronchial hyperplasia, terminal fine bronchus and alveolar duct epithelial cell hyperplasia, and a different quantity of mucus in bronchial lumen. A different degree of inflammatory cell infiltration on bronchial walls, especially in the adventitia area; and partial bronchial wall thickness with granulation tissue were observed. Alveolar damages in the fibrosis core were represented as alveolar epithelial denudation, regeneration, alveolar wall inflammatory cell infiltration and fibrosis. Inflammatory exudation in the alveolar cavities with fibrotic mass was also recognized widely. A Different degree of arteriole endothelial cell denudation and proliferation were seen both in fibrosis core and fibrosis board with a different degree of inflammatory cell infiltration, mostly located in the adventitia area (FIGS. 1C and 1D). All doses of FC-4 treatment had a significant therapeutic effect on the reduction of bronchial and arteriole damages both in the fibrotic core and in the border of fibrosis (Table 3.7, FIGS. 1E and 1F).

Figure 1G:
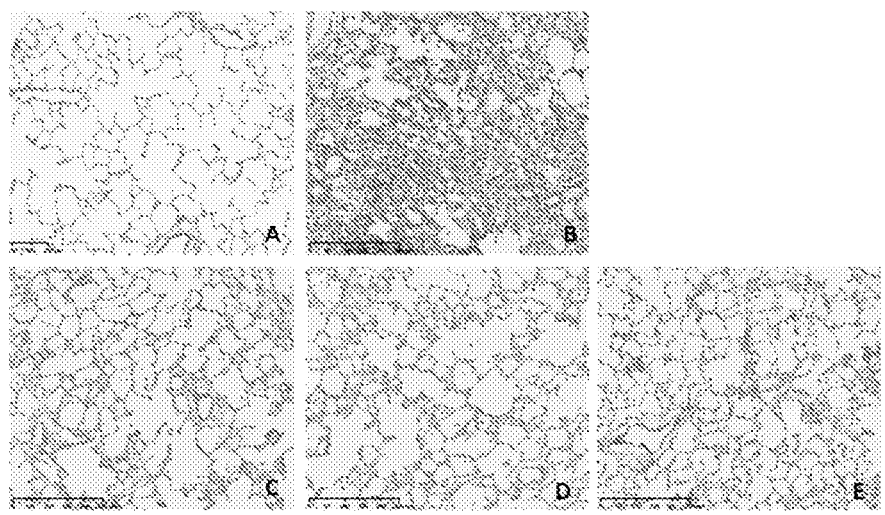
Figure 1H:
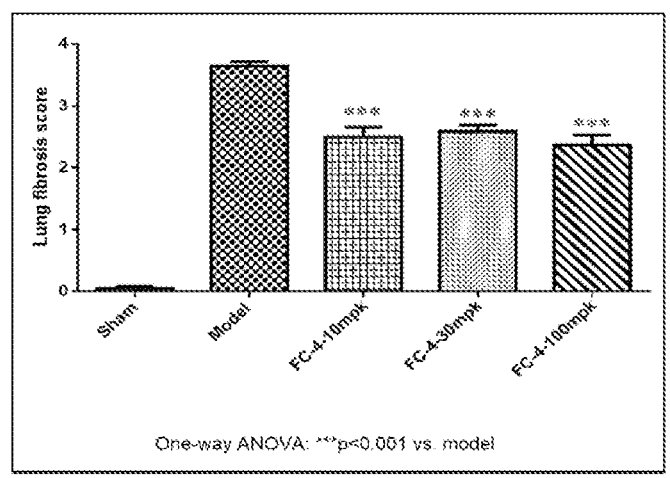
Figure 1I:
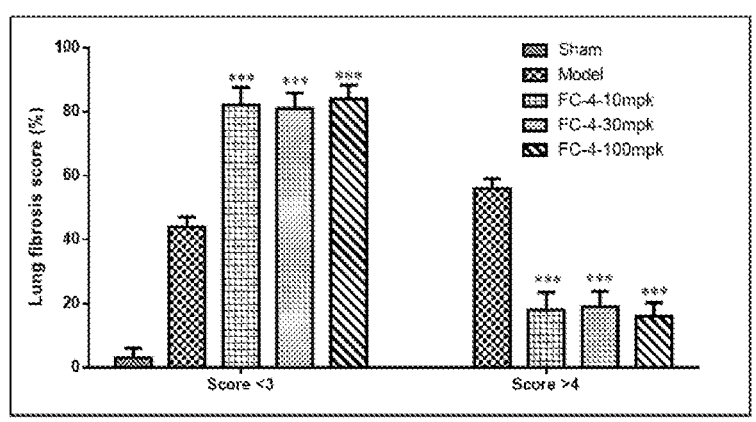
Figure 1J:
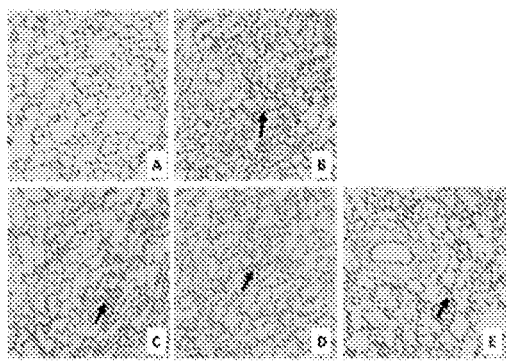
Figure 1J:
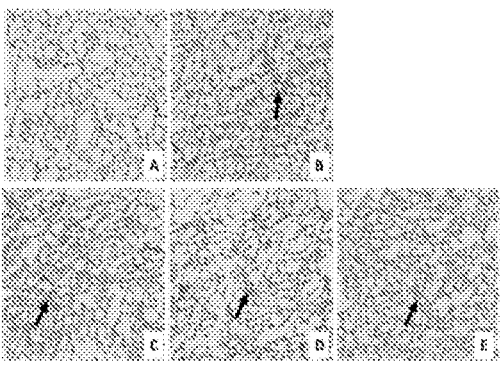
Figure 1J:
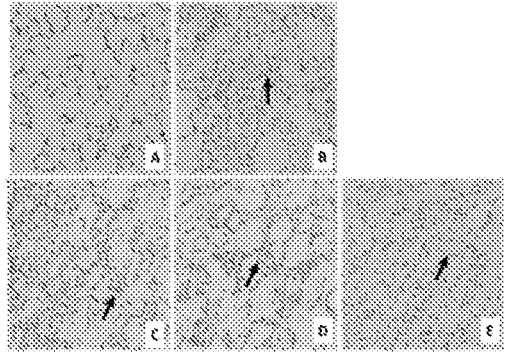
Figure 1J:
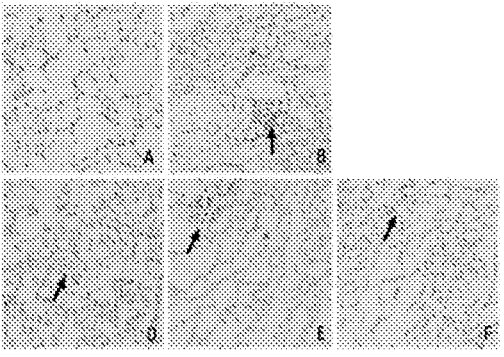
Figure 1J:
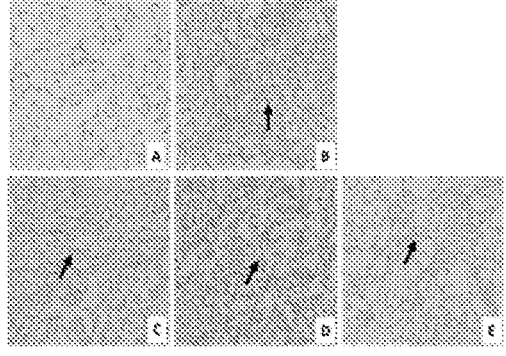
Figure 1K:
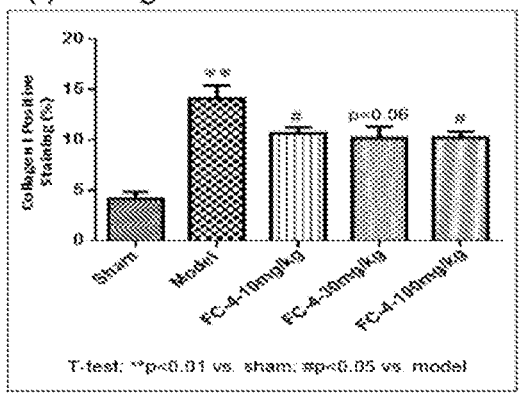
Figure 1K:
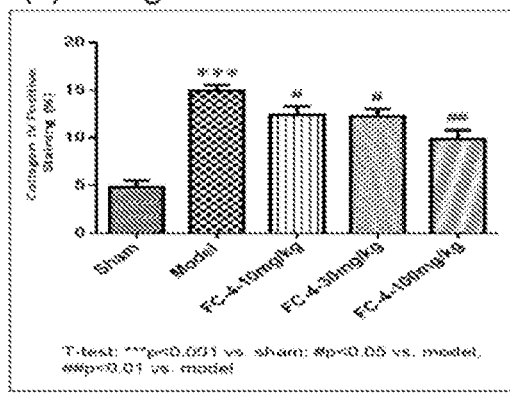
Figure 1K:
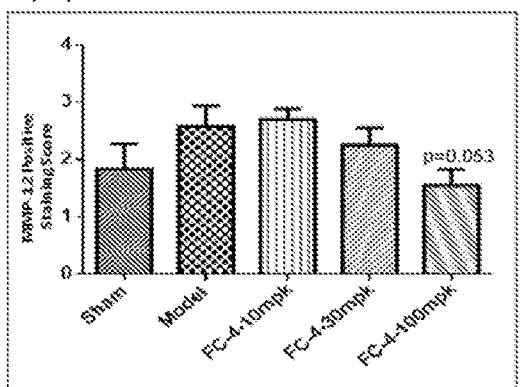
Figure 1K:
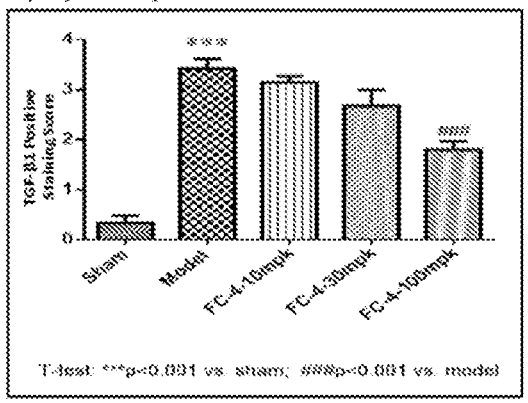
Figure 1K:
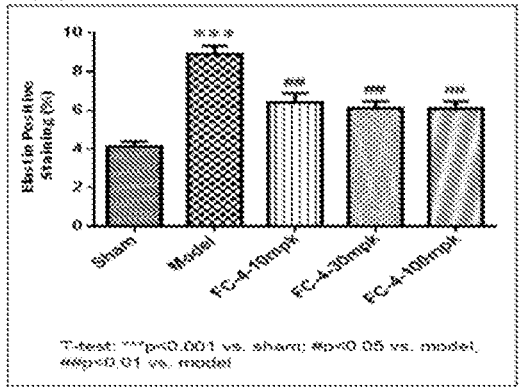

FIG. 1K (I)); Collagen-IV: Collagen-IV IHC analysis indicated a significant dose dependent reduction in the collagen-IV deposition in the fibrosis core both in FC-4 treated animals (p<0.05) (FIG. 1J (II) and FIG. 1K (II)). 3) MMP-12: MMP-12 IHC analysis showed a significant reduction in MMP-12 expression in the fibrosis core in FC-4 treated animals with a clear dose dependent reduction (p>0.05) (FIG. 1J (III) and FIG. 1K (III)). 4) TGF-β1: TGF-β1 IHC analysis showed a significant reduction in the TGF-β1 expression in the fibrosis core in FC-4 treated animals (p<0.05) (FIG. 1J (IV) and FIG. 1K (IV)). 5) Elastin: Elastin IHC analysis showed a significant reduction in the elastin expression in the fibrosis core in FC-4 treated animals (p<0.05) (FIG. 1J (V) and FIG. 1K (panel (V)).

TABLE 3.7

Left lung bronchial and arteriole damages

| Group Score | Sham (n = 10) | Model (n = 10) | FC-4 10 mg/kg/d (n = 10) | RC4 30 mg/kg/d (n = 10) | FC4 100 mg/kg/d (n = 10) |
|---|---|---|---|---|---|
| Fibrosis core | 0.0 ± 0.0 | 8.34 ± 0.24 | 6.04 ± 0.19*** | 6.18 ± 0.26*** | 6.28 ± 0.21*** |
| Fibrosis border | 0.0 ± 0.0 | 6.56 ± 0.51 | 4.2 ± 0.516*** | 4.76 ± 0.16** | 4.18 ± 0.53*** |

***$p < 0.001$ vs. model;
**$p < 0.01$ vs. model e) Pathological analysis of left lung fibrosis core: With Masson Trichrome staining the left lung fibrosis was scored according to Ashcraft scoring methods. A significant alveolar damage with fibrosis was recognized (FIG. 1G). Ashcraft scoring data indicated a significant reduction in fibrosis after FC-4 treatment (Table 3.8, FIG. 1H). Based on the Ashcraft scoring criteria, the fibrosis scores were divided into two sections as section-I as score <3, which means the original alveolar structure is preserved with a different damage and fibrosis, and section-II as score 4, which means the alveolar structure is damaged partially or totally with a different damage and fibrosis. The data showed over sixty percent (60%) of the Ashcraft score was score 4 in the model group. About eighty percent (80%) of the Ashcraft score was score 3 for all drug treatment groups. The statistical analysis showed that there was a significant difference between FC-4 treated group and model group (FIG. 1J).

Example 4: Efficacy Study of MMP-12 Inhibitors on SD Rat Kidney Fibrosis Model by Unilateral Ureteral Occlusion (UUO)

This study was to evaluate the therapeutic efficacy of the MMP-12 inhibitor FC-4 on a renal fibrosis model by unilateral ureteral occlusion (UUO). Male Sprague Dawley (SD) rats (180-220 g, n=71) were used in this study. Animals were randomly divided into 4 groups: vehicle group (group-1, n=8), FC-4 2 mg/kg/day group (group-2, n=9), FC-4 6 mg/kg/day group (group-3, n=9), FC-4 20 mg/kg/day group (group-4, n=9). Animals were anesthetized with 2.5% isoflurane inhalation. The left ureter was ligated to create a unilateral ureteral occlusion (UUO) model to induce renal fibrosis. The test article FC-4 was administrated twice a day via oral delivery after modeling for 14 days. Peripheral blood serum was prepared at pre-modeling and day-15 (one day after last dosing). All animals were euthanized and processed for left kidney pathology studies.

TABLE 3.8

Evaluation of left lung fibrosis

| Group Score | Sham (n = 10) | Model (n = 10) | PC-4 10 mg/kg/d (n = 10) | PC-4 30 mg/kg/d (n = 10) | PC-4 100 mg/kg/d (n = 10) |
|---|---|---|---|---|---|
| Fibrosis area | 0.0 ± 0.0 | 69.1 ± 3.3 | 75.1 ± 3.0 | 66.4 ± 2.9 | 70.5 ± 3.0 |
| Fibrosis score | 0.1 ± 0.0 | 3.7 ± 0.1 | 2.5 ± 0.2*** | 2.6 ± 0.1*** | 2.4 ± 0.2*** |
| Fibrosis score 1-3 | 3.0 ± 3.0 | 44.0 ± 3.1 | 82.0 ± 5.5*** | 81.0 ± 4.8*** | 84.0 ± 4.3*** |
| Fibrosis score 4-8 | 0.0 ± 0.0 | 56.0 ± 3.1 | 18.0 ± 5.5*** | 19.0 ± 4.8** | 16.0 ± 4.3** |

Two-way ANOVA: ***$p < 0.001$ vs. model f) Pathological analysis of multiple biomarkers in left lung fibrosis core: 1) Collagen-I: The analysis of IHC staining in the fibrosis core for the animals treated with FC-4 showed a significant dosing dependent reduction of Collagen-I deposition and showed a significant difference at each dose treatment (p<0.05) (FIG. 1J (I) and FC-4 treatment at a dose of 20 mg/kg/day did slightly limit the blood urea nitrogen (BUN) elevation as compared to vehicle group, however all data did not show a statistically significant difference as compared to model group. Serum creatinine levels did show a similar change as in the BUN.

Histologically, the left kidneys showed significant morphologic changes relative to the UUO including a pelvic dilatation, renal medula and cortex atropsy, tubular epithelial cell flattening and tubular dilatation, inflammation and necrosis. Interstitial fibrosis was clearly observed in the pelvic wall, medulla and cortex. FC-4 treatment represented a clear dose dependent effect, and a dose at 20 mg/kg/day was more effective than a dose of 2 mg/kg/day (p<0.01). The semi-quantitative evaluation of interstitial inflammation in the cortex indicated a significant reduction with the treatment of FC-4, and showed a dose dependent efficacy of FC-4. The semi quantitative evaluation of interstitial fibrosis in the cortex indicated a significant reduction in the fibrosis score with the treatment of FC-4 at all dose groups. There was a clear dose dependent effect both in FC-4 treatment groups.

The analysis of immunohistochemistry (IHC) staining in the cortex area of the left kidney for the animals treated with FC-4 showed a significant reduction in collagen-I deposition at a dose of 20 mg/kg/day (p<0.001 for FC-4) with a trance of dose dependent reduction with FC-4 treatment. It also showed a significant reduction in collagen-IV deposition at a dose of FC-4 6 mg/kg/day (p<0.05), 20 mg/kg/day (p<0.001) with a trance of dose dependent reduction.

In conclusion, UUO induced a significant kidney cortex damage, inflammation and interstitial fibrosis within 15 days of modeling. The treatment of FC-4 represented a clear dose dependent efficacy either in the limitation in the kidney damage, interstitial inflammation or interstitial fibrosis. Fibrosis related biomarker analysis indicated the treatment with FC-4 reduced the related collagen deposition (Collagen-I and IV) in the cortex area of damaged kidney.

Detailed Experimental Methods

Animals: Gender: Male, SD rats, 180-220 g, total 71. Certificate: 11400700272659, Beijing Vital River Laboratory Animal Technology Co., Ltd., China. Animal holding: Animals were maintained in a temperature-controlled environment with a 12 hours light/12 hours dark cycle and free access to food and water. Experimental procedures were performed according to IACUC guidelines in the KCI (SuZhou) Biotech Inc. (KCI) animal research facility. Model creation: Total 36 male SD rats were used in this study. After anesthesia with 2.5% isoflurane inhalation the animal abdomen was opened surgically. The left ureter was exposed and ligated close to the bladder to create the UUO model. After confirming no bleeding, the abdomen wall was closed in layers. The animals were maintained under temperature controlled pad (37° C.) for the recovery from anesthesia, and then were transferred to holding cages with regular food and water.

Experiment grouping: UUO modeling animals were divided into 4 groups randomly as vehicle (group-1, n=9), FC-4 2 mg/kg/day (group-2, n=9), FC-4 6 mg/kg/day (group-3, n=9), FC-4 20 mg/kg/day (group-4, n=9) (Table 4.1). Dosing regimen: All test articles were designed as an oral administration via a gastric perfusion. Test articles were designed to be delivered twice a day starting on the same day of modeling for 14 days (Table 4.1). Endpoints: 1) Blood collection: Peripheral blood was collected from all animals in each group and prepared for serum at pre-modeling and day-15 (one day after last dosing), stored at −80° C. All animals were euthanized according to KCI SOP. After confirming animal death without breath and heart beat, the left kidneys were perfused with cold PBS followed by 10% neutral formalin and collected for further pathology study. 2) Detection of serum BUN and creatinine: The serum BUN and creatinine level were detected with Hitachi 7060 automatic biochemical analyzer and related test kits. 3) Kidney pathology examination: 3a) Kidney H&E staining and analysis: Following KCI's pathologic SOP all left kidneys were fixed in 10% formalin for at least 24 h at room temperature. After fixation, the kidney was cut longitudinally to get the largest surface and dehydrated in graded ethanol, cleared in xylene, and embedded in paraffin. Thin sections (3-μm) were mounted on glass slides, dewaxed, rehydrated to distilled water, and stained with hematoxylin and eosin (H&E). All stained slides were scanned with NanoZoomer Digital Pathology (S210, Hamamaci, Japan) scanner. Semi quantitative evaluation of the degree of tubular epithelial flattening and dilatation were graded from 0-5 according to the percentage of tubular involvement: score 0=no damage; score 1=1-10% damage; score 2=10-$25\%$ damage; score 3=25-50% damage; score 4=50-75% damage; score 5=75-100% damage. Semi quantitative evaluation of the tubular necrosis is graded from 0 to 3 according to the percentage of tubular involvement: score 0=no necrosis; score 1=<25% necrosis; score 2=25-50% necrosis; score 3=>50% necrosis. The average of tubular flattening and dilatation and necrosis as the total tubular damage was presented. Semi quantitative evaluation of the interstitial inflammation was graded from 0 to 4 according to the degree of inflammatory cell infiltration: score 0=no inflammatory cells; score 1=mild inflammatory cell infiltration; score 2=moderate inflammatory cell infiltration; score 3=severe inflammatory cell infiltration; score 4=extensive inflammatory cell infiltration. 3b) Kidney Masson Trichrome staining and analysis: Thin sections (3-μm) were mounted on glass slides, dewaxed, rehydrated to distilled water, and stained with Masson Trichrome. All stained slides were scanned with NanoZoomer Digital Pathology (S210, Hamamaci, Japan) scanner. Semi quantitative evaluation of cortex interstitial fibrosis with five different fields at ×10 magnification are selected randomly from kidney cortex, estimated using the following scoring system from 0-4 according to the percentage of interstitial fibrosis involvement: score 0=no fibrosis; score 1=<10% fibrosis; score 2=10-25% fibrosis; score 3=25-75% fibrosis; score 4=>75% fibrosis. 3c) Kidney RIC staining and analysis: All of left kidneys from each group (eight right kidneys from model group) were processed for biomarker analysis using IHC methods, such as Collagen-I (Abcam, Cat #ab34710), Collagen-IV (Abcam, Cat #ab6586). The IHC staining was processed according to the standard protocol of IHC at KCI. The stained slides were then scanned by Hamamatsu NanoZoomer Digital Pathology S210 slide scanner and analyzed using the software to get the positive staining area/analysis area (%). 4) Statistical analysis: Graphpad, prism 5.0 was used for all statistical analyses with p value <0.05 considered significant. All data were reported as mean±SEM. Differences between groups were determined using either ANOVA tests with Bonferroni test or student T-test.

TABLE 4.1

Animal Experiment Groups

| Group | N | OP | CPD | Conc. Mg/mL | Dosage mL/kg | Dosage mg/kg |
|---|---|---|---|---|---|---|
| Group-1 | 9 | UUO | Vehicle | N/A | 30 | N/A |
| Group-2 | 9 | UUO | FC-4 | 0.1 mg/ml | 10 | 2 mg/kg/d, bid |
| Group-3 | 9 | UUO | FC-4 | 0.3 mg/ml | 10 | 6 mg/kg/d, bid |
| Group-4 | 9 | UUO | FC-4 | 1 mg/ml | 10 | 20 mg/kg/d, bid |

Figure 2A:
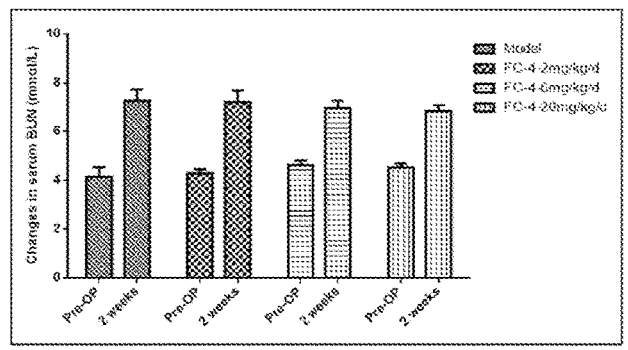
Figure 2B:
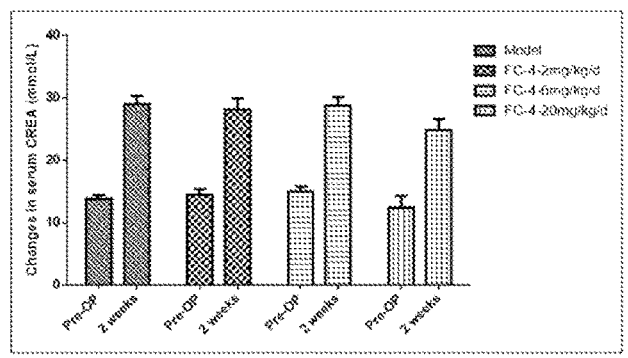
Figure 2C:
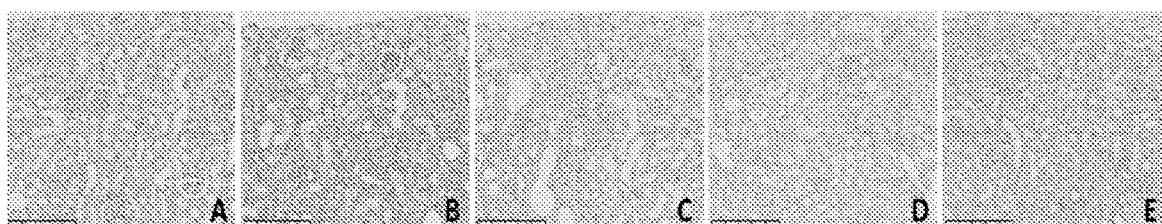
Figure 2D:
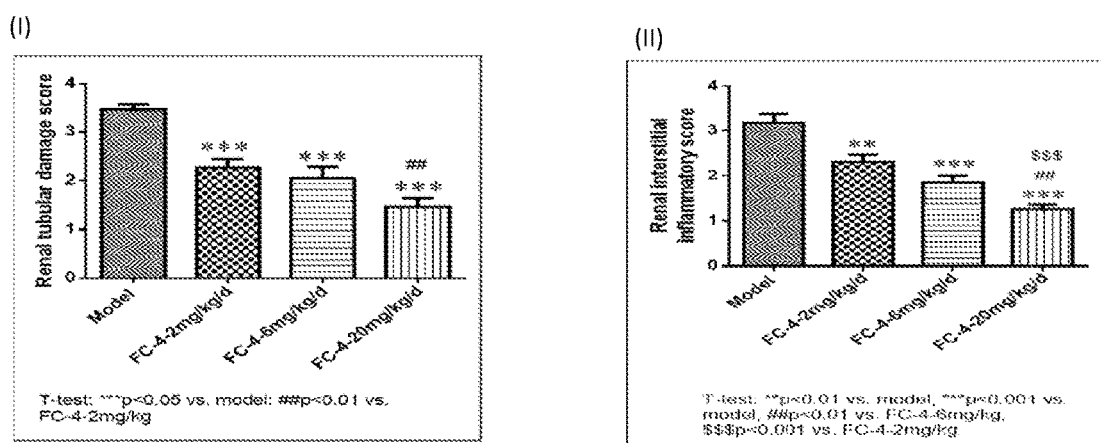

Results:

a) Animal physiological changes during the experimental periods: Several animals died during the experimental period, which was considered as the model failed such as the ureter ruptured during the operation, which induced peritonitis.

b) Changes in the serum BUN and creatitine: Serum BUN in all animals was raised after UUO at day-15 as compared to the pre modeling (p<0.001). FC-4 treatment at a dose of 20 mg/kg/day did slightly limit the BUN elevation as compared to vehicle group, however did not show a statistically significant difference as compared to model group. Serum creatinine levels did show a similar change as in the BUN (FIG. 2B).

c) Changes in the left kidney damage—The tubular damages: After 15 days of UUO, the left kidney showed pelvic cavity dilatation in all animals. The kidney cortex represented a significant atrophy with different degree of tubular epithelial cell flattening, tubular dilatation and interstitial inflammatory cell infiltration, and few foci of tubular necrosis (FIG. 2C). FC-4 treatment represented a clear dose dependent effect, and a dose of 20 mg/kg/d was more effective than a dose of 2 mg/kg/day (p<0.01) (FIG. 2D (I)).

d) Changes in the left kidney damage—The interstitial inflammation: The semi quantitative evaluation of interstitial inflammation in cortex indicated a significant reduction with the treatment of FC-4, and presented a dose dependent efficacy (FIG. 2D (II)). e) Changes in the left kidney damage—The cortex interstitial fibrosis: After 15 days of UUO, the left kidney showed pelvic cavity, medulla area and cortex area with a significant interstitial fibrosis in all animals. The interstitial fibrosis in the cortex area was analyzed and represented a different degree with the test CPDs' treatment (FIG. 2E). The semi quantitative evaluation of interstitial fibrosis in the cortex indicated a significant reduction in the fibrosis score with the treatment of FC-4 at dose of 20 mg/kg/day (p<0.001). There was a clear dose dependent effectin FC-4 treatment groups (FIG. 2F).

f) Pathological analysis of multiple biomarkers in left kidney: Collagen-I: The analysis of IHC staining in the cortex area of left kidney for the animals treated with FC-4 showed a significant reduction in collagen-I deposition at a dose of 20 mg/kg/day (p<0.05) with a trance of dose dependent reduction in treatment groups (FIG. 2G(I) and FIG. 2H(I)). Collagen-IV: IHC staining in the cortex area of the left kidney for the animals treated with FC-4 showed a significant reduction in collagen-IV deposition at dose of 20 mg/kg/day (p<0.001) with a trance of dose dependent reduction. (FIG. 2G(II) and FIG. 2H(II)).

REFERENCES

1. U.S. Pat. No. 7,179,831
2. WO 02/096426
3. US 2004/0067996
4. WO 2004/108086
5. WO 02/074752
6. WO 2004/020415

We claim:

1. A compound of formula (II):

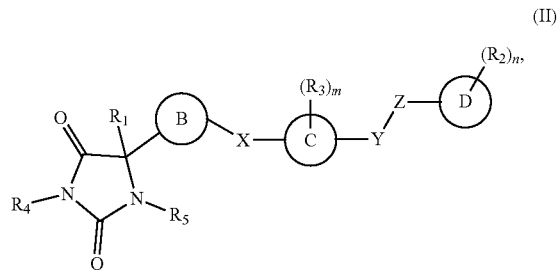

(II)

or a tautomer, stereoisomer, pharmaceutically acceptable salt, or solvate thereof, wherein:

ring B is optionally substituted furanyl;

ring C is aryl or heteroaryl;

ring D is phenyl, pyridinyl, or pyridinyl N-oxide;

each of X, Y, and Z is independently selected from the group consisting of O, $CH_2$, $NR_x$ and $S(O)_q$, wherein $R_x$ is hydrogen or alkyl;

$R_1$ is hydrogen or alkyl;

each $R_2$ is independently selected from the group consisting of hydrogen, alkyl, halo, hydroxyl, haloalkyl, alkoxy, alkylthio, amino, amide, alkylamine, aminoalkyl, cyano, hydroxyalkyl, —$(CH_2)_pC(O)OR_6$, and —$(CH_2)_pOC(O)R_6$;

each $R_3$ is independently selected from the group consisting of hydrogen, alkyl and halo;

$R_4$ is hydrogen or alkyl;

$R_5$ is hydrogen;

each $R_6$ is independently selected from the group consisting of hydrogen and alkyl, wherein the alkyl is unsubstituted or substituted with one or more groups independently selected from the group consisting of amino, hydroxyl, halo, and alkoxy;

m is 1, 2, 3, or 4;

n is 1, 2, 3, 4, or 5;

p is 0, 1, 2, 3, 4, or 5; and q is 0, 1, or 2;

provided that when ring D is phenyl, at least two of the following are true:

(i) $R_1$ is alkyl;

(ii) $R_2$ is not methoxy, chloro, or trifluoromethyl; and (iii) ring C is not unsubstituted phenyl.

2. The compound of claim 1, wherein ring C is phenyl.

3. The compound of claim 1, wherein ring D is pyridinyl or pyridinyl N-oxide.

4. The compound of claim 1, wherein $R_4$ is hydrogen.

5. The compound of claim 1, wherein $R_1$ is alkyl.

6. The compound of claim 1, wherein X is S and Z is $CH_2$.

7. The compound of claim 1, wherein X is S, Y is O, and Z is $CH_2$.

8. The compound of claim 1, wherein n is 1; and $R_2$ is alkyl, alkoxy, hydroxyl, hydroxyalkyl or amide.

9. The compound of claim 1, wherein n is 1; and $R_2$ is —$CH_3$, $C_{1-4}$ alkoxy, —OH, —$CH_2OH$, or —$C(O)NH_2$.

10. The compound of claim 1, being a compound of formula (III):

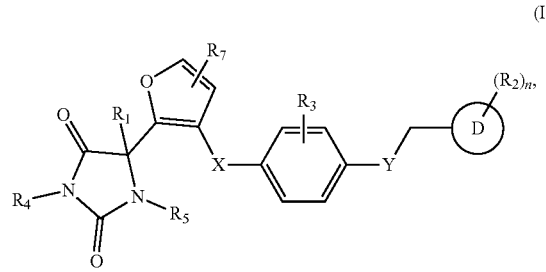
(III)

or a tautomer, stereoisomer, pharmaceutically acceptable salt, or solvate thereof,
wherein:
  $R_1$ is hydrogen or $C_{1-4}$ alkyl;
  X is S;
  Y is O, $CH_2$, NH, or $N(CH_3)$;
  each $R_2$ is independently selected from the group consisting of hydrogen, alkyl, hydroxyl, alkoxy, amide, and hydroxyalkyl;
  each $R_3$ is hydrogen, alkyl or halo;
  ring D is phenyl, pyridinyl, or pyridinyl N-oxide;
  each of $R_4$ and $R_5$ is hydrogen;
  $R_7$ is hydrogen or methyl; and
  n is 1 or 2.

11. The compound of claim 1, being a compound of formula (IV):

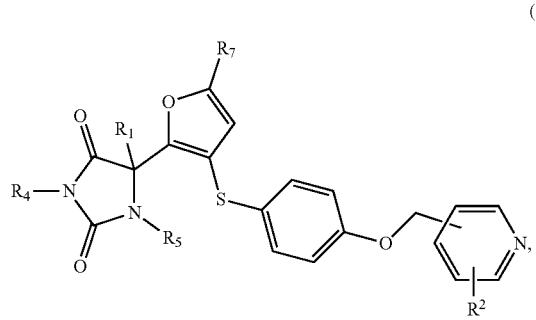
(IV)

or a tautomer, stereoisomer, pharmaceutically acceptable salt, or solvate thereof,
wherein:
  $R_1$ is hydrogen or alkyl;
  $R_2$ is selected from the group consisting of alkyl, amide, hydroxyl, alkoxy, and hydroxylalkyl;
  each of $R_4$ and $R_5$ is hydrogen; and
  $R_7$ is methyl or hydrogen.

12. The compound of claim 11, wherein $R_2$ is —$CH_3$, $C_{1-4}$ alkoxy, —OH, —$CH_2OH$, or —$C(O)NH_2$.

13. The compound of claim 11, wherein $R_1$ is $C_{1-4}$ alkyl.

14. A compound of formula (V):

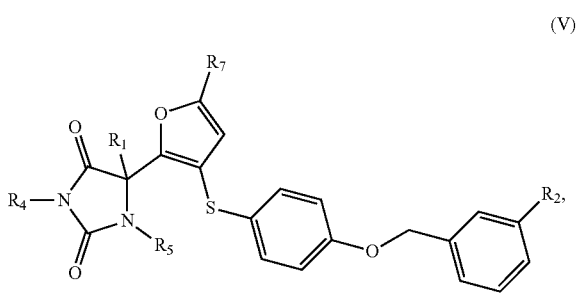
(V)

or a tautomer, stereoisomer, pharmaceutically acceptable salt, or solvate thereof, wherein:
  $R_1$ is alkyl;
  $R_2$ is selected from the group consisting of alkyl, amide, alkoxy, hydroxyl, and hydroxyalkyl;
  each of $R_4$ and $R_5$ is hydrogen; and
  $R_7$ is methyl or hydrogen.

15. The compound of claim 14, wherein $R_2$ is —$CH_3$, $C_{1-4}$ alkoxy, —OH, —$CH_2OH$, or —$C(O)NH_2$.

16. The compound of claim 14, wherein $R_1$ is $C_{1-4}$ alkyl.

17. A compound selected from the group consisting of:

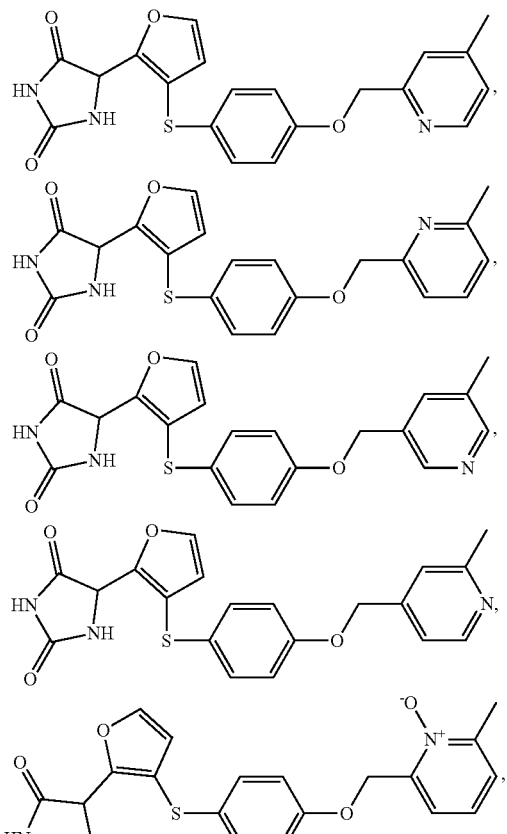

99
-continued
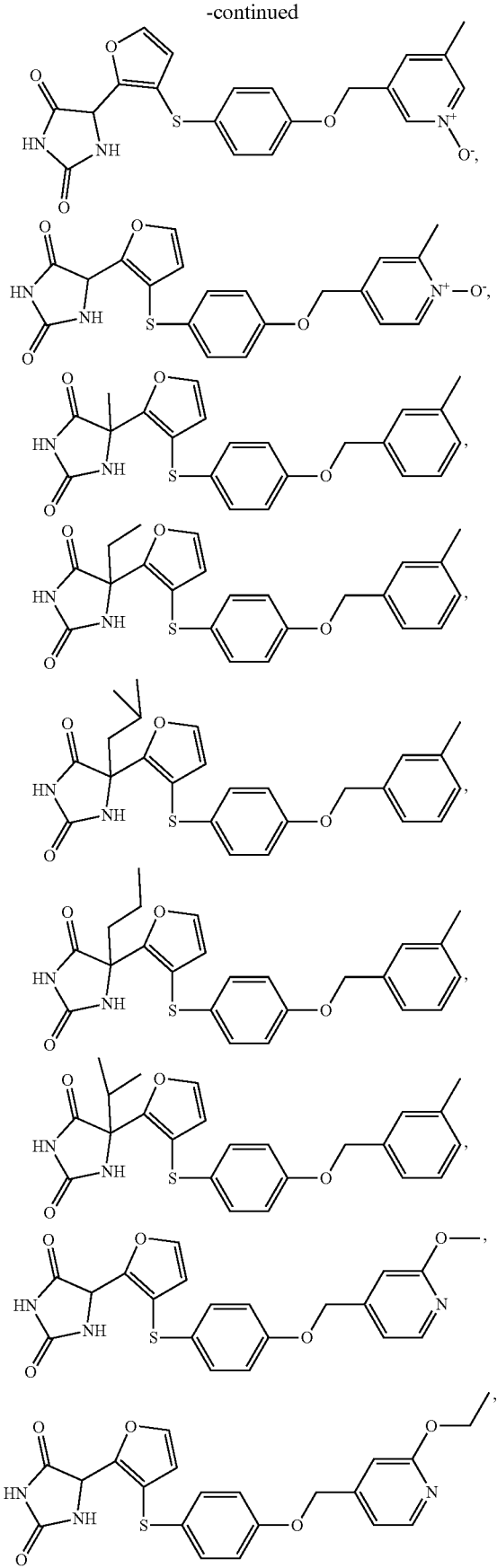
100
-continued
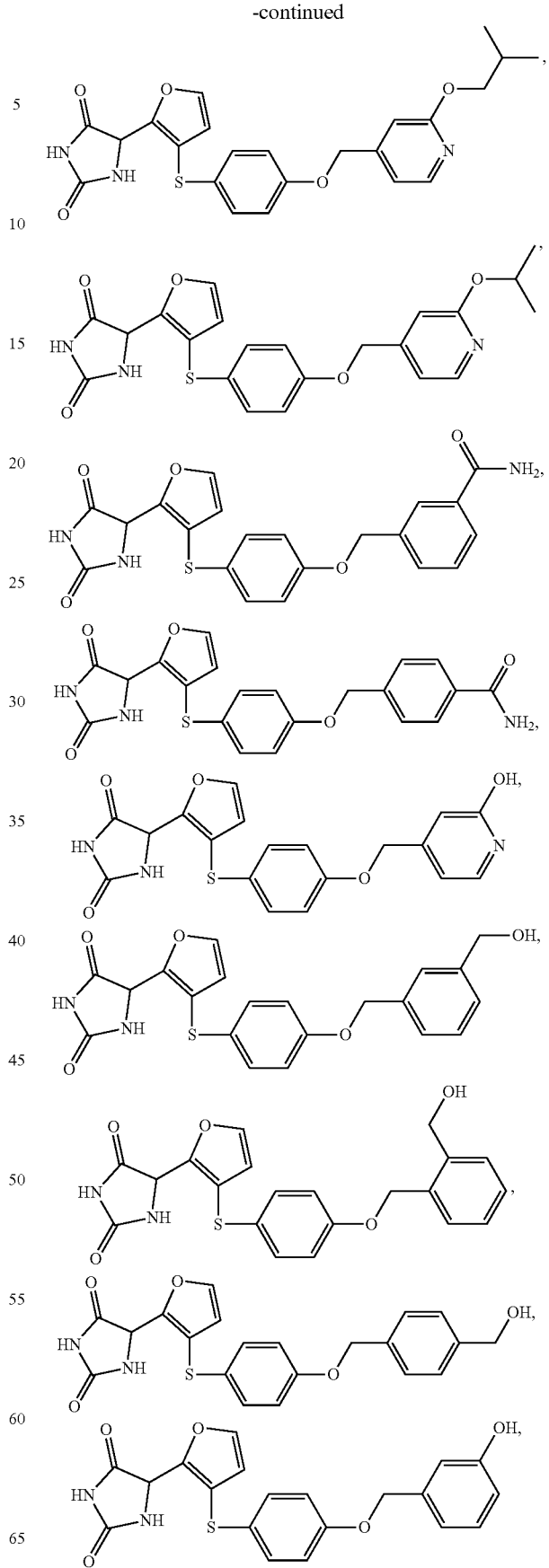

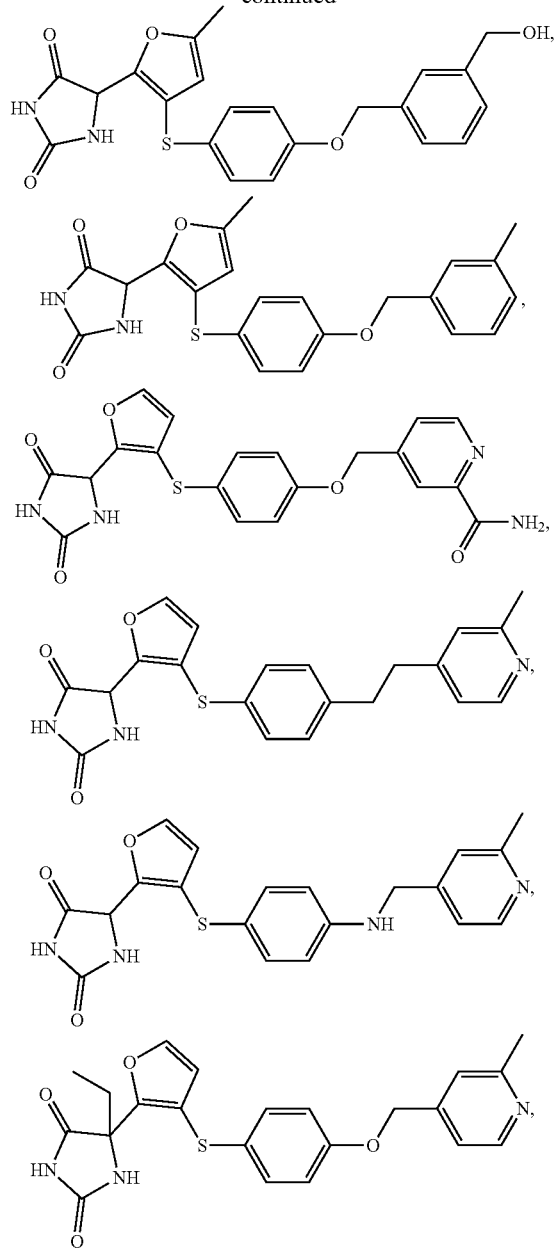

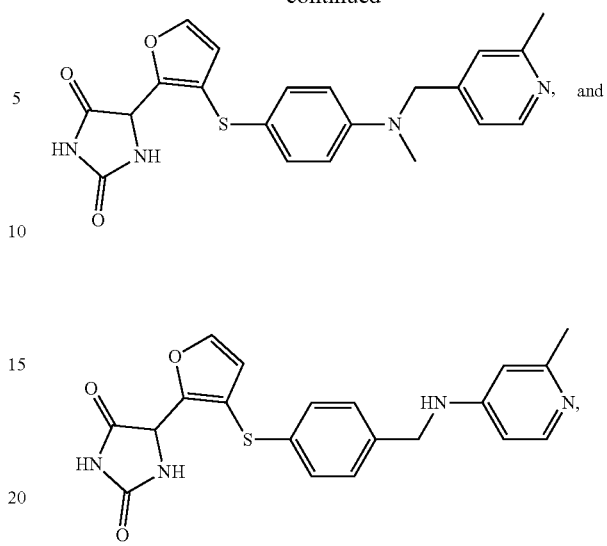

or a tautomer, stereoisomer, pharmaceutically acceptable salt, or solvate thereof.

18. The compound of claim 17, or a pharmaceutically acceptable salt thereof.

19. A pharmaceutical composition comprising the compound of claim 1, and at least one pharmaceutically acceptable carrier.

20. A method of inhibiting macrophage elastase (MMP-12) in a subject in need thereof, the method comprising administering to the subject the pharmaceutical composition of claim 19.

21. A method of treating a disease mediated by macrophage elastase MMP-12 in a subject in need thereof, the method comprising administering to the subject the pharmaceutical composition of claim 19, wherein the disease is selected from the group consisting of asthma, chronic obstructive pulmonary disease (COPD), emphysema, acute lung injury, idiopathic pulmonary fibrosis (IPF), sarcoidosis, systemic sclerosis, liver fibrosis, nonalcoholic steatohepatitis (NASH), arthritis, cancer, heart disease, inflammatory bowel disease (IBD), acute kidney injury (AKI), chronic kidney disease (CKD), Alport syndrome, and nephritis.

\* \* \* \* \*